(12) United States Patent
Abe et al.

(10) Patent No.: US 11,015,175 B2
(45) Date of Patent: May 25, 2021

(54) METHOD FOR MANUFACTURING USEFUL SUBSTANCE IN WHICH HIGH-DENSITY CULTURED STRAIN OF FILAMENTOUS FUNGI IS USED

(71) Applicant: TOHOKU UNIVERSITY, Miyagi (JP)

(72) Inventors: Keietsu Abe, Miyagi (JP); Katsuya Gomi, Miyagi (JP); Kei Yoshimi, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 63 days.

(21) Appl. No.: 14/441,493

(22) PCT Filed: Nov. 8, 2013

(86) PCT No.: PCT/JP2013/080352
§ 371 (c)(1),
(2) Date: May 7, 2015

(87) PCT Pub. No.: WO2014/073674
PCT Pub. Date: May 15, 2014

(65) Prior Publication Data
US 2015/0307852 A1 Oct. 29, 2015

(30) Foreign Application Priority Data
Nov. 9, 2012 (JP) .............................. JP2012-247276

(51) Int. Cl.
| | | |
|---|---|---|
| *C12N 9/10* | (2006.01) | |
| *C12N 15/01* | (2006.01) | |
| *C12N 1/15* | (2006.01) | |
| *C12N 9/02* | (2006.01) | |
| *C12N 1/14* | (2006.01) | |
| *C12N 15/80* | (2006.01) | |
| *C12P 1/02* | (2006.01) | |
| *C12P 7/44* | (2006.01) | |
| *C12P 21/02* | (2006.01) | |
| *C12N 9/62* | (2006.01) | |
| *C12N 9/16* | (2006.01) | |
| *C12N 9/20* | (2006.01) | |
| *C12N 9/26* | (2006.01) | |
| *C12N 9/42* | (2006.01) | |
| *C12N 9/48* | (2006.01) | |
| *C12P 7/46* | (2006.01) | |
| *C12P 7/48* | (2006.01) | |
| *C12P 17/06* | (2006.01) | |
| *C12P 35/00* | (2006.01) | |
| *C12P 37/00* | (2006.01) | |
| *A61K 38/00* | (2006.01) | |

(52) U.S. Cl.
CPC ............ *C12N 9/0004* (2013.01); *C12N 1/14* (2013.01); *C12N 9/1051* (2013.01); *C12N 9/16* (2013.01); *C12N 9/20* (2013.01); *C12N 9/2411* (2013.01); *C12N 9/2437* (2013.01); *C12N 9/485* (2013.01); *C12N 9/62* (2013.01);

*C12N 15/80* (2013.01); *C12P 1/02* (2013.01); *C12P 7/44* (2013.01); *C12P 7/46* (2013.01); *C12P 7/48* (2013.01); *C12P 17/06* (2013.01); *C12P 21/02* (2013.01); *C12P 35/00* (2013.01); *C12P 37/00* (2013.01); *C12Y 204/01183* (2013.01)

(58) Field of Classification Search
CPC .................... C12Y 204/01183; C12N 15/04
See application file for complete search history.

(56) References Cited

U.S. PATENT DOCUMENTS

| | | | | |
|---|---|---|---|---|
| 5,667,990 A | * | 9/1997 | Berka .................. | C12N 9/0065 435/254.3 |
| 5,773,214 A | * | 6/1998 | Peery .................... | C07K 14/38 435/252.3 |
| 6,251,655 B1 | | 6/2001 | Minambres Rodriguez et al. | |
| 6,558,920 B1 | | 5/2003 | Hata et al. | |
| 10,035,986 B2 | | 7/2018 | Van Peij et al. | |
| 2002/0160080 A1 | * | 10/2002 | Hansen .......... | C12Y 302/01008 426/53 |
| 2003/0027286 A1 | * | 2/2003 | Haselbeck ............. | C12N 15/74 435/69.6 |
| 2003/0134353 A1 | * | 7/2003 | Wolff ................... | C12N 9/1205 435/69.1 |

(Continued)

FOREIGN PATENT DOCUMENTS

| | | |
|---|---|---|
| JP | 11-506025 A | 6/1999 |
| JP | 2001-046078 A | 2/2001 |

(Continued)

OTHER PUBLICATIONS

Fontaine et al. (2010) Cell wall alpha 1-3glucans induce the aggregation of germinating conidia of Aspergillus fumigatus, Fungal Gen. Biol., vol. 47, pp. 707-712.*

(Continued)

*Primary Examiner* — Scarlett Y Goon
*Assistant Examiner* — Samuel W Liu
(74) *Attorney, Agent, or Firm* — Wenderoth, Lind & Ponack, L.L.P.

(57) ABSTRACT

An object to be achieved by the present invention is to culture a filamentous fungus at a high density, thereby enabling mass production of a useful substance. The present invention provides a method of producing a substance, including the steps of: culturing a mutant filamentous fungus with no expression of α-1,3-glucan to allow the filamentous fungus to produce a substance; and collecting the resulting substance.

9 Claims, 28 Drawing Sheets
Specification includes a Sequence Listing.

(56) References Cited

U.S. PATENT DOCUMENTS

| | | | |
|---|---|---|---|
| 2007/0196367 A1* | 8/2007 | Dinu | A61K 35/16 424/141.1 |
| 2010/0093601 A1* | 4/2010 | Tyler | A01N 57/12 514/1.1 |
| 2012/0023616 A1 | 1/2012 | Nishimura et al. | |
| 2013/0144034 A1 | 6/2013 | Van Peij et al. | |
| 2013/0224864 A1* | 8/2013 | Dodge | C12N 1/14 435/471 |
| 2013/0276168 A1* | 10/2013 | Romaine | C12N 1/14 800/279 |

FOREIGN PATENT DOCUMENTS

| | | |
|---|---|---|
| JP | 2002-218970 A | 8/2002 |
| JP | 2005-052116 A | 3/2005 |
| JP | 2007-508022 A | 4/2007 |
| JP | 2009-118783 A | 6/2009 |
| JP | 2010-172343 A | 8/2010 |
| JP | 2010-220590 A | 10/2010 |
| JP | 2010-227031 A | 10/2010 |
| JP | 2010-227032 A | 10/2010 |
| WO | 2004/097012 A2 | 11/2004 |
| WO | 2004/097012 A3 | 11/2004 |
| WO | 2005/040369 A1 | 5/2005 |
| WO | 2010/107126 A | 9/2010 |
| WO | 2012/001169 | 1/2012 |

OTHER PUBLICATIONS

Biesebeke et al. (2005) Identification of growth phenotype-related genes in Aspergillus oryzae by heterologous macroarray and suppression subtractive hybridization, Mol. Gen. Genomics, vol. 273, pp. 33-42.*

Miyazawa et al. (2016) Increased enzyme production under liquid culture conditions in the industrial fungus Aspergillus oryzae by disruption of the genes encoding cell wall α-1,3-glucan synthase, Biosci. Biotechnol. BioChem., vol. 80, No. 9, pp. 1853-1863.*

Meletiadis et al. (2001) "Analysis of Growth Characteristics of Filamentous Fungi in Different Nutrient Media", J. Clin. Microbiol., vol. 39, issue 2, pp. 478-484.*

Veses et al. (2009) "Pseudohypha budding patterns of Candida albicans", Med. Mycol., vol. 47, pp. 268-275.*

International Search Report for PCT/JP2013/080352, dated Jan. 28, 2014.

Polacheck, I. et al., Aspergillus nidulans Mutant Lacking alpha-(1,3)-Glucan, Melanin, and Cleistothecia, Journal of Bacteriology, 1977, vol. 132, No. 2, pp. 650-656.

Henry, C. et al., Alpha-1,3 Glucans are Dispensable in Aspergillus fumigatus, Eukaryotic Cell, 2012, vol. 11, No. 1, pp. 26-29.

Sato, H. et al., Kojikin no Ekitai Baiyo ni Okeru alpha-1,3-glucan Gosei Koso Idenshi no Hatsugen to Kinshi Keitai eno Kan'yo, Japan Society for Bioscience, Biotechnology, and Agrochemistry Taikai Koen Yoshishu, 2011, vol. 2011, p. 95.

Hitosugi, M. et al., Aspergillus nigulans ni Okeru alpha-1,3-glucan Kessonkabu no Komitsudo Baiyosei to Busshitsu Seisansei no Hyoka, Japan Society for Bioscience, Biotechnology, and Agrochemistry Taikai Koen Yoshishu, 2013, vol. 2013, p. 1626, Lecture No. 3B13p15.

Hogan, L. et al., Altered Expression of Surface alpha-1,3-Glucan in Genetically Related Strains of Blastomyces dermatitidis that Differ in Virulence, Infection and Immunity, 1994, vol. 62, No. 8, pp. 3543-3546.

Rappleye, C. et al., RNA interference in Histoplasma capsulatum demonstrates a role for alpha-(1,3)-glucan in Virulence, Molecular Microbiology, 2004, vol. 53, No. 1, pp. 153-165.

Beauvais, A. et al., Two alpha-(1-3) Glucan Synthases with Different Functions in Aspergillus fumigatus, Applied and Environmental Microbiology, 2005, vol. 71, No. 3, pp. 1531-1538.

Maubon, D. et al., AGS3, an-alpha-(1-3)glucan Synthase Gene Family Member of Aspergillus fumigatus, Modulates Mycelium Growth in the Lung of Experimentally Infected Mice, Fungal Genetics and Biology, 2006, vol. 43, No. 5, pp. 366-375.

Extended European Search Report for counterpart application No. 13853815, dated Jun. 29, 2016.

Miyazawa et al., "Increased enzyme production under liquid culture conditions in the industrial fungus Aspergillus olyzae by disruption of the genes encoding cell wall α-1,3-glucan synthase", Bioscience, Biotechnology, and Biochemistry, ISSN: 0916-8451 (Print) 1347-6947 (Online) Journal homepage: http://www.tandfonline.com/loi/tbbb20 DOI:10.1080/09168451.2016.1209968.

Lopez, et al., "Production of lovastatin by Aspergillus terreus: effects of the C:N ratio and the principal nutrients on growth and metabolite production", Enzyme and Microbial Technology, 2003, vol. 33, pp. 270-277.

Domingues et al., "The influence of culture conditions on mycelial structure and cellulase production by Trichoderma reesei Rut C-30", Enzyme and Microbial Technology, 2000, vol. 26, pp. 394-401.

Liao et al., "A new approach of pellet formation of a filamentous fungus—Rhizopus oryzae", Bioresource Technology, 2007, vol. 98, pp. 3415-3423.

Sitanggang et al., "Effect of pellet size and stimulating factor on the glucosamine production using Aspergillus sp. CBRC 31742", Bioresource Technology, 2010, vol. 101, pp. 3595-3601.

* cited by examiner

FIG. 2
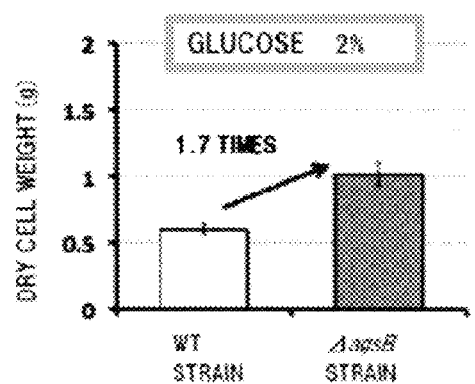
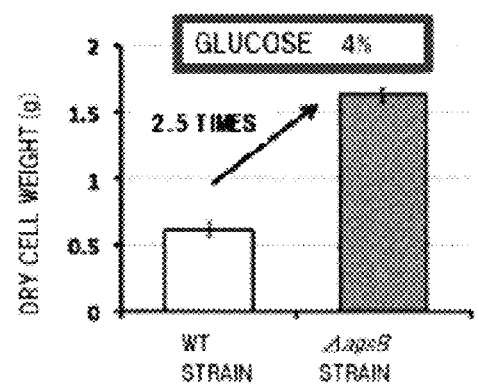

FIG. 3
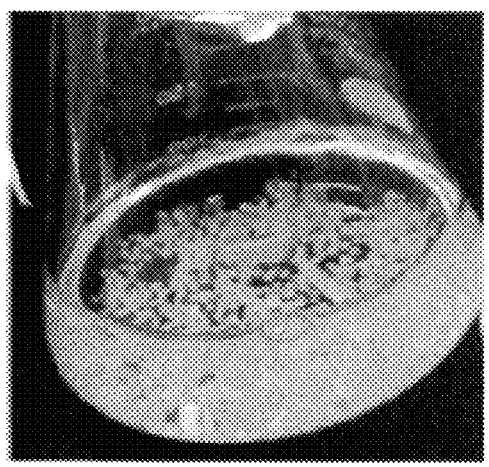
WT STRAIN
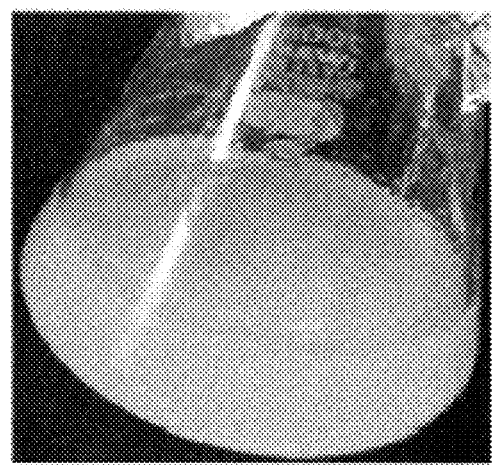
ΔagsB STRAIN

FIG. 9

PUTATIVE AMINO ACID SEQUENCE OF AgsA protein OF As*pergillus nidulans*
MRWRPLNPLLPLLAATAAGWPYEESLVDYNLNVNKNAATPADYYAPEWRNHTYMPSPENWRFPFYTLFLDRFVNGDPTND
NINGTVYEHDLNSNQMRHGGDAQGLVDTLDYLQGMGIKGIYLAGTILMNQPWGADGYSILDTTLLDQHFGTIQTWRNAIT
EIHKRGMYVLFDNTIATMGDLIGFKGYLNVSAPFSVKEHEAVWKSDRRYVDFDFGNTYNQTCEYPRFWNETGWPVDKDVR
DELQGCYSSDFDQYGDREAFGVYPDWQRQLAKFASVQDRLREWNPSVRERLIRHSCMIIKALDIDGFRYDKATQATVDAL
GDMSSAYRECAREVGKNNFFLPGEITGGNNFGSIYLGRGRQPNQYPDSAMDSMAMNNESDHQYFLREDGLQALDSAAFHY
SIYRSLTRFLGLDGNLAAGYDTPIDWTDAWNVMVMTNDMINANTGKFDPRHMFGATNQDVFRWPAIKQGIERQLLAMFIT
TLHLPGIPILLWGEEQGFYILDATADNYVYGRQAMSPATAWKTHGCFQLTADQYHNWPISKGREGCHDETVTYDHRDPSH
PLRNIIKHMYQLRQDYQVLNDGYSVQKLSNQTRQIFYPGSNGTATETGMWSVLRDSVYKIQELHNEQPVWLVYQNDNKTV
EYNFDCSDNDTALISPFATKTTVVNLFYPHDEYDLKDGPKKLHLNGSAEFNGCLDSMTLKPFEFKAFVPKERFVKPRPMI
TKITPGHDQPIISKVVASEAEDLDLSIYFSAEMDCDSVTKAIKVQSTTEVNKTALIDKDSVKCRRIDPNETRWTAQLPSV
WAWSSKLTGVYNGIHRLTVTNATSEVGGSTQAVDHFLIRIGQIDNPMVFTTANYSTDLLHQHENGTLYIRHKAAGADKYR
YSTNWGSSFSNWREYKGGDEFIEEQPWSGTKKQKWNGKHVRVEYWSKLTGSSSYVQEGDYDTKHQRRFPHLFFNGPYNQY
GYDAGLDNEVKQDSDGYWKYRLRAEFPAQGQFNVWGMNPDGKPDQSFVFGDLDSDGVLDRMPPSSLNTLSINVTDRPPSS
YLSWNIWVDDGTMSIQFQPTGSRTIQMVVYFLLWFVPLVTAIGCVYAFMKSFYQVKFNQIGISQKRSLFGFSVGRKPSLN
PLTRLANKSGFLQSTPVFGTGSSRRRSVLIATMEYDIEDWGIRIKIGGLGVMAQLMGKNLGHQDLIWVVPCAGDVDYPED
QPAEPMFVTVLGNIYEVKVQYHVLNNITYVLLDAPVFRQQSKAEPYPARMDDLDSAIYYSAWNQCIAETIKRFPIDLYHI
NDYHGSIAPLYLLPQTIPVCLSLHNAEFQGLWPMRTQKERDEVCSVFNIDVDVARRYVQFGEVFNMLHAGASYLRVHQQG
FGAVGVSRKYGKRSYARYPIFWGLKKVGNLPNPDPSDTAEWNKELPKESEIQVDQNYEASRAELKRQAQEWAGLEQNPNA
DLMVFVGRWSMQKGIDLIADVMPAVLEAHPNVQLICVGPVIDLYGKFAALKLDRMMQLYPGRVFSKPEFTALPPYIFSGA
EFALIPSRDEPFGLVAVEFGRKGALGIGARVGGLGQMPGWWYNVESTTTAHLLHQFKLAIGCALNSKPQVRARMRARSAK
QRFPVAQWVEDLEILQSTAMRIHSKGLAKASVQPYNSGSNTPLGMMTPPIASTGTVTPTGIQTPPLAHSRSGSYSNINRL
SAYGPQQRNTIIYSRDPSPGGEDQPRSGIRQLSLGVRAGPGHLMRRGRRRLRRNSHAGTDENASVSMTEESSDDDIIPSF
YGEEEYTLTPEQAEEVRRADMTPQQEQNHGSVRDFFTRRHSSQSSILSRSVLSPASSTTFDGDETFVPPAPPFAEPGNRL
SSASVLSVDSVVGEKKDYKLQKVDPTFTDSTGEFYKVFERKLEKLNGSNSISQLCIEEYLEKSEKKWFDRFRDARLGRKQ
SPSSSIFRTKFEGSSPMALVSNDEVGSRASGSEPRMRPDEFCLGNDYVPPSGLKKWMQVRIFDWPIYSFILGLGQIIAAN
SYQITLLTGEVGQRPEKLYGIATVYLVSSIVWWFLFRFCKSVVVLSLPWLFYGFAFVLIGVAHYEGDSFARAWIQNVGAG
VYAAASASGSLFFALNFGDENGAPVKNWVWRACIIQGTQQAYIIGLWYWGTSISQAVTRGVPDVQAHITETWRMTTICMP
IAVFLWVLGILVFFGLPNYYRQTPGKVPSFYQSVCRRKIILWNFVVVILQNFFLSAPYGRNWSFLWSSVHAEPWHIGLLV
VAFFGVAWVLILCIFARLSKSHSWILPVFACGLGAPRWAQIWWGVSGMGLFLPWAGSYTTGALVSRSLWLWLGILDSLQG
LGFGMILLQTLTRMHICFTLLASQVLGSIATICARAFAPNNIGPGPISPDITDGAGAVANAWFWIALFFQLLICSFPIDV
MS

FIG. 10A

BASE SEQUENCE OF NUCLEIC ACID MOLECULE ENCODING *agsA* gene OF *Aspergillus nidulans*
ATGAGGTGGAGGCCTTTAAACCCGTTACTTCCGCTGCTTGCAGCAACCGCAGCAGGCTGGCCCTACGAAGAGTCATTAGT
TGATTATAATCTCAACGTGAACAAAAACGCTGCCACCCCAGCAGATTATTACGCACCGGAATGGAGGAACCACACATATA
TGCCGTCGCCAGAGAACTGGAGGTTTCCATTCTACACCCTGTTTCTGGACAGATTCGTCAACGGCGACCCTACTAACGAT
AATATTAACGGAACTGTCTATGAACATGATTTGAACTCCAACCAGATGCGACACGGCGGTGATGCACAAGGCCTGGTAGA
CACACTCGACTACCTTCAAGGAATGGGAATCAAGGTCTGATTTTTGTTTTCGTCTCAGCTTCAGCCTTCGCTAACCAGAT
CTTGTTTAGGGGATCTACCTCGCGGGTACTATTCTCATGAATCAACCCTGGGGCGCAGACGGTTATTCGATTTTGGACAC
TACGCTGCTGGATCAGCACTTCGGGACCATCCAAACCTGGAGAAATGCAATCACAGAGATTCACAAGCGTGGGATGTACG
TCTTATTCGACAACACTATCGCTACGTGAGTCTGCTGGTTTTCCAAGTCAAATGCGCGAATGCTAACTACACCCAAGGAT
GGGCGATTTGATCGGATTCAAAGGTTATTTGAACGTTAGCGCCCCGTTCTCTGTCAAAGAGCACGAAGCTGTTTGGAAGT
CTGACCGTCGCTACGTCGATTTTGATTTTGGAAACACCTACAATCAGACCTGCGAGTACCCTCGATTCTGGAACGAGACT
GGCTGGCCCGTTGATAAAGACGTTCGTGATGAGCTACAAGGTTGCTATAGTAGTGATTTCGATCAATACGGTGACAGGGA
AGCTTTCGGTGTATATCCAGACTGGCAGCGACAGCTGGCCAAGTTTGCATCAGTCCAGGATCGTCTCCGTGAATGGAACC
CAAGCGTTCGCGAGAGACTAATCAGACATTCCTGCATGATTATCAAAGCTCTTGACATTGACGGATTTCGCTATGACAAA
GCCACGCAGGCCACAGTGGACGCCCTTGGAGACATGTCGAGTGCTTATCGTGAGTGTGCCCGTGAGGTCGGTAAAAACAA
CTTTTTCCTCCCAGGTGAGATTACTGGTGGAAACAATTTCGGCTCGATCTATCTCGGACGAGGAAGACAGCCCAACCAAT
ACCCAGACTCTGCTATGGATTCTATGGCCATGAACAACGAGTCGGATCACCAATATTTCTTCGTGAAGATGGTTTACAG
GCGCTCGATAGCGCTGCCTTCCACTACTCAATCTATCGATCCCTCACCCGGTTCCTTGGCCTCGACGGAAATCTTGCTGC
TGGTTACGATACGCCGATTGACTGGACAGATGCCTGGAATGTAATGGTGATGACCAATGACATGATAAACGCGAATACCG
GTAAATTTGACCCGCCGACACATGTTTGGTGCCACGAACCAGGATGTTTTTCGTTGGCCAGCCATCAAACAGGGTATCGAA
CGCCAACTCCTGGCGATGTTCATTACAACACTTCACCTCCCGGGTATTCCAATATTGTTGTGGGGTGAAGAGCAAGGTTT
CTATATCTTGGACGCCACTGCAGACAACTATGTCTACGGCCGCCAGGCGATGTCACCAGCCACAGCTTGGAAAACCCATG
GATGCTTCCAATTGACAGCAGATCAGTACCACAACTGGCCTATCAGCAAAGGACGTGAAGGCTGTCATGACGAGACAGTA
ACCTATGACCACCGCGACCCGTCTCATCCGCTCCGAAATATCATCAAACATATGTACCAGTTGCGACAAGATTACCAGGT
TTTGAACGACGGATATTCTGTCCAGAAACTCTCCAATCAAACCCGCCAGATTTTCTATCCAGGCTCGAACGGAACGGCTA
CGGAGACCGGAATGTGGTCTGTCTTACGAGACTCAGTTTACAAGATCCAGGAGCTACACAACGAGCAACCGGTTTGGCTT
GTATACCAGAATGACAACAAGACGGTGGAATACAATTTTGACTGCAGTGATAATGACACGGCGTTGATATCCCCCTTTGC
CACCCAAAACCACGGTTGTCAATCTCTTTTACCCGCATGACGAATATGACTTGAAGGACGGTCCAAAGAAGCTCCATCTTA
ATGGCTCAGCGGAGTTCAATGGATGCCTTGATAGCATGACGCTGAAGCCTTTCGAATTCAAGGCTTTCGTTCCGAAAGAG
CGATTTGTGAAGCCTAGACCCATGATTACCAAAATCACACCAGGACACGACCAACCGATCATTTCCAAAGTCGTGGCGAG
CGAGGCAGAGGATCTTGATTTGAGCATTTACTTCTCTGCGGAAGTGGACTGCGACTCAGTCACAAAAGCGATCAAAGTGC
AGTCCACCACAGAAGTCAATAAGACAGCTTTGATTGACAAAGACAGCGTGAAATGCAGGAGGATTGATCCAAACGAAACG
CGGTGGACTGCCCAGCTACCCAGCCGTCTGGGCGTGGTCGTCAAAGTTGACCGGAGTATACAATGGAATTCATCGGCTGAC
CGTCACCAATGCCACCAGCGAGGTTGGAGGCTCAACACAGGCTGTTGATCACTTTCTCATTCGCATTGGTCAAATAGACA
ATCCCATGGTCTTCACCACGGCCAATTACTCCACTGACCTACTTCACCAGCACGAGAACGGAACACTCTATATTCGACAC
AAAGCCGCTGGTGCTGATAAATATCGTTATTCCACCAATTGGGGAAGCTCTTTTTCAAACTGGCGCGAATACAAAGGTGG
CGACCGAATTCATTGAAGAACAACCATGGTCCGGAACTAAAAAGCAGAAATGGAATGGGAAGCATGTCCGCGTTGAGTACT
GGAGCAAGTTGACTGGTAGCAGCAGCTATGTCCAAGAAGGTGACTATGATACCAAGCATCAAAGACGCTTCCCGCACCTC
TTCTTCAATGGGCCTTACAACCAGTATGGATACGATGCAGGACTGGACAATGAGGTGAAACAGGACAGTGACGGGTACTG
GAAATATCGGCTCCGAGCGGAATTCCCTGCTCAGGGACAGTTTAATGTTTGGGGTATGAACCCAGACGGGAAGCCCGACC
AGAGTTTTGTGTTTGGTGATCTTGATTCTGACGGTGTTTTGGACCGCATGCCACCATCCTCCCTGAACACCCTTTCTATT
AACGTCACCGACAGGCCACCGTCGTCCTATCTATCTTGGAATATTTGGGTCGATGACGGTACCATGAGCATCCAGTTTCA
ACCGACTGGCTCGAGGACAATCCAGATGGTAGTTTATTTCTTGCTTTGGTTCGTACCGCTTGTGACAGCTATCGGATGCG
TATATGCTTTCATGAAATCGTTTTACCAGGTCAAATTCAACCAGATTGGAATCAGCCAGAAGCGGTCATTATTCGGTTTC
TCAGTCGGCCGGAAGCCTTCATTGAATCCACTGACGCGGCTTGCCAATAAATCCGGATTTCTCCAAAGCACGCCTGTCTT
TGGAACAGGGTCTTCTCGCAGGCGCAGTGTTCTCATCGCCACTATGGAGTATGACATTGAGGACTGGGGTATCAGGATTA
AAATTGGTGGTCTTGGAGTCATGGGCACAGCTCATGGGCAAGAACCTCGGGCATCAAGATCTCATTTGGGTTGTCCCATGT
GCGGGGGACGTAGACTACCCAGAGGATCAGCCAGCTGAGCCAATGTTTGTGACTGTTCTCGGGAACATCTACGAAGTCAA

GGTTCAGTATCATGTCCTGAACAATATTACATATGTTCTTCTCGATGCGCCCGTTTTCCGTCAACAGTCAAAGGCTGAGC
CCTACCCTGCTCGCATGGACGACCTTGATAGTGCGATATACTATTCCGCCTGGAATCAGTGCATTGCTGAGACCATCAAG
CGCTTCCCTATCGACCTTTATCATATCAATGATTATCATGGTTCTATTGCGCCTCTCTACCTTCTTCCCCAGACGATCCC
TGTTTGTCTTTCGCTTCACAACGCCGAATTTCAGGGTCTCTGGCCCATGCGCACACAAAAGGAAAGGGATGAGGTTTGCT
CTGTTTTCAATATCGACGTCGATGTCGCCAGGCGATATGTCCAATTTGGCGAAGTTTTTAACATGCTCCATGCCGGTGCT
AGCTACCTTCGTGTCCACCAACAAGGGTTCGGCGCTGTAGGTGTTTCCAGGAAATATGGAAAACGCTCGTACGCGCGCTA
TCCCATCTTCTGGGGTCTCAAGAAGGTTGGGAATCTTCCGAACCCAGATCCTTCTGACACGGCTGAATGGAACAAGGAAC
TGCCTAAAGAAAGTGAGATCCAGGTAGACCAGAACTACGAGGCAAGCAGGGCAGAGCTGAAACGGCAAGCGCAGGAATGG
GCGGGGCCTTGAACAAAACCCTAATGCTGACCTTATGGTTTTCGTGGGACGGTGGTCGATGCAGAAAGGAATCGATCTGAT
AGCTGATGTTATGCCCGCTGTTTTGGAGGCTCATCCCAATGTTCAGCTGATCTGTCGGCCCAGTCATTGACCTTTATG
GAAAATTTGCCGCCCTGAAGCTTGACCGGATGATGCAGCTCTACCCTGGGCGTGTGTTCTCAAAGCCCGAGTTTACAGCA
CTTCCTCCATACATATTTTCAGGAGCGGAGTTTGCCTTGATCCCATCCCGTGACGAACCGTTCGGACTGGTTGCCGTTGA
ATTTGGTCGCAAGGGAGCCTTGGGAATCGGTGCACGTGTTGGAGGGCTTGGCCAGATGCCGGGTTGGTGGTATAATGTTG
AATCAACAACTACTGCCCATCTGCTTCATCAATTTAAACTAGCTATCGGATGTGCCTTGAACTCGAAACCCCAAGTTAGG
GCAAGGATGCGTGCAAGATCTGCAAAGCAGCGTTTCCCTGTTGCTCAATGGGTTGAGGACCTCGAGATTCTACAGTCAAC
GGCCATGCGAATCCACAGCAAAGGCTTGGCTAAGGCGAGCGTCCAGCCCTATAACTCAGGAAGCAACACCCCACTTGGCA
TGATGACGCCCCTATTGCGTCGACTGGGACTGTTACCCCGACGGGAATCCAGACACCTCCTCTTGCCCATTCGCGATCA
GGAAGCTACTCAAACATCAACCGCCTCAGTGCTTATGGGCCTCAGCAACGTAACACGATAATCTACAGCCGAGACCCAAG
CCCAGGCGGCGAAGACCAGCCTAGATCTGGTATTCGACAGTTATCACTTGGTGTTAGGGCTGGGCCTGGACATCTTATGC
GTCGTGGCCGCCGCAGGTTGAGAAGAAATAGCCACGCGGGGACGGACGAGAACGCCAGCGTCTCCATGACGGAGGAGAGT
AGCGACGACGATATAATCCCAAGTTTCTACGGGGAAGAGGAGTACACGCTTACCCCTGAACAGGCTGAGGAAGTACGTCG
CGCAGATATGACACCACAGCAGGAACAGAATCATGGCTCGGTTAGGGACTTCTTTACCCGTCGTCACTCGAGTCAGAGCT
CGATTTTGTCTCGTAGTGTTTTGTCTCCAGCCAGTTCGACTACGTTTGACGGGGACGAGACCTTCGTTCCACCCGCACCA
CCGTTTGCAGAACCTGGAAACCGTCTCAGCAGTGCGTCGGTACTCTCTGTTGACTCAGTAGTGGGCGAGAAGAAAGATTA
CAAACTGCAAAAAGTTGATCCTACATTTACCGATAGCACTGGCGAATTCTACAAGGTTTTTGAAAGAAAACTAGAAAAGC
TCAATGGCTCGAACTCCATCTCCCAACTTTGCATCGAGGAATATCTGGAGAAGAGCGAAAAGAAATGGTTTGACCGATTC
CGTGATGCACGACTTGGCCGCAAACAGTCCCCGTCGTCTTCCATTTTCCGCACCAAGTTTGAAGGCTCCTCGCCTATGGC
ACTCGTATCAAACGATGAAGTCGGATCGCGCGCGAGTGGAAGCGAGCCCCGTATGAGGCCTGACGAATTTTGTCTTGGAA
ACGACTATGTTCCTCCCTCTGGGCTCAAGAAGTGGATGCAAGTTCGGATTTTCGACTGGCCCATTTACTCCTTCATTCTC
GGACTGGGCCAAATTATAGCAGCGAACTCTTACCAGATCACCTTGTTGACTGGAGAAGTCGGCCAGCGGCCTGAGAAGCT
CTATGGTATTGCAACAGTATACCTCGTGAGCTCTATAGTCTGGTGGTTTCTTTTCCGCTTTTGCAAATCTGTCGTGGTAC
TGTCTCTGCCCTGGCTGTTCTACGGTTTCGCCTTTGTTCTTATTGGAGTCGCACACTATGAGGGCGATAGCTTCGCTCGT
GCTTGGATCCAGAACGTTGGAGCCGGTGTATACGCCGCTGCATCAGCCAGTGGCTCATTGTTTTTCGCCCTTAACTTCGG
AGACGAAAACGGTGCACCAGTCAAGAATTGGGTGTGGCGTGCTTGCATCATACAAGGTACCCAGCAAGCCTACATCATCG
GTCTTTGGTACTGGGGGACTTCTATATCGCAAGCAGTCACCAGAGCGCGTTCCGGATGTTCAAGCCCATATCACGGAGACA
TGGAGAATGACGTACGTGCCTCCATACTCTCCAACGGTCCTTTACTAACTCTATATTGCAGTACTATCTGTATGCCGATA
GCAGTCTTTCTCTGGGTACTCGGCATCCTTGTCTTCTTTGGCCTACCAAACTATTACCGCCAGACGCCTGGAAAAGTCCC
TTCGTTCTACCAATCTGTCTGCCGTCGGAAGATCATCCTCTGGAACTTCGTAGTGGTCATTCTGCAAAATTTCTTCCTCA
GCGCCCCCTACGGACGAAACTGGAGCTGTAAGTCCCAAAAAAATCACTTTATTGTTCCGAAACTAAACTAAGGAAACAGT
CCTCTGGAGCTCCGTCCACGCGGAAACCCTGGCACATCGGCCTTCTGGTCGTCGCCTTCTTCGGAGTCGCCTGGGTTCTCA
TCCTCTGTATCTTCGCCCGGCTTTCCAAATCCCACAGTTGGATCCTCCCCGTTTTTGCCTGCGGTCTTGGTGCCCCGCGA
TGGGCACAGATCTGGTGGGGGGTCTCGGGAATGGGCTTATTCCTCCCTTGGGCAGGAAGCTACACGACCGGCGCACTAGT
ATCTCGCTCTCTCTGGCTATGGCTGGGTATTCTCGACTCCCTGCAAGGCTTAGGCTTTGGTATGATTCTATTACAAACAC
TCACACGGATGCATATCTGCTTCACGCTTTTGGCGAGTCAAGTCCTAGGCTCTATTGCGACGATCTGCGCCAGGGCTTTT
GCGCCGAATAATATCGGGCCAGGGCCCATCTCTCCTGATATTACGGATGGAGCGGGCGCCGTTGCAAACGCGTGGTTCTG
GATTGCGTTGTTCTTCCAGTTGTTGATTTGGTATGTCTTCCTACTATATAATTGGAGCCTAGTGGGACGTAAACTAATAG
TTCGATCTAGTGCTGGGTTCCTCATGTTCTTCCGGAAAGAGCAGCTTACGAAACCCTAAATACCATCGCAACTCGACCTC

FIG. 10C
CONTINUED

GCCATTGCCATTACCCTGGTTACTTTGTCAATTCTTGACATAATCACTACAGCCGGTAATCTACCCGGTGGCGCCCCATT
GCCTGACAATCTTGCTCTCGAATCTCTCCATTGTCCCATCAGCCTATTTACTCTACCCTTTATTGATCTTGCTGTCCATC
GACAGACCGTGCATATTTGCAACTTCTTGACGATATTTGACCTCACCTCTTGAACGAAAAGAATGACTGCTATGAGTCAA
CCTAATGATTGGATGTTATATGGTCTCTTATTCTTCTATGGAACTGACTTATCATTGTGCCCGCCATGACGTGATTTGAT
GTGGGTGAGATGTGGGTGATATGTACCTAATGATACTACTTTGTTGATTAGTTCCTTCCCTATTGATGTTATGTCATAA

FIG. 11

PUTATIVE AMINO ACID SEQUENCE OF AgsB protein OF *Aspergillus nidulans*

MGRLQLSSGLKAIALLTFAATATCWPYDESLVDYNVNTNKSATNPADYWGEWSDHKYHPSPENWRFPFYTLFMDRFVNGD
PTNDNINGTTFEHDLNSNQMRHGGDVAGLVDTLDYLQGMGIKGLYLAGTPLMNQPWGSDGYSALDTTLLDQHFGTIQVWR
DAITEIHKRGILGDLIGFEGHLNDTTPFSEKEHKALWKSNRRYVDFDIGNTYNATCDYPRFWYEDGMPVNESLTAGLVGC
YDSDFDQYGDIEAFGVWPDWKRQLAKFASVQDRLREWYPPVRERLIRHTCMIIASFDIDGIRYDKATQATVDALGDMSKA
YRECARAVGKENFFIAGEITGGNTFGSIYLGRGRQSNQVDSVGNIYDAMKLTNESDPQLFLREVGHEAIDAGAFHYSTYR
ALTRFLGMDGQLEAGYDVPLDWVQAWGNMTVTNDLINANTGKFDPRHMYGVTNQDVFRWPAIEWGVERQMLGSFITTLML
PGIPLLLWGEEQAFYVLDATASNYIYGRQAMSSATAWKTHGCFSLESSQYYQWPLVAALDGCNDETVTYDHRDPSHPVRN
IIKHMYQMREQYPMLNDGFIIETLSNQTEPVYYPGSNGTETETGMWSVRRDRNEETQDFGSSDDNEPIWLVYSNMNRTHD
YTFDCSDNETALIAAFPSGTKVRNLFHPYDTLTLGDGPKEMVYGNSTELVGCLPNLTLSRYEFRAYVKNELWKKPRPMIT
KFQPGDDEANGHDSPLRSTVAPDASETVRLTLQFSEAMGCDSVTDSISFNSSTETGKIPSIDASTVQCGNITEVANSNAT
GHIPGKWQWAADLRGVYNGIHRVTVNNASNADGDDSTHAVDHFLFRIGQIDNPMVFTSANYSSSLLHEKEDGTFYIQHHA
AGADKYRYSTNWGTTFSDWKTYKGGNDTITMLPWNGTKAQEWEGHHIRVEYWSRWTGSSSHVQEGDSGWKYKTPRRFPHA
FFNGPYNQYGYDGGLDNQIKLDAGAGGDGYWKYHFTSEWPAVGQVNVWGINPDGEPDQSWVMGDVDGDKVLDRMPPSALS
ATLINITDHPTHPYISWKLYINDATMRYYLIPAGHQSGQIAMFVLFWIIPLLSGSACVYIFMKSFYKVKFNEIGAAGAST
EMKSLVPLALRRRMKQLASGNGKNGPSFNPLMRLAEKSGFMQSTTALAGAASGKRRMVLIATMEYDIEDWGIKIKIGGLG
VMAQLMGKTLGHQDLIWVVPCVGGVDYPVDTPAEPMTVTILGQAYQVNVQYHVLKNITYVLLDAPVFRQQTKSEPYPARM
DDLDSAVYYSAWNQCIAEAIKRFPVDLYHINDYHGSVAPLYLLPGTIPACLSLHNAEFQGLWPMRTQKEKEEVCSVFNLD
VEVVRNYVQFGEVFNLLHAGASYLRVHQQGFGAVGVSKKYGKRSYARYPIFWGLRKIGNLPNPDPSDVGEWTKEDSLIKD
EDIKVDPEFEAGRAELKRQAQEWAGLDQNPDADLLVFVGRWSMQKGVDLIADVMPAVLEARPNVQLICVGPVIDLYGRFA
ALKLDRMMKVYPGRVFSRPEFTALPPYIFSGAEFALIPSRDEPFGLVAVEFGRKGALGIGARVGGLGQMPGWWYNVESVS
TSHLLMQFKLAIEAALSSKTETRAMMRARSAKQRFPVAQWVEDLEILQSTAIQVHEKEVSRGHAGGRPMTPMTPSGATTP
SGMMTPTTGSRGLKPLSQGVGMGLSVPHSRESSYSNLNRLSEYVAQKTPGESQPRESSGLQRSLSLGVRSGPGHRGRARK
QKPGADNIPEGNEDGSSSDTESIPDYYDDEYTLTPAQIEESRRAQATRSISFSPETLQPPRSPLPAPPMSPGTPPSVEQT
LLPPPKPFAAADAGNRLSSASVLSLDSVVGGKKDFKLQKVDPFFTDSNGEYARNFEQQLENLNGSNSESQLCIEEFLVKS
ERRWFNKFRDARLGRLRSPTPSVFRDNHSHGRGSPDGSMYVDEAGHRNSGDAVHDNGSDDTDDEFLLGKDYVPPTGLKKW
MQIKIGDWPVYTLFLALGQIIAANSYQITLLTGEVGQTAEKLYGIATTYAITSALWWLVFRYFKSIVCLSTPWFLYGIAF
LFIGSAHFESDSFTRGWIQNVGSGFYAAASSSGSIFFALNFGDEGGAPVSKWIFRACVIQGIQQVYVIVLWYWGSTMAHQ
SSQGLLTADNTISNTWKMTAICYPIAMLLWAIGLLLIFGLPNYYRQKPGKVPSFYKSLFRRKIVLWNFVAVILQNFFLSA
PYGRNWSFLWTSSHTKPWQIVILCVIFFGLLWCAFLYIVAVLSKQHSWFLPVFACGLGAPRFLQIWWGVSGIGHYLPWVA
GGYTGGALVSRSIWLWLGVLDSIQGLGFGIILLQTLTRMHMCFTLIVSQVLGSIATIVARACAPNNVGPGPVSPDITKGA
GELANAWFWVALFCQLLVCAGFLLFFRKEQLAKP

FIG. 12A

BASE SEQUENCE OF NUCLEIC ACID MOLECULE ENCODING *agsB* gene OF *Aspergillus nidulans*
ATGGGGAGGCTCCAGCTCTCAAGCGGGCTGAAGGCCATAGCCCTGCTCACATTCGCAGCGACAGCAACATGCTGGCCATA
CGACGAGTCCCTCGTTGACTACAACGTCAACACGAATAAGTCGGCCACTAACCCCGCCGACTACTGGGGAGAATGGTCGG
ATCACAAGTACCATCCGTCGCCAGAGAACTGGCGGTTTCCGTTTTACACACTCTTCATGGACAGATTCGTGAATGGGGAT
CCAACAAATGATAACATCAACGGGACCACGTTTGAGCACGATCTCAATTCAAATCAGATGCGTCATGGCGGTGATGTTGC
TGGGCTGGTTGATACGCTGGATTACTTGCAAGGGATGGGGATCAAGGTGCGTTGCCGCTATTATTCGTCAATTTCTGGTA
AAGATATAGTTGATGCTAACGATGCGATAGGGACTGTACCTTGCTGGAACTCCGCTCATGAACCAGCCCTGGGGCTCGGA
TGGGTATTCGGCGCTCGACACCACCCTTCTCGACCAGCACTTTGGCACGATCCAGGTCTGGCGCGACGCCATCACCGAAA
TCCACAAACGGGGGATGTACGTTCTGTTCGACAATACAATCGCTACGTGAGTACCTCGCCTCCCTGCGTTTTGCCATCGG
TTTGTAAAAAACTTGGGCCTGACACTAGATTACTGCAGCCTCGGTGATCTCATTGGTTTTGAAGGTCATCTCAACGACAC
CACGCCCTTCTCCGAGAAAGAACACAAGGCCCTTTGGAAGTCCAACAGACGGTACGTCGATTTCGATATTGGCAACACCT
ACAACGCCACCTGTGATTATCCGCGCTTCTGGTACGAGGACGGGATGCCAGTCAATGAGTCCCTGACCGCGGGCCTGGTC
GGGTGTTATGATAGTGACTTTGACCAGTACGGTGACATCGAAGCGTTCGGTGTCTGGCCAGACTGGAAGCGTCAACTGGC
GAAGTTTGCGTCCGTCCAGGATCGGTTGAGAGAATGGTACCCACCTGTACGGGAACGGCTGATCCGACACACATGCATGA
TCATTGCCTCCTTTGATATCGACGGTATTCGGTACGACAAGGCGACCCAGGCGACTGTCGATGCGTTGGGGGACATGTCC
AAAGCGTATCGGGAATGCGGCGGGCTGTCGGCAAGGAGAACTTTTTCATTGCGGGTGAGATCACAGGAGGCAATACTTT
TGGGTCTATCTATCTCGGACGAGGACGGCAGTCGAACCAGGTCGATTCGGTGGGGAATATCTACGACGCCATGAAACTGA
CAAACGAGTCGGATCCGCAGCTTTTCCTGCGCGAGGTCGGCCACGAGGCTATCGACGCCGGTGCCTTCCATTACTCGACT
TACCGTGCCCTGACCCGCTTCCTGGGAATGGACGGGCAGCTGGAGGCCGGTTATGACGTCCCTCTTGACTGGGTGCAGGC
ATGGGAAACATGACCGTGACCAACGACCTGATTAACGCCAACACGGGCAAGTTCGATCCCCGGCACATGTACGGCGTGA
CAAACCAGGATGTTTTCCGTTGGCCGGCAATCGAGTGGGGTGTTGAGAGGCAGATGCTGGGCTCGTTTATCACCACGCTG
ATGCTGCCGGGCATCCCGCTGCTGCTTTGGGGAGAGGAGCAAGCGTTCTACGTGCTCGATGCGACGGCGTCAAACTACAT
ATATGGACGACAGGCCATGTCGTCTGCGACCGCGTGGAAGACGCACGGCTGCTTCTCACTCGAATCGAGCCAGTACTACC
AGTGGCCCCTGGTGGCCGCACTCGACGGTTGCAACGACGAGACGGTCACCTACGACCACCGGGACCCGAGCCACCCGGTG
CGCAACATCATCAAGCACATGTACCAGATGCGCGAGCAGTACCCAATGCTCAACGATGGGTTCATCATCGAGACCCTTTC
TAACCAGACGGAACCTGTCTACTACCCCGGTTCCAACGGGACCGAGACCGAGACAGGCATGTGGTCGGTCCGCCGTGACC
GGAACGAAGAGACCCAGGACTTTGGCTCGAGTGACGACAACGAACCCATCTGGCTAGTCTATAGCAACATGAACCGCACG
CACGACTACACATTTGATTGCTCTGACAATGAGACGGCACTCATTGCCGCCTTCCCCTCAGGCACCAAGGTCAGGAACCT
CTTTCACCCGTACGACACGCTGACCCTAGGCGACGGGCCAAAGGAAATGGTCTATGGCAACTCGACTGAGCTGGTAGGCT
GCTTACCGAACCTGACGCTTAGCCGGTACGAGTTCCGTGCCTATGTCAAGAACGAGCTCTGGAAAAAGCCCCGGCCGATG
ATCACCAAGTTCCAGCCCGGCGACGATGAGGCCAACGGCCACGACAGCCCGCTGCGTTCGACCGTCGCACCAGATGCGTC
CGAGACGGTGCGACTGACGCTGCAGTTTTCTGAGGCGATGGGATGCGATTCTGTCACAGACTCCATCTCATTTAACTCTT
CCACGGAAACCGGCAAGATTCCATCCATCGACGCCTCCACCGTCCAGTGTGGGAACATCACTGAAGTCGCCAACAGCAAC
GCTACCGGGCACATCCCCGGTAAGTGGCAGTGGGCTGCAGATCTGAGAGGGGTGTACAACGGCATCCACCGGGTCACTGT
CAACAACGCCAGCAACGCCGACGGGGACGACTCCACCCACGCAGTCGACCACTTCCTCTTCCGGATTGGGCAGATTGACA
ACCCCATGGTCTTTACCTCTGCCAACTACTCCAGCAGTTTGCTGCATGAGAAGGAGGACGGCACGTTCTATATCCAACAC
CACGCTGCCGGTGCTGACAAGTACCGCTATTCGACGAATTGGGGCACCACGTTCTCTGACTGGAAAACGTACAAGGGAGG
TAACGACACGATTACCATGCTTCCATGGAATGGCACTAAGGCGCAGGAATGGGAGGGACATCACATCCGCGTCGAGTACT
GGTCCCGCTGGACTGGCAGCAGTAGCCACGTCCAGGAAGGCGATTCCGGCTGGAAGTACAAGACGCCACGTCGCTTCCCA
CATGCCTTTTTCAATGGGCCCTACAACCAGTACGGGTACGACGGCGGTCTGGACAACCAGATCAAGCTGGACGCGGGCGC
CGGCGGCGACGGATACTGGAAGTACCATTTCACCTCGGAGTGGCCTGCCGTCGGGCAGGTGAATGTCTGGGGCATCAATC
CGGATGGGCGAGCCCGATCAGAGCTGGGTGATGGGCGACGTGGACGGGGACAAGGTCCTCGACCGCATGCCACCAAGCGCG
CTCTCTGCAACGCTGATTAACATCACTGATCACCCAACGCACCCTTATATCTCGTGGAAGCTGTACATAAACGACGCGAC
GATGCGGTACTATCTCATCCCCGCTGGCCACCAGAGCGGGCAGATCGCCATGTTCGTCCTCTTCTGGATCATCCCTCTCC
TGTCCGGCTCCGCCTGCGTCTATATCTTCATGAAGTCCTTCTACAAGGTCAAATTCAACGAAATCGGCGCTGCCGGCCGA
AGCACGGAAATGAAGTCACTTGTCCCGCTTGCTCTCCGTCGACGCATGAAGCAGCTCGCCTCTGGGAATGGCAAGAACGG
TCCGTCATTCAACCCGCTCATCGCCTTGCTGAAAAGTCCGGCTTTATGCAGAGCACGACTGCGTTGGCCGGTGCGGCCT
CGGGCAAGAGACGCATGGTCCTGATCGCGACCATGGAATACGATATTGAAGACTGGGGGATCAAGATCAAGATCGGTGGT

CTGGGAGTGATGGCCCAGCTGATGGGTAAGACACTCGGCCACCAGGACCTTATCTGGGTGGTGCCTTGTGTCGGGGGCGT
GGACTATCCTGTTGATACCCCTGCGGAACCCATGACGGTCACTATCCTGGGTCAGGCATACCAGGTGAACGTGCAGTACC
ACGTTCTGAAGAACATCACGTACGTCTTGCTTGACGCGCCCGTCTTCCGCCAGCAGACCAAGTCGGAGCCGTACCCAGCG
CGCATGGATGACTTGGACTCTGCAGTGTATTACTCCGCATGGAATCAGTGTATCGCAGAGGCGATCAAACGGTTCCCTGT
TGATTTGTACCATATTAACGATTACCACGGCTCTGTCGCGCCGCTGTACCTCCTGCCAGGTACCATCCCCGCCTGTCTGT
CACTTCACAATGCCGAGTTTCAGGGTCTATGGCCGATGCGAACACAGAAGGAGAAAGAGGAGGTCTGTTCCGTGTTCAAC
CTGGATGTTGAGGTTGTCCGCAACTACGTCCAGTTTGGTGAGGTGTTCAACCTCCTCCACGCAGGAGCGAGCTATCTCCG
CGTTCACCAACAGGGCTTTGGTGCCGTCGGTGTCTCGAAGAAGTACGGCAAGCGTTCATATGCTCGGTACCCGATCTTCT
GGGGCCTGCGCAAGATCGGAAACCTGCCGAACCCCGATCCGTCTGATGTGGGCGAGTGGACGAAGGAGGACAGCCTGATC
AAGGACGAGGATATCAAGGTGGATCCAGAGTTTGAAGCAGGCCGCGCTGAGCTCAAGAGACAGGCGCAGGAGTGGGCTGG
GCTGGACCAGAACCCTGATGCTGACCTCCTGGTTTTCGTCGGTCGTTGGTCCATGCAGAAGGGTGTTGACCTTATCGCAG
ACGTTATGCCCGCAGTCCTTGAAGCACGACCAAACGTACAGCTCATCTGTGTTGGACCTGTTATCGATCTCTATGGCCGC
TTTGCCGGCGCTCAAGCTCGACCGCATGATGAAGGTGTATCCCGGCCGCGTCTTCTCACGCCCTGAATTCACTGCCCTGCC
GCCGTATATCTTCTCCGGCGCGGAATTCGCGCTTATTCCCTCCCGTGACGAACCCTTTGGTCTTGTCGCCGTCGAGTTTG
GCCGCAAAGGTGCGCTCGGCATTGGAGCCCGTGTTGGTGGACTGGGACAGATGCCTGGATGGTGGTACAATGTCGAATCG
GTCTCGACATCCCATCTCCTCATGCAGTTCAAGCTCGCTATTGAGGCTGCCCTTTCGTCAAAGACTGAGACACGTGCTAT
GATGCGTGCTCGCTCTGCTAAACAACGCTTCCCCGTTGCGCAGTGGGTGGAAGATCTGGAGATCCTACAGTCGACTGCTA
TCCAGGTTCATGAGAAGGAGGTTTCCCGTGGTCATGCAGGTGGCCGCCCCATGACACCGATGACGCCCTCTGGAGCTACG
ACGCCCAGCGGAATGATGACGCCTACTACAGGATCCCGTGGTCTTAAGCCTCTGTCCCAGGGCGTCGGCATGGGCCTCTC
GGTGCCACACTCCCGGGAGAGCAGCTATTCGAACCTCAACCGATTGAGCGAGTACGTTGCGCAAAAGACTCCGGGCGAGT
CTCAACCGCGAGAATCGTCCGGTCTGCAGCGCTCGCTCTCGCTCGGTGTCCGGTCCGGTCCTGGCCACCGTGGTCGTGCG
CGCAAGCAGAAACCCGGCGCGGACAACATCCCGGAGGGCAACGAGGACGGCAGCAGCAGTGATACTGAGTCTATCCCTGA
CTACTACGACGACGAGTACACCCTCACCCCAGCTCAGATTGAAGAAAGCAGACCGGGCTCAGGCCCACCCGTTCCATATCCT
TCAGCCCCGAGACACTCCAGCCACCTCGATCTCCCCTGCCCGCACCTCCCATGAGTCCCGGGACGCCACCGTCGGTTGAG
CAGACTCTGCTGCCTCCACCAAAGCCCTTCGCTGCCGCTGACGCTGGAAACAGACTTAGTAGTGCATCAGTGTTATCCCT
AGACTCTGTCGTGGGTGGGAAGAAAGACTTCAAGCTCCAAAAGGTCGACCCCTTCTTTACTGACAGCAACGGCGAGTATG
CTCGGAACTTCGAACAGCAGCTCGAGAACCTCAACGGCTCCAACTCCGAGTCACAGCTGTGTATCGAGGAGTTCCTTGTC
AAATCGGAACGCCGCTGGTTCAACAAGTTCCGCGATGCAAGGCTGGGTCGTCTGCGCTCGCCCACACCGTCTGTCTTCCG
CGACAACCACAGCCACGGCCGGGGCTCGCCCGATGGATCTATGTATGTGGATGAGGCAGGCCACCGTAATAGTGGCGATG
CCGTGCACGACAACGGCTCAGATGACACAGACGATGAGTTCCTCCTAGGCAAAGACTACGTGCCTCCCACGGGCCTGAAG
AAATGGATGCAGATCAAGATCGGCGACTGGCCGGTGTACACGCTCTTCCTCGCACTGGGCCAGATCATCGCTGCAAACTC
CTACCAGATCACGCTGCTGACAGGCGAAGTCGGCCAAACAGCCGAGAAACTGTACGGAATTGCCACAACCTATGCCATAA
CCTCAGCCCTCTGGTGGCTCGTCTTCCGGTACTTCAAATCCATCGTCTGCCTCTCCACCCCCTGGTTCTTGTATGGAATT
GCGTTCCTCTTCATTGGCTCCGCGCACTTTGAGTCCGACTCATTCACCCGCGGCTGGATCCAGAATGTCGGCAGCGGCTT
CTATGCTGCGGCTTCCTCCAGCGGATCCATCTTCTTTGCGCTGAACTTCGGTGATGAGGGCGGTGCACCAGTGAGCAAGT
GGATTTTCCGTGCATGTGTGATTCAGGGCATCCAGCAGGTCTATGTCATTGTGCTCTGGTATTGGGGTTCCACGATGGCA
CACCAGTCCAGCCAGGGTCTGCTCACGGCCGGATAATACGATCTCAAATACGTGGAAGATGACGTACGTCCAAAACGACCC
TAAATTACCCCAATTAATATACAGAACTCACTAACAAACTGATACAGCGCCATTTGCTATCCGATCGCCATGTTACTGT
GGGCCATCGGCCTCCTGCTGATCTTCGGCCTACCAAACTACTACCGCCAGAAACCCGGCAAAGTACCCTCCTTCTACAAA
TCCCTTTTCAGACGCAAGATCGTGCTCTGGAACTTTGTCGCCGTCATCCTACAGAACTTCTTCCTGTCGGCTCCCTATGG
CCGCAACTGGAGTTTCCTCTGGACATCCTCCCACACAAAGCCCTGGCAGATTGTCATCCTGTGTGTCATATTCTTTGGTC
TTCTGTGGTGCGCGTTCCTTTACATTGTCGCTGTTCTTTCGAAGCAGCACTCCTGGTTTTTGCCAGTCTTCGCATGCCGGG
CTCGGCGCCCCCCGCTTCCTGCAAATCTGGTGGGGTGTTTCTGGCATCGGACACTACCTTCCCTGGGTTCCCGGCGGGTA
TACTGGCGGCGCACTAGTTAGTCGGAGTATCTGGCTGTGGCTAGGTGTGCTAGATTCAATCCAGGGGTTAGGGTTCGGAA
TCATTCTCCTCCAAACCCTGACCCGGATGCATATGTGCTTTACGTTGATCGTCAGCCAAGTCCTGGGATCTATAGCAACC
ATCGTTGCGAGGGCATGTGCTCCAAATAATGTTGGTCCGGGACCTGTGAGTCCAGATATCACGAAGGGAGCGGGCGAACT
GGCGAACGCCTGGTTCTGGGTTGCATTGTTCTGTCAGTTGCTTGTCTGTGCTGGGTTCTTACTGTTTTTCCGCAAGGAGC
AACTTGCGAAGCCTTAA

FIG. 17
PUTATIVE AMINO ACID SEQUENCE OF AgsA protein OF *Aspergillus oryzae*
MKWGFTGPLLALLAATAAGWPYDESLVDYNLNVNKDTTNPAEYTHAEWKGHEYNPSPKSWRFPFYTLFIDRFVNGDPTND
NINGSLFEHDLNSNQMRHGGDAAGLVDTLDYLQGMGIKGIYLAGTILMNQPWGSDGYSILDTTLLDQHYGTIQTWRDAIT
EIHKRGMYVLFDNTIATMGDLIGFEGYLNTTTPFSVKEHKALWKSDRQYVDFRFDNEYNNTCEYPRFWNETGYPVDKDVT
DELVGCYNSDFDQYGDREAFGVYPDWERQLAKFASVQDRLREWHPSVKERLIRHSCMIIKALDIDGFRYDKATQATVDAL
GDMSHAYRECARSVGKDNFFLPGEITGGNNFGSIYLGRGRQPNQYPDSSLASMNLTNTSDHQYFLRDDGLQALDSAAFHY
SVYRTLTRFLGMDGNLAAGYDTPLDWTDSWNIMVLSNDMINANTGKFDPRHMYGTTNQDVFRWPAIELGVERQLLGHFIT
TLHLPGIPILLWGEEQAFYILDSTADNYIYGRQAMSPSTAWKTHGCYSLGSSQYYNWPVSAGREGCHDEAVAYDHRDPSH
PVHNIIKHMFQMRQDFPVLNDGYSVVKLSKQTREIQYPGSNGTATEVGVWSVLRDLVSNIQDFGDSGNNEPVWLVYQNDN
KTVEYSFDCGSNDSALISPFTTGTTVVNLFYPHDEHELKDGPKSLHLNGTNATNGCLDTLKLKPFEFRAYVPKANFVKPR
PMITQFEPGHDVPQLSKVGPDESEDIDVSIYFSTKMDCDQVTKSISFESSTEAGKTPSISNNSVSCKDAKGDDPKWTGQI
PNAWVWTAKLTGVYNGIHRLTVKNATSSDGHSSTQATDHFLIRVGQRDNPLVFTSANYSTSLLNQYDNGTLYIQHRAAGA
NKYRYSTNFGSSFSDWKDYHGGNDTIEELPWSGTDKQKWQGKHVRVEYWNKLTGSSDYAQEGDSGYDHPRRFPHLFFNGP
FNQYGYDAGLDNVVRQDSDGLWKFRFMAEFPAQGQFNVWGMNPDGQPDQSYVFGDVDDDGVLDRMPPSSLSSTIINITDI
PPSPYLAWNLGVDDGTLRVHLLPTGSRTIQMVVYFLLWFVPLVTAIACVYAFVKSFYQVKFNQVGVSEKKSILPLAFRRK
LSRDGSGGSINPFMRLANKSGFLQSTPAFGAVASRRRTTLIATMEYDIEDWAIKIKIGGLGVMAQLMGKHLGQQDLIWVV
PCVGGVDYPVDQPAEPMFVTVLGNSYEVKVQYHVLNNIKYVLLDAPVFRQQTKSEPYPARMDDLDSAIYYSAWNQCIAQA
IRRFPIDLYHINDYHGSIAPLYLLPQTIPVCLSLHNAEFQGLWPMRTQKERDEVCSVFNLDLDTAKRYVQFGEVFNMLHA
GASYLRVHQQGFGAVGVSRKYGKRSYARYPIFWGLKKVGNLPNPDPSDTGEWNKELPKDSEIRVDPNYEASRGELKRQAQ
EWAGLDQNPDADLLVFVGRWSMQKGVDLIADVMPAVLEARPNVQLICVGPVIDLYGKFAALKLDHMMRLYPGRVFSKPEF
TALPAYIFSGAEFALIPSRDEPFGLVAVEFGRKGALGIGARVGGLGQMPGWWYNIESTTTSHLLHQFKLAIGSALNSKPQ
VRAKMRARSAKQRFPVAQWVEDLEILQTTAMRIHSKGQAKSNGGPLSPSGYNTPSEVITPSGMMTPTIASTGTTTPTGMQ
TPPIAHSREGSYTNLSVNRDSAYGPQQRNTIVYSRDPSPGGNDEPRLSLGRQLSLGFRAGPGHINLRGRRLKRRSQMTNE
ESGTATEESSDDDYFRGEEEVTITREQADEGRHQRNAPRSLASPPNSYFEEGITSGRPPWAQPGNRLSSASVLSVDSVVG
EKKDYKLQKVDPFFTDGTGEYYRMFDQRLEKLNGSNSESQLCIEEYLMKSEKKWFDKFRDARLGRNQSPASSIFQTKGEN
NTPMSSISHEDLGSNESGSDPRAEKDEFLLGRDYVPPSGLRKWMQIRIFGWPVYSFFLGLGQIIAANSYQITLLAGENCQ
TAEKLYGIATVYLVTSIIWWFFFRFFKSVFVLSIPWFLYGASFVIIGLAHFESNGSARGWIQNVGSGVYAAASSSGSLFF
ALNFGDESGVQVKDWVFRACLIQGTQQAYVIGLWYWGTTISSAVANGVTNVNGGIVNSWKMTAICMPIAAFLWAIGLIIF
FGLPNYYRQSPGKVPSFYKSVFRRKIVLWNFVVVILQNFFLSAPYGRNWAFLWSSNHAEAWQVGILVVVFFGVIWVAVLT
LFGYLSKRHSWILPVFACGLGAPRWAQIWWGVSGMGLFLPWAGSSVSGALASRSLWLWLGILDALQGLGFGMILLQTLTR
VHIAFTLLASQVLGSIATIVARACAPNNIGPGPISPDVTAGGSSVANAWFWIALFFQLLICAGFLLFFRKEQLTKP

FIG. 18A

BASE SEQUENCE OF agsA gene OF Aspergillus oryzae
ATGAAGTGGGGATTCACTGGCCCGTTGCTTGCGTTGCTCGCAGCAACAGCAGCAGGCTGGCCCTATGATGAGTCCCTAGT
CGATTATAACTTGAATGTGAACAAGGATACTACCAATCCGGCTGAATATACTCACGCAGAATGGAAGGGCCATGAGTATA
ATCCCTCTCCAAAAAGCTGGCGATTCCCCTTCTATACCCTGTTCATTGACCGGTTTGTCAATGGCGATCCTACTAACGAT
AACATCAACGGGTCACTCTTTGAACATGATCTTAATTCAAACCAAATGCGTCACGGTGGTGATGCAGCTGGCTTGGTCGA
TACACTAGACTACCTACAAGGTATGGGCATAAAGGTTGGTAGCAATGATCTCCGTGTTGTTTCTTGCTATTGGTGTTTAC
CGGCATATGGCTGACTGACCTCTACAGGGGATCTATTTGGCTGGTACTATCTTGATGAATCAACCATGGGGCTCAGACGGT
TACTCGATTTTGGATACTACCCTGCTTGATCAGCATTATGGTACAATTCAAACCTGGAGAGACGCGATCACCGAGATTCA
TAAGCGGGGCATGTATGTCCTCTTTGACAATACTATCGCAACGTAAGATGCTGCCCCTCACCTAAGTCGTTATATCCCAG
AGCTGACATGAAACCAGCATGGGCGATTTGATTGGATTTGAAGGTTATTTGAATACTACCACGCCTTTCTCAGTCAAGGA
GCACAAAGCATTGTGGAAATCTGACCGTCAGTATGTCGACTTCCGTTTTGACAATGAGTACAACAACACTTGCGAATACC
CTCGATTCTGGAACGAGACTGGCTATCCGGTCGATAAGGATGTCACAGATGAGCTGGTTGGATGCTATAACAGTGATTTC
GACCAGTACGGTGACAGAGAAGCTTTCGGTGTCTACCCAGACTGGGAGCGCCAGTTGGCCAAATTCGCTTCAGTTCAGGA
TCGTCTACGTGAATGGCACCCTAGCGTTAAAGAGAGACTTATTCGGCACTCGTGTATGATTATAAAGGCACTTGACATTG
ATGGCTTCCGCTACGATAAAGCGACGCAGGCCACAGTGGATGCTCTTGGAGACATGTCCCATGCTTATAGAGAGTGTGCT
CGCAGTGTTGGCAAGGATAACTTCTTCCTTCCTGGAGAAATTACTGGTGGAAATAACTTTGGTTCTATTTACCTCGGACG
TGGAAGACAGCCCAACCAATACCCAGACTCCTCCTTGGCTTCGATGAACCTGACGAACACCTCCGATCATCAGTATTTCT
TACGTGATGACGGTCTACAAGCGCTAGATTCAGCAGCTTTCCATTATTCGGTGTACCGTACCCTCACTCGATTCCTAGGT
ATGGATGGCAATCTGGCTGCGGGCTATGACACACCGTTGGACTGGACGGACTCCTGGAATATTATGGTATTGAGCAACGA
TATGATCAATGCTAACACTGGCAAATTTGACCCCCGGCATATGTATGGTACTACAAACCAGGATGTTTTCCGTTGGCCTG
CCATCGAGCTCGGAGTCGAGAGACAGCTTTTGGGTCACTTCATCACAACCTTGCATCTCCCGGGCATCCCAATTTTGCTG
TGGGGAGAAGAACAAGCCTTCTACATTCTAGACTCTACTGCGGATAACTATATCTATGGCCGCCAAGCAATGTCTCCCTC
CACTGCGTGGAAAACACACGGATGTTATTCCCTTGGTTCGTCCCAATACTACAACTGGCCTGTCAGTGCAGGTAGGGAAG
GATGTCATGATGAAGCTGTCGCTTATGATCATCGAGATCCCTCTCATCCAGTCCACAATATCATCAAACATATGTTCCAG
ATGCGACAGGACTTCCCTGTACTAAATGATGGATACTCAGTTGTCAAGTTGTCAAAACAGACTCGTGAGATTCAGTATCC
TGGTTCGAATGGCACGGCAACGGAAGTCGGCGTCTGGTCAGTCCTGCGTGATCTTGTCTCCAACATTCAAGACTTTGGTG
ACAGCGGCAACAACGAACCTGTCTGGCTGGTCTATCAAAATGACAACAAGACCGTGGAATATAGCTTTGATTGTGGGAGT
AACGATTCGGCCTTGATTTCCCCATTTACTACGGGAACTACTGTTGTTAATCTCTTCTACCCACACGATGAACACCGAGCT
TAAAGATGGCCCCAAATCACTTCATCTGAACGGCACCAATGCAACAAACGGTTGTCTGGATACTTTGAAGTTGAAGCCCT
TCGAGTTCAGGGCTTACGTTCCAAAGGCTAACTTTGTTAAGCCTCGTCCCATGATCACCCAGTTCGAGCCTGGTCACGAT
GTGCCGCAGCTGTCTAAAGTCGGACCTGACGAATCAGAAGATATTGACGTGAGCATTTACTTTTCCACCAAGATGGATTG
TGATCAGGTTACGAAATCCATTTCATTCGAATCCAGTACCGAAGCTGGCAAGACTCCCTCTATCAGTAATAACAGTGTCA
GCTGCAAAGATGCCAAGGGTGATGATCCGAAGTGGACTGGTCAAATTCCCAAGCGCTGGGTCTGGACAGCGAAGTTGACT
GGCGTTTACAACGGTATCCATCGCTTGACCGTCAAAAATGCCACTAGCTCGGATGGGCATAGTTCTACCCAGGCAACTGA
TCACTTCTTGATCCGAGTGGGCCAAAGGGATAATCCGTTGGTGTTCACATCTGCGAACTACTCGACCTCCTTGTTAAACC
AGTATGACAATGGCACGCTCTACATCCAACATCGTGCAGCAGGTGCAAACAAATACCGCTATTCAACAAACTTTGGTTCC
TCATTCTCTGACTGGAAAGACTACCACGGAGGGAACGATACTATTGAAGAACTGCCCTGGAGTGGAACGGACAAGCAAAA
GTGGCAAGGGAAGCACGTGCGAGTCGAATACTGGAATAAGTTAACCGGCAGCAGTGACTACGCTCAGGAAGGCGACTCTG
GATATGACCATCCAAGACGCTTTCCCCATCTTTTCTTCAACGGGCCATTCAACCAATATGGATATGATGCGGGCTTGGAC
AACGTTGTGAGGCAAGACAGTGATGGTCTTTGGAAGTTCAGATTCATGGCTGAGTTTCCAGCACAAGGACAGTTCAATGT
TTGGGGAATGAATCCAGATGGTCAACCAGACCAGAGCTACGTGTTCGGTGATGTTGATGATGACGGAGTTTTGGATCGCA
TGCCTCCTTCTTCGCTTAGTTCCACGATAATAAACATCACGGATATCCCTCCATCTCCATACTTGGCGTGGAATCTTGGT
GTTGACGATGGAACTCTGCGTGTTCATCTTCTGCCAACGGGTTCAAGGACCATCCAAATGGTTGTGTACTTCCTCCTCTG
GTTTGTTCCCCTTGTCACAGCCATCGCTTGTGTCTATGCCTTCGTGAAATCCTTCTACCAAGTCAAGTTCAACCAAGTGG
GGGTCAGCGAAAAGAAATCAATTCTTCCATTGGCATTCCGAAGGAAACTGAGCCGTGATGGAAGCGGGGGATCAATCAAT
CCTTTCATGCGCCTTGCCAATAAGTCGGGATTCTTGCAAAGCACACCTGCTTTTGGAGCAGTCGCTTCACGAAGACGGAC
GACCTTGATTGCCACCATGGAATATGATATTGAGGACTGGGCCATCAAGATTAAAATCGGTGGTCTAGGTGTTATGGCTC
AGTTGATGGGCAAACACCTTGGGCAGCAGGATCTAATTTGGGTTGTTCCATGCGTGGGTGGAGTTGACTACCCGGTAGAT
CAGCCAGCTGAGCCTATGTTTGTGACAGTGCTCGGAAATTCCTACGAAGTCAAGGTGCAGTATCACGTCCTGAATAATAT
TAAAATATGTCCTTTTAGATGCTCCTGTTTTTCGTCAACAGACCAAATCTGAGCCTTATCCCGCCCGAATGGACGATTGG
ACAGCCGCAATCTACTATTCCGCTTGGAACCAGTGCATTGCACAAGCAATCAGACGTTTCCCAATTGATCTTTATCATATT
AACGACTACCATGGATCCATTGCCCCTCTTTATCTTCTACCTCAAACCATCCCTGTATGTCTGTCGCTCCACAATGCCGA
GTTCCAAGGACTGTGGCCTATGCGCACCCAGAAGGAGAGGGATGAAGTCTGTTCTGTTTTCAACCTTGATCTTGACACTG

```
CAAAGCGCTACGTCCAATTTGGCGAAGTTTTTAACATGCTTCATGCTGGAGCAAGCTACCTACGCGTGCATCAACAAGGG
TTTGGTGCAGTGGGCGTTTCTCGAAAGTACGGTAAACGTTCTTATGCCCGGTACCCAATCTTTTGGGGTCTGAAGAAGGT
TGGAAATCTACCGAACCCGGACCCTTCAGACACTGGCGAATGGAACAAGGAGTTACCAAAGGACAGCGAGATTCGGGTTG
ACCCGAACTACGAGGCTAGCAGAGGAGAGCTTAAGCGGCAGGCGCAGGAATGGGCAGGCTTGGATCAAAACCCTGATGCC
GACCTGTTGGTGTTTGTTGGAAGATGGTCTATGCAGAAGGGCGTGGACCTTATTGCTGATGTGATGCCTGCCGTTCTGGA
AGCACGTCCCAATGTTCAACTCATCTGTGTTGGTCCAGTCATTGATCTTTATGGTAAATTTGCTGCTCTTAAGCTGGATC
ATATGATGAGGTTATATCCTGGGCGTGTCTTCTCAAAGCCTGAGTTTACTGCACTCCCAGCATATATCTTCTCTGGCGCC
GAATTCGCCCTGATTCCATCTCGTGATGAACCTTTTGGTCTTGTTGCTGTCGAATTTGGTCGAAAGGGCGCTCTTGGTAT
TGGTGCTCGTGTTGGTGGTCTCGGCCAGATGCCTGGTTGGTGGTATAATATTGAGTCTACAACAACTTCCCATCTCTTGC
ATCAATTCAAGCTTGCGATTGGAAGCGCGCTTAACTCGAAGCCCCAAGTTCGTGCAAAGATGCGTGCACGCTCCGCAAAG
CAACGCTTTCCTGTTGCTCAGTGGGTGGAAGATTTGGAAATTCTGCAGACCACTGCTATGCGGATTCACAGCAAGGGACA
GGCAAAATCGAACGGTGGACCTCTCTCGCCTTCTGGTTACAATACACCAAGTGAAGTAATAACACCAAGTGGAATGATGA
CACCTACGATTGCATCGACTGGTACCACGACCCCAACGGGAATGCAGACGCCTCCAATCGCACACTCACGGGAAGGCAGT
TACACGAATCTCAGCGTCAATCGCGACAGTGCATACGGGCCCCAACAGCGCAACACAATTGTGTACAGCCGTGACCCAAG
CCCTGGAGGTAATGACGAACCTAGGTTAAGCCTTGGTCGGCAACTGTCACTTGGATTCAGGGCTGGACCAGGACATATTA
ATCTCCGTGGTCGTCGGCTTAAAAGAAGAAGCCAGATGACCAACGAGGAGAGTGGTACAGCGACCGAAGAAAGCAGTGAT
GACGATTATTTCCGCGGAGAGGAAGAAGTTACGATTACGAGGGAGCAAGCAGATGAAGGACGTCATCAACGCAATGCTCC
GAGGTCGCTTGCATCTCCTCCCAACTCTTACTTTGAAGAAGGCATAACATCCGGAAGGCCACCTTGGGCTCAACCTGGGA
ATCGACTCAGTAGTGCATCCGTTCTTTCTGTTGATTCTGTCGTCGGCGAAAAGAAAGACTATAAGCTGCAGAAAGTTGAT
CCATTCTTCACAGACGGTACTGGCGAATACTATCGAATGTTTGATCAGAGACTCGAAAAGCTCAACGGATCTAACTCTGA
ATCCCAGCTTTGTATAGAGGAGTATCTGATGAAGAGCGAAAAGAAGTGGTTTGACAAGTTCAGAGACGCAAGATTGGGGC
GCAACCAATCTCCCGCTTCTTCGATTTTCCAAACCAAGGGCGAAAACAACACACCTATGAGCTCAATCTCCCACGAGGAT
CTGGGTTCAAACGAAAGTGGCAGCGATCCACGCGCAGAAAAGGATGAGTTCCTTCTGGGACGAGACTATGTTCCCCCCTC
GGGCTTAAGGAAATGGATGCAAATTCGAATCTTTGGCTGGCCTGTGTATTCGTTTTTCCTAGGTCTCGGTCAGATCATTG
CGGCCAACTCATACCAAATTACCTTGCTTGCCGGTGAAAACGGCCAGACAGCTGAGAAGCTCTATGGTATTGCGACAGTA
TACCTTGTCACTTCAATCATCTGGTGGTTTTTCTTCCGCTTCTTCAAATCGGTGTTTGTCCTTTCCATACCTTGGTTCTT
ATACGGCGCATCGTTTGTCATCATTGGATTAGCACACTTTGAGTCAAATGGCTCCGCTCGTGGATGGATCCAGAATGTGG
GAAGCGGTGTTTACGCTGCGCTTCTTCAAGCGGATCACTGTTCTTCGCTCTCAATTTTGGCGATGAAAGCGGTGTTCAG
GTTAAAGACTGGGTTTTCCGGGCATGCCTCATCCAAGGAACCCAGCAAGCATATGTTATTGGACTGTGGTACTGGGGAAC
GACAATCTCTAGCGCTGTCGCCAATGGAGTTACCAACGTCAACGGCGGCATTGTCAACTCCTGGAAAATGACGTATGTTT
CACCTTTATCACTATGATTACAATTGCTAACGGCCTCTTCTAGCGCAATCTGCATGCCAATCGCTGCATTCCTCTGGGCC
ATTGGTCTGATAATCTTCTTCGGCCTGCCCAATTACTACCGCCAGTCACCTGGAAAAGTTCCATCATTCTACAAGTCTGT
CTTCCGGCGCAAGATCGTCCTGTGGAACTTCGTGGTAGTCATTTTGCAAAATTTCTTCCTCAGCGCACCTTATGGACGAA
ACTGGGCCTGTAAGTACATCAGACCTATACTCTCCAAGAAGCCACTAACTTATCGTGCCTCATACAGTCCTTTGGAGCTC
AAACCATGCCGAAGCCTGGCAAGTCGGCATCCTCGTCGTCGTCTTCTTCGGTGTCATCTGGGTAGCAGTGTTAACCCTAT
TTGGATATCTCTCGAAGCGCCATAGCTGGATTCTACCTGTATTTGCATGCGGTTTGGGAGCTCCACGTTGGGCCCAGATA
TGGTGGGGTGTCTCCGGAATGGGTCTCTTCCTTCCCTGGGCTGGCAGTTCTGTTAGCGGAGCACTCGCATCACGAAGTCT
ATGGCTCTGGCTCGGTATCCTTGATGCCTTACAGGGTCTCGGCTTCGGCATGATTCTTCTCCAGACCCTCACACGAGTAC
ATATAGCCTTCACCCTGCTTGCATCTCAAGTGCTGGGATCCATCGCGACAATCGTCGCCAGAGCATGTGCTCCAAATAAC
ATCGGTCCTGGACCAATCTCGCCGGATGTGACTGCCGGTGGCAGTTCCGTTGCAAACGCTTGGTTCTGGATCGCCTTATT
CTTCCAGCTCTTGATCTGGTAAGTCATCGATCCCCCTACAATCCATTTCACAGGCAGCAAAATGCTAACAAAGCCCCAGC
GCCGGATTCCTTCTGTTCTTCCGGAAAGAACAACTCACCAAGCCCTAA
```

FIG. 19
PUTATIVE AMINO ACID SEQUENCE OF AgsB protein OF *Aspergillus oryzae*

MKWAFSSAVLALFATTVKAWPYEESLSAYNLNENKSATNPAQYWGEWPDHKGKYFPSPDNWRFPVYTLFMDRFVNGDPTN
DNINGTLFEHDISSTQMRHGGDVAGLVDTLDYLQGMGIKAIYLAGTILMNQPWGSDGYSALDTTLLDQHFGDIATWRNAI
DEIHKRGMYVIFDNTIATMGDLIGFEGHLNDTTPFSVKEHKALWKSNRRYVDFDIGNDYNQTCDYPRFWYEDGYPVQQSM
TEGLVGCYDSDFDQYGDIEAFGVFPDWQRQLAKFASVQDRLREWHPSVRERLIRHSCMIIYQLDIDGFRYDKATQSTVDA
LGDMSMAYRECARAVGKENFFISGEITGGNTFGSIYLGRGRQPNQYPETAEKAMKMTNESESQYFLREAGHEAIDGAAFH
YSTYRALTRFLGMDGNLAAGYDVPVDWVDAWNLMLQSNDFINPNTCKFDPRHMFGATNQDVFRWPTVEKGVERQLLGLYI
TTLLLPGIPLLLWGEEQAFYILDATASNYIYGRQAMSPATAWRDHGCFSLDSSQYYQWPIQAGREGCHDPTAAYDHRDPA
HPVRNIIKHMYQLREDFPVLNDGYSVQKLSNLTEEVFYPGSNGTATETGLWSILRDVNADVQDLGSDAKNQPVWLVYHNT
NRTIDFKFNCKDNETALISPFATGTKVRNLFYPYDEHTLIDGPVKLGLNGSTELNGCLANMTLDAYEFRAYVPSARFTKP
RPMITQFTPGHDVPVRSTVAPNLDESVKIELYFSEEMDCDSVTKAISISSSTESKKVPTLDEKTVDCKGIPASNTSWTGQ
LPSVFMWAANLTGVYNGIHRVTVKNASSTNGNATTNAVDHFLFRIGQIDNPMVFTSANYSTSLLHEESNGTLFIQHHAAG
ADKWRYSTNWGTTFSEWKDYTGGNDTITELEWSGTKKQRWKGHHVRVEYWSKWTGSSDYVQEGDAGVHSNVPRRFPHIFF
NGPYNQYGYDGGLDNVVRQDSKDGLWKYHFTAEWPAQAQLNIWGMNPDGKPDQSWVLGDADNDSVLDRMPPSSLSATLIN
ITEHPPKPYLAWNIYINDATMKFQLFPVGHQNTQIAMFVLFWIIPVITGAACVYIFMKSFYKVKFNQIGVSEKATLIPLA
LRRKFKRNRGGDEERMNPLMRLANKSGFLQTNTAIGGAASGKRRMVLIATMEYDIEDWQIKIKIGGLGVMAQLMGKTLGH
QDLIWVVPCVGGVEYPVDKPAEPMNVTILGNSYEVQVQYHVLNNITYVLLDAPVFRQQSKSEPYPARMDDLNSAIYYSAW
NQCIAEACKRFPIDLYHINDYHGSLAPLYLLPDTVPACLSLHNAEFQGLWPMRTQKEKEEVCSVFNLDIDIVRRYVQFGE
VFNLLHSGASYLRVHQQGFGAVGVSKKYGKRSYARYPIFWGLRKVGNLPNPDPSDVGEWSKEKAIGNADEVHVDPDYEAG
RADLKRQAQEWAGLDVNPDADLMVFVGRWSMQKGVDLIADVMPAVLEARPNVQVICVGPVIDLYGKFAALKLDHMMKVYP
GRVFSRPEFTALPPYIFSGAEFALIPSRDEPFGLVAVEFGRKGALGIGARVGGLGQMPGWWYNVESTATSHLLYQFKLAI
DAALNSKQETRAMMRARSAKQRFPVAQWVEDLEILQTTAIQVHNKELVKHNGRPFTPTGTTTPSGLMTQPASPLGTPGMQ
TPLAHSRESSYSNLNRLSEYVTQPKTSYSRDPSPSGTEKPKSGLQRQLSLGVRSGPGHQSRRGRARQRDSIPEHEDTQEA
HGGAITDVEEESSDDDIVNHYADDEYTLTPAQVEEGRRLQAAQQQAGVRMPLSPGGRRYSQDSLHPRNVQPPSSPGTPPA
ASQSLLPPPRLLDPGSRLSSASVLSLDSVVGGKKDFKLQKVDPFFTDSTGEYYKIFDKKLDELNGSNSESQLCIEEYLIK
SEKEWFDKFRDARLGRTKSPTPSVYRDKHGASPIGSFYDDNGSRMSGSDGPHSNDSEDDEFLLGKDYVPPTGLKKWMQIR
IGDWPIYSLFLALGQIIAANSYQITLLTGEVGQTAEKLYGIATTYLITSILWWLVFRYFKSVVCLSAPWFLYGIAFIFIG
SAHFESNSFTRGWIQNVGSGFYAAASSSGSFFFALNFGDEGGAPVETWIFRACLIQGIQSAYVIALWYWGSTLSQAQSEG
LLTPTNNISNSWKISAICYPIAAALFGIGLLLTFGLPNYYRQTPGKVASFYKSVFRRKIVLWNFVAVILQNFFLSAPYGR
NWQFLWTSHHAHHWQIVILCVVFYGFVWAGFLFVVSRYFKSHSWFLPVFACGLGAPRWAQIWWGVSGIGYYLPWVTGGYT
GGALVSRSVWLWLGVLDSIQGLGFGIILLQTLTRMHMLFCLVCSQVLGSIATICARAFAPNNVGPGPVSPDPTFGGSAVA
NAWFWVALFCQLLVCAGYILFFRKEQLSKP

FIG. 20A

BASE SEQUENCE OF *agsB* gene OF *Aspergillus oryzae*

```
ATGAAGTGGGCTTTCTCCAGTGCGGTGCTGGCGCTTTTCGCAACAACAGTAAAAGCCTGGCCTTACGAAGAATCTCTCTC
CGCATACAACCTTAACGAAAACAAATCCGCGACCAACCCGGCTCAATATTGGGGAGAATGGCCGGACCACAAGGGGAAAT
ACTTCCCTTCTCCCGACAATTGGCGATTTCCCGTCTATACTCTGTTCATGGACCGCTTTGTCAACGGAGACCCTACGAAC
GACAACATCAATGGAACCCTCTTCGAGCACGATATCTCCTCGACACAAATGCGCCATGGTGGAGATGTGGCTGGTCTAGT
GGATACTTTGGATTATCTTCAGGGAATGGGTATCAAGGTTCGTCATTCGTTCAGGTTAATTACGTGGCATGCCATACTGA
GAATTCTTAGGCCATCTATCTCGCAGGAACCATCTTGATGAACCAGCCATGGGGCTCTGATGGTTATTCCGCTCTCGATA
CGACACTGCTCGATCAACATTTCGGTGACATTGCGACATGGCGTAATGCTATCGACGAGATTCATAAGCGCGGGATGTAT
GTCATCTTCGATAACACGATTGCTACGTAAGTCTCGCCGCATCCACGGTACATATGAGATGATTGTTAACGCTTGTATTC
AGGATGGGTGATCTCATCGGCTTCGAGGGCCATCTGAATGATACCACCCCGTTTTCGGTTAAGGAGCATAAAGCACTTTG
GAAGAGCAATCGTCGCTATGTGGATTTCGATATAGGAAACGACTATAACCAGACATGCGACTACCCCCGTTTCTGGTACG
AGGACGGTTATCCAGTTCAACAGTCTATGACTGAAGGCCTTGTTCGTTGTTATGACAGCGACTTTGATCAATATGGTGAT
ATTGAGGCTTTCGGCGTGTTCCCTGATTGGCAACGTCAGCTAGCAAAATTCGCCTCCGTCCAAGATCGTCTGCGAGAATG
GCACCCCTCGGTCCGGGAGCGGTTGATTCGTCATTCCTGTATGATTATTTACCAGTTGGATATCGACGGTTTCCGTTATG
ATAAGGCTACTCAGTCGACCGTGGATGCGCTAGGAGATATGTCGATGGCTTATCGCGAATGCGCCCGTGCCGTTGGCAAG
GAGAATTTCTTCATCTCCGGTGAAATTACTGGTGGTAACACTTTTGGTTCCATCTATTTGGGCCGAGGTAGACAGCCGAA
CCAGTATCCTGAGACGGCGGAGAAGGCCATGAAAATGACCAACGAGTCCGAGTCGCAATACTTCCTGCGTGAAGCTGGAC
ATGAGGCGATCGACGGTGCCGCCTTCCACTATTCGACATATCGTGCCCTGACTCGGTTCTTGGGTATGGACGGTAACTTG
GCCGCCGGTTACGATGTACCTGTGGATTGGGTCGATGCGTGGAATCTGATGTTGCAGTCGAACGACTTCATCAACCCTAA
CACAGGCAAGTTTGATCCCCGCCATATGTTCGGCGCGACCAACCAGGATGTTTCCGCTGGCCGACAGTCGAAAACGGGTG
TGGAAAGACAGTTGCTTGGGCTGTATATCACTACCTTACTTCTTCCGGGTATTCCCCTCCTCCTTTGGGGCGAGGAACAG
GCATTCTATATCTTGGATGCGACGGCATCTAACTATATCTATGGCCGTCAAGCAATGTCCCCCGCGACTGCGTGGAGAGA
CCACGGTTGCTTTTCCTTGGATTCCTCACAGTATTACCAGTGGCCTATTCAGGCCGGTCGTGAGGGTTGCCATGACCCAA
CTGCTGCGTACGATCATCGTGATCCGGCCCACCCGGTGCGCAACATTATCAAGCACATGTACCAGCTGCGCGAAGACTTC
CCTGTTCTGAATGATGGCTACTCCGTCCAGAAACTCTCGAACCTGACCGAGGAGGTCTTCTATCCGGGTTCCAACGGTAC
CGCTACAGAAACGGGTTTGTGGTCTATCCTACGTGATGTCAATGCCGATGTGCAGGACCTAGGCTCCGACGCGAAGAATC
AACCGGTGTGGCTCGTCTACCACAACACCAACCGTACAATTGACTTCAAGTTCAACTGCAAGGACAACGAGACTGCACTA
ATCTCGCCCTTCGCCACCGGCACCAAAGTTCGAAATCTGTTCTATCCCTATGACGAGCACACCTTGATTGATGGCCCCGT
CAAGCTTGGACTGAACGGATCTACCGAGCTCAATGGCTGCCTGGCCAACATGACATTGGACGCCTATGAGTTCCGCGCCT
ACGTCCCCAGTGCACGTTTCACTAAGCCTCGTCCAATGATCACCCAATTCACTCCCGGCCATGACGTCCCTGTTCGCTCC
ACGGTGGCTCCCAATCTGGATGAAAGCGTGAAGATTGAGCTCTATTTCTCCGAAGAGATGGACTGCGATTCTGTGACCAA
AGCGATTTCCATCAGCTCATCTACGGAATCTAAAAAGGTCCCGACGCTGGATGAGAAGACTGTAGACTGCAAGGGAATTC
CAGCAAGCAACACCTCCTGGACTGGGCAGCTTCCTAGCGTCTTCATGTGGGCTGCCAACCTGACGGGAGTGTATAACGGC
ATCCACCGAGTCACGGTTAAGAACGCTAGCAGTACTAATGGAAACGCGACAACAAACGCGGTCGACCACTTCCTCTTCCG
TATCGGACAAATCGATAACCCCATGGTCTTTACATCGGCCAACTATTCGACTAGTTTGCTCCACGAGGAATCGAATGGCA
CCCTATTCATCCAGCACCACGCAGCTGGTGCTGATAAGTGGCGTTATTCCACCAATTGGGGCACCACTTTCTCCGAGTGG
AAGGATTACACAGGTGGTAATGACACTATCACGGAGTTAGAATGGTCTGGAACCAAGAAACAGAGATGGAAGGGACACCA
TGTGCGGGTCGAGTACTGGAGCAAATGGACCGGTAGCAGCGATTACGTTCAGGAGGGCGATGCTGGAGTGCATTCGAATG
TGCCACGCCGCTTCCCCCATATCTTCTTCAACGGCCCTTACAATCAGTACGGATATGACGGTGGTCTTGATAACGTGGTG
AGGCAGGACTCCAAAGACGGACTCTGGAAATATCACTTCACGGCGGAGTGGCCGGCTCAAGCCCAGCTGAACATCTGGGG
CATGAATCCGGATGGAAAGCCTGATCAAAGCTGGGTGCTGGGTGATGCCGATAATGATTCCGTTCTGGATCGAATGCCAC
CCTCCTCTCTCTCTGCAACCTTGATTAACATCACCGAGCATCCGCCTAAGCCATATCTGGCTTGGAATATCTACATCAAC
GATGCGACCATGAAGTTCCAGCTCTTCCCTGTTGGGCACCAGAACACGCAGATCGCCATGTTCGTGCTCTTCTGGATCAT
CCCTGTCATCACCGGTGCAGCATGCGTCTACATTTTCATGAAGTCTTTCTATAAGGTCAAGTTCAACCAAATCGGTGTGA
GTGAAAAAGCCACATTGATCCCGTTGGCCTTGCGGAGAAAGTTCAAGAGGAATCGTGGTGGTGATGAGGAAAGGATGAAC
CCCTTGATGCGTCTGGCCAACAAGTCCGGTTTCCTGCAGACCAACACCGCTATTGGCGGCGCTGCTTCTGGCAAGCGACG
CATGGTTCTTATCGCGACAATGGAGTATGATATCGAGGATTGGCAGATTAAGATCAAGATTGGTGGTCTTGGTGTCATGG
CCCAGCTTATGGGGAAAACTCTCGGACATCAGGACCTGATCTGGGTTGTTCCCTGTGTCGGGGGAGTCGAATACCCAGTG
GATAAACCCGCTGAGCCCATGAATGTCACGATTCTTGGCAACTCTTATGAGGTTCAGGTCCAGTACCATGTCTTGAACAA
TATCACCTACGTTCTACTAGACGCCCCTGTGTTCCGCCAGCAATCGAAGTCCGAACCCTATCCAGCCCGTATGGATGACC
TCAACAGTGCTATCTACTACTCTGCCTGGAATCAGTGTATCGCTGAGGCCTGCAAGCGGTTCCCGATTGACCTGTACCAT
ATCAACGATTATCACGGTTCTCTAGCTCCGCTCTACCTTCTTCCCGATACAGTACCGGCTTGTCTTTCCCTTCACAACGC
TGAATTCCAGGGTCTCTGGCCAATGCGTACACAGAAAGAAAAGGAGGAGGTGTGCTCCGTCTTTAACCTAGATATTGATA
```

TTGTCAGACGTTATGTGCAGTTCGGTGAGGTTTTCAACTTGCTGCACTCAGGTGCTAGTTATCTTCGTGTTCACCAGCAG
GGTTTCGGTGCCGTCGGTGTGTCCAAGAAGTACGGAAAGCGGTCCTACGCCCGTTATCCCATCTTCTGGGGTTTGAGGAA
GGTCGGCAACTTGCCTAACCCTGATCCTTCGGATGTGGGAGAATGGAGTAAGGAAAAGGCTATTGGTAACGCTGACGAGG
TCCATGTGGATCCCGACTATGAGGCCGGCAGGGCAGACCTCAAACGCCAGGCTCAGGAATGGGCTGGTCTTGATGTCAAC
CCTGACGCTGATCTAATGGTGTTCGTTGGTCGTTGGTCCATGCAGAAAGGTGTCGATTTAATCGCCGATGTGATGCCAGC
TGTTCTTGAAGCTCGCCCTAACGTGCAGGTAATCTGTGTTGGACCTGTTATCGATCTTTATGGTAAATTCGCTGCCCTGA
AGTTGGACCACATGATGAAGGTTTACCCTGGACGTGTGTTCTCGAGACCTGAATTCACCGCTCTTCCGCCTTATATCTTC
TCTGGTGCTGAATTCGCGCTTATTCCTTCTCGTGACGAGCCCTTTGGTCTAGTCGCAGTCGAGTTCGGCCGTAAGGGAGC
CTTGGGTATCGGTGCCCGTGTCGGTGGTCTCGGTCAGATGCCTGGATGGTGGTATAACGTCGAATCTACTGCGACATCTC
ATCTTCTGTACCAGTTCAAGCTTGCCATCGACGCCGCACTTAACTCGAAACAAGAGACCAGAGCCATGATGCGTGCCCGT
TCTGCTAAACAGCGATTCCCCGTCGCCCAATGGGTCGAGGACTTGGAAATCCTGCAAACCACCGCAATCCAAGTACACAA
CAAGGAATTGGTCAAGCACAACGGTCGTCCGTTCACTCCGACTGGAACGACTACTCCTAGTGGCCTTATGACTCAACCTG
CGAGCCCTCTCGGGACCCCAGGAATGCAAACTCCTCTTGCTCATTCTAGGGAAAGCAGCTACTCGAACCTCAACCGTCTA
AGTGAATACGTTACCCAGCCAAAGACCAGCTACAGCAGAGATCCCAGCCCTAGCGGCACGGAGAAGCCGAAATCAGGACT
TCAGCGACAGCTTTCCCTTGGTGTTCGCTCTGGACCTGGTCATCAGAGCCGTCGTGGTCGCGCTCGCCAGCGTGACAGCA
TCCCAGAACACGAAGACACCCAGGAAGCTCACGGTGGCGCCATTACTGATGTTGAGGAAGAAAGCAGTGACGACGACATT
GTCAACCATTACGCGGATGACGAGTATACTCTTACACCTGCCCAAGTCGAAGAAGGCCGTAGGTTACAGGCCGCCCAGCA
ACAGGCTGGTGTGCGCATGCCGTTGAGTCCAGGTGGTAGACGCTACAGCCAAGACTCGTTGCATCCGAGAAATGTCCAGC
CTCCTTCGAGTCCCGGAACACCCCAGCCGCTTCCCAGAGTCTCCTTCCTCCCCCTAGGCTCCTCGATCCCGGCAGTCGT
CTCAGTAGCGCATCCGTTCTCTCACTTGACTCCGTTGTCGGTGGCAAGAAGGACTTCAAGCTGCAAAAGGTTGATCCGTT
CTTCACTGATAGCACCGGCGAGTATTACAAGATCTTTGATAAGAAGCTTGATGAACTCAATGGATCGAACTCGGAGTCGC
AACTGTGTATCGAAGAATACTTGATCAAGAGTGAAAAGGAATGGTTCGACAAGTTCCGTGACGCTAGACTTGGTCGCACT
AAATCGCCAACTCCCTCAGTCTATCGTGATAAGCACGGCGCCTTCCCCTATCGGCTCGTTCTACGATGATAACGGCTCCCG
TATGAGTGGTAGCGATGGCCCTCACTCCAATGACAGTGAAGACGACGAGTTCCTCCTCGGAAAGGACTATGTCCCTCCCA
CCGGTCTCAAGAAGTGGATGCAGATTCGCATCGGTGACTGGCCTATCTACTCCTTGTTCCTCGCTTTAGGCCAAATCATT
GCTGCCAACTCGTACCAGATCACATTGCTCACGGGCGAAGTCGGTCAAACTGCCGAGAAACTGTACGGAATTGCAACCAC
GTATTTGATCACGTCTATTCTCTGGTGGCTTGTGTTCCGCTACTTCAAATCCGTCGTCTGTCTGTCGCGCCATGGTTCT
TGTACGGTATCGCCTTCATCTTCATTGGATCCGCCCATTTTGAGAGCAACTCTTTCACTCGGGGATGGATTCAAAATGTC
GGTAGTGGGTTCTACGCCGCGGCCTCGTCTAGTGGTTCTTTCTTCTTCGCGCTAAACTTCGGTGATGAAGGTGGTGCACC
TGTGGAAACATGGATCTTCCGTGCATGTCTCATTCAGGGTATCCAGTCCGCCTATGTTATTGCTCTCTGGTACTGGGGTT
CAACCCTGTCACAGGCACAAAGTGAGGGTCTCTTGACTCCTACAAACAATATCTCCAATTCTTGGAAGATTAGGTAGGTT
ATATTGATCTCTTTGGTTAATTTCACTAGCTAACTAATACTTTCACAGTGCCATCTGTTACCCCATTGCCGCGGCCCTTT
TCGGAATTGGTTTGCTCTTGACATTCGGCCTGCCCAACTATTACCGTCAAACCCCTGGCAAGGTCGCTTCCTTCTACAAA
TCCGTGTTCCGTCGTAAGATCGTCCTCTGGAACTTTGTCGCGGTCATCCTTCAGAACTTCTTCCTCAGCGCCCCTACGG
CCGCAACTGGCAGTGTAAGTTGACCCCTGTATAACGGTTTCCATCATATCAGACCAAACTAACTGTGTCTCTTTGCAGTC
CTCTGGACATCCCACCACGCACATCACTGGCAAATCGTCATCCTCTGTGTTGTTTTCTACGGCTTCGTATGGGCAGGCTT
CCTATTCGTCGTCAGTCGCTACTTCAAATCACACAGCTGGTTCCTCCCCGTGTTCGCCTGTGGCCTCGGAGCTCCCCGCT
GGGCACAAATCTGGTGGGGTGTGTCTGGCATTGGCTACTACCTCCCTTGGGTGACAGGAGGATATACCGGCGGCGCGCTC
GTCTCCCGAAGTGTCTGGCTCTGGCTCGGCGTGCTGGACTCGATCCAGGGTCTCGGCTTCGGTATCATCCTCTTGCAAAC
CCTGACTCGCATGCACATGCTTTTCTGTCTTGTTTGTTCTCAAGTCCTTGGTTCTATCGCTACGATCTGCGCGAGAGCCT
TCGCCCCTAATAATGTGGGCCCAGGGCCCGGTTTCGCCTGATCCTACCTTTGGTGGGAGTGCCGGTGCGAATGCCTGGTTC
TGGGTTGCTCTGTTTTGTCAGTTGTTGGTCTGGTAAGTTATTCACATCTTATGAACTTTGTTATATACAACGATCGCTAA
CGTGTGATGATTACAGTGCCGGTTACATCCTCTTCTTCCGGAAAGAACAGCTGTCAAAGCCTTAA

FIG. 21

PUTATIVE AMINO ACID SEQUENCE OF AgsC protein OF *Aspergillus oryzae*

MFLTVMQRSAILILSLLSATALSWPYTESLVDYNLNENKTAEAPIDYWGEWPDHEYHPSPDNWRFPIYTIFLDRIANGDP
KNDDINGTAFEHVVGSNQMRHGGDLVGLIDTLDYIRGMGFKGIYFAGTYLMNLPWAYDGYSPVDTTLLDMHHGTLEDWRR
TITEIHKRDMYVIVDNTLATMSNLIGFKGHLNDSADFRADEYEVQWISDRQYADFKFGNEYNETCNFPKFWNETGYPLTS
GGVEELKGCYNSDFDQFGELEAFGNFPDWKRQLTKFASVQDRLREWHKPIRDVITKHSCIQIASLDIDGFRFDKAVQTTL
EPLSEITAVYRECAKKYGKHNFFLPGEITSGNTFGSLYLGRGRQPDQQPESADAGVKLKNSSDGYFLRDDGYQALDSAAF
HYTIYRSMTRFLGMDGNLVAGFDLPTDFIEAWNGMLVSNDFLNAYTGEVDPRHMFGVSNQDNFRWPAIVNGTEKYLLGLY
IVTLELPGIPLILWGEEQAMYVFESTASNYLFGRQPMTYQTAWWTHGCMTLNTSKFYDFPNEKGLHGCEDITVTYDQRNP
AHPLRNIMKRMFEIREQYPVANDGFYLQTLSQLTKDVYLPGSTDTPTVTGLWSVLRSYFPGVQKEASKNSQNLWLVYHNA
NKTETYGGDCKKKDTALLSPFKSGTKLKNLFYPYDELTLEDGPGEIAVHNSTESYGCIRSMKLLPWEYRAYIEAENFVEP
GPTVTEFVPGHDARLLSTDDSGQTVDIQLGYSKEMDCDKIADAISLNSTTVKGVTASLDTSSVSCNKISPRTSSDNFVGE
VPTVWTWSAKLKNVHHGIHQLTVKNVSTTSGVHTDAVDQFLFRVGSQNNPLLSPLSNYSTSLVQKSDNGSFYIQHDAAGA
DKFRYSTDFGLNWSNWTTYTGDNTLVDFPEWTGTDAQKWKGTHIRVQYFSRLTGSSDYIQEGDHGWEKGVARRFPNLFWN
GPFNQYGYDAGLDNKMRYDTKDHRWKYDFVYEWPAIGQMSVWGMLKDGRPDVTEVYGDVDNSSVVQKLPPSYLSSNVINI
TKLPPFPHLGWTITLNDANLRYEMLPVGSGWAQLVLYILLWVLPILMGFAGIFIFIRTFYRVKLNTDGDVAKEDKLPLLF
WRRVREKFSGDDESDKSISDKDIPTDIAIAGAPEQRRTVLIATMEYNIEDWKVKVKIGGLGVMAQLMSQHLKHQNLIWVV
PCVGDIEYPQDTPSEPFVVTILDKPYFINVQYHIVDNITYVLLDAPVFRQQTKAEPYPPRMDDLDSAIYYSAWNQCIAET
IKRFPSIDLYHINDFHGCLAPLYLLPTRTIPVCLSLHNAEFQGLWPLRNPQEKKEVCSVFNLPIETATKYSQFGNVFNLL
HTGASYVRFYQRGFGAVGVSKKYGKRSWARYPIFWSLEKIGSLPNPDPSDTGDMTNNADAEVPIQSYEERINDKLQAQKW
AGLNEDRDADLLVFVGRWSKQKGVDLIADVMPAILSARPHVQLICVGPIVDLYGRLAATKLERIMEMFPGRVFSKPEFTV
LPPYVFSGADFALIPSRDEPFGLVAVEFGRKGALGIGSRIGGLGQMPGWWYTVESDATRHLLHQLKTAIKQALDSSQDAR
EEMRANSVRQHFPVLEWIQKLEALQRTAIQIHHTKNKNTVTGPMPESQNYWETQSVRMSTLGLPGPTQSVTEGLDTPPGR
LLTPGQSRFAELQLEGADGNRNSSLGRKLSLGRRSGPGQDRKRPGKSPPRESQILGEDLEGENTDAEEEGTTTPQVNYIS
PEEAMAAVNNTLGTQDIGMAHTNNSTHSLAGPQGSTYMSVPGSPNNMSRASSPMPGTPGLPQYPFQFALGSGGNTPFTHS
RNVSMLSLPSVVADHNQPVFELQKVDPTFTDSTRHFTRRFEEILNNLNKKNSMTDCCIETYLMKSERKFYDMYNDAQLKK
QPDDRAVSDSNSDTQDNRASYATVTGGSDSNDPDEIDLWLSRLGYKRPIAIQRFMRRRLGKWPVYALFLGLGQIIATNSA
QMTLLVGQVGETATKLYIIATIYCISSICWWLLFYRFPSVIVLTLPWFIYCMAFIIIGVSPFALTSLGRAWAQNVAAGVY
SAASSSGSLFFALNFGDQGAVPIKDWMFRASLIQGIQQLYTVALWYWSSKVTEAEVGGVSTAALSSWRLTAVVMPIAAVC
FIVGVLLALGLPKYYRQSPGRILFFYTSLFRRRIVLWFFFMVIVQNWFLSAAFGRNWSFLWSSQHAKAWEVVILVIFFFV
VLWVIILIIFRALSKEHSWILPVFGLSLGAPRWAQTWWGTSNIGYYLPWAGSLTSGALVSRCVWLWLGVLDEIQQVGLGM
ILLQTLTRVHVCFVLLAAQALGSIATICARGFAPNKLGPAGISPNVGTSLDTVGNAWFWIALFFQLLASWGFLLFYRREQ
LNRP

FIG. 22A

BASE SEQUENCE OF *agsC* gene OF *Aspergillus Oryzae*

```
ATGTTCCTCACGGTGATGCAGCGCTCAGCGATCCTTATCCTGTCGTTACTGAGCGCTACCGCCTTAAGCTGGCCATACAC
TGAGTCGCTCGTTGACTATAACCTGAATGAAAATAAAACCGCCGAAGCGCCGATTGATTATTGGGGAGAGTGGCCGGATC
ATGAATATCACCCGTCGCCCGATAACTGGCGCTTTCCGATCTATACCATCTTTTTGGACCGCATCGCTAACGGTGACCCG
AAGAATGATGATATCAATGGCACCGCCTTTGAGCATGTGGTTGGCTCGAATCAAATGCGCCACGGGGGCGATTTGGTTGG
TCTAATTGATACGCTGGATTATATTAGGGGCATGGGTTTCAAGGTGTGTTGAGCCGATTGTGATCCGATCTTGGTGCTTA
CTCTGGTAGGGCATTTACTTCGCTGGAACGTACTTGATGAACCTTCCCTGGGCCTACGATGGCTACTCACCGGTTGATAC
CACTTTGCTCGACATGCACCATGGCACACTCGAGGATTGGAGACGGACCATCACTGAGATCCACAAACGAGATATGTATG
TGATCGTGGATAATACACTGGCAACGTAAGTACATATCCCAGGTGTCTCAGATCAACACTGGTTGACGAGTATATGCAGA
ATGAGCAACCTTATTGGTTTCAAAGGACATCTCAACGATTCAGCCGATTTTCGAGCAGATGAATATGAAGTGCAGTGGAT
CTCAGATAGACAGTACGCCGGACTTCAAATTCGGAAATGAGTACAACGAGACCTGCAACTTCCCGAAGTTTTGGAATGAGA
CTGGGTATCCGTTGACATCAGGTGGTGTTGAGGAGCTGAAAGGGTGCTATAATAGCCGATTTCGATCAATTTGGAGAGCTG
GAGGCGTTCGGTAACTTTCCAGACTGGAAGCGCCAGCTTACCAAGTTCGCCTCGGTGCAAGATCGTCTGCGTGAATGGCA
CAAGCCTATTCGTGATGTCATCACTAAGCATTCTTGCATTCAGATCGCTAGTCTAGATATCGATGGTTTCCGTTTCGATA
AAGCCGTTCAGACAACCCTCGAGCCCCTAAGTGAAATAACCGCCGTCTACCGTGAGTGTGCGAAGAAATATGGCAAGCAT
AACTTTTTCCTTCCCGGTGAGATCACATCAGGAAATACCTTTGGCAGTCTTTACCTTGGACGCGGTCGTCAGCCAGATCA
GCAGCCTGAATCTGCAGATGCTGGTGTTAAGTTGAAGAATAGTTCGGACGGATATTTTCTCAGAGACGATGGATACCAGG
CGTTGGACTCAGCCGCGTTTCACTACACGATCTACCGTTCGATGACTCGTTTCCTGGGAATGGATGGTAATCTAGTGGCT
GGCTTTGACTTGCCTACTGATTTTATCGAGGCCTGGAATGGGATGCTCGTCAGCAACGACTTCCTCAATGCATACACGGG
TGAAGTAGACCCGAGGCACATGTTTGGTGTCTCAAACCAGGACAACTTTCGCTGGCCAGCAATCGTAAATGGCACCGAGA
AATATCTTCTGGGTCTTTATATCGTCACCTTGGAGCTCCCTGGAATTCCTCTGATCCTATGGGCGAAGAGCAGGCGATG
TATGTTTTTGAATCTACTGCTTCTAACTACCTGTTCGGCCGGCAGCCAATGACGTATCAGACGGCATGGTGGACACATGG
ATGCATGACTTTGAATACATCCAAATTCTACGATTTCCCTAATGAGAAGGGACTACACGGCTGCGAGGATATCACCGTTA
CGTATGATCAGCGGAATCCGGCACACCCTCTGCGCAATATCATGAAGCGCATGTTCGAAATTCGGGAGCAGTATCCGGTA
GCAAATGATGGGTTTTATCTTCAAACGCTTTCTCAGCTGACAAAGGATGTGTACCTTCCTGGTTCAACGGACACGCCGAC
TGTGACTGGTCTATGGTCGGTTCTGCGGAGCTACTTCCCAGGCGTCCAGAAGGAGGCAAGCAAGAACAGTCAGAACCTTT
GGCTTGTGTATCATAATGCTAACAAAACTGAAACCTACGGTGGTGACTGCAAAAAGAAAGATACCGCCTTGCTGTCGCCT
TTCAAGTCGGGAACTAAGCTGAAGAATCTCTTCTATCCGTACGATGAGCTCACTTTAGAAGATGGTCCGGGCGAAATCGC
AGTCCACAATAGCACTGAGAGCTATGGATGCCATCCGCAGTATGAAATTGCTTCCATGGGAATACCGTGCCTACATAGAGG
CCGAGAACTTCGTTGAGCCCGGCCCTACTGTTACTGAGTTCGTTCCTGGGCACGACGCCCGATTGTTGTCTACGGATGAC
AGTGGCCAAACTGTCGACATCCAGCTCGGATATTCAAAAGAGATGGACTGTGACAAGATCGCCGATGCCATCTCTTTGAA
CTCAACGACAGTGAAGGGAGTTACAGCTTCCCTTGACACATCTAGCGTGTCTTGCAACAAAATCTCCCCAAGGACAAGCA
GTGATAACTTTGTTGGGGAGGTTCCAACCGTTTGGACATGGTCTGCCAAGCTGAAAAATGTCCACCACGGAATCCATCAG
CTGACAGTTAAGAACGTTTCCACGACGTCTGGAGTTCATACCGATGCGGTTGACCAGTTCTTATTCCGTGTCGGAAGTCA
AAACAATCCCCTTTTATCCCCACTGTCCAATTATTCCACCAGTCTTGTGCAGAAATCCGACAACGGCAGCTTCTATATCC
AGCATGACGCCGCTGGTGCTGATAAATTTCGCTACTCGACTGATTTTGGCCTTAACTGGTCCAACTGGACAACGTATACC
GGTGACAACACCCTAGTCGACTTCCCAGAGTGGACCGGAACAGACGCTCAGAAGTGGAAGGGAACTCATATTCGCGTACA
GTACTTTTCAAGGCTCACCGGCAGTAGTGATTACATTCAGGAAGGTGATCATGGCTGGGAAAAAGGTGTTGCTCGAAGAT
TTCCTAACCTCTTTTGGAACGGTCCGTTCAATCAATATGGTTACGATGCGGGACTGGATAACAAGATGAGATACGATACC
AAGGATCATCGTTGGAAGTACGATTTTGTCTACGAGTGGCCGGCCATTGGACAAATGAGTGTCTCGGGAATGTTAAAGGA
TGGGCGGCCCGACGTTACAGAGGTGTATGGTGATGTCGACAACTCATCTCTGTAGTTCAGAAACTTCCTCCGTCTTACCTAT
CGTCCAACGTGATCAATATCACAAAGCTGCCTCCATTCCCGCACCTCGGCTGGACCATCACGCTCAATGACGCCAACTTG
AGATATGAGATGCTTCCGGTCGGATCTGGATGGGCCCAGCTCGTGCTATACATTCTTCTCTGGGTGCTTCCAATTCTCAT
GGGATTTGCTGGTATCTTCATCTTCATCAGGACATTCTACCGTGTTAAACTCAATACCGATGGCGATGTGGCCAAAGAAG
ATAAGCTACCGCTCCTGTTTTGGCGGAGGGTCAGAGAAAAGTTCTCCGGCGACGACGAGTCGGATAAGTCGATATCAGAT
AAGGATATACCGACAGACATTGCTATCGCGGGAGCCCCTGAGCAACGTCGTACAGTATTGATCGCCACCATGGAATACAA
CATCGAAGACTGGAAGGTCAAGGTCAAGATCGGCGGTCTAGGCGTCATGGCACAACTCATGTCTCAGCATCTGAAGCATC
AAAACTTGATCTGGGTTGTTCCTTGCGTTGGTGACATTGAATATCCTCAGGACACGCCATCCGAGCCTTTCGTGGTCACT
ATCCTGGACAAGCCATATTTTATCAATGTGCAATATCATATAGTTGATAACATCACCTATGTCCTGCTCGACGCTCCAGT
TTTCCGCCAACAGACCAAAGCAGAGCCATATCCTCCTCGCATGGATGATCTTGACAGTGCAATCTACTATTCGGCATGGA
ACCAATGTATCCAGAGACGATCAAACGATTCCCGTCAATCGATCTCTATCATATCAACGATTTCCATGGTTGTTTAGCA
CCACTGTATTTGCTTCCCACGCGTACCATCCCGGTGTGCCTGTCCTTACATAATGCTGAATTCCAGGGTCTTTGGCCCCT
GAGAAACCCCCAGGAAAAGAAGGAAGTCTGTTCGGTCTTCAACCTTCCCATCGAAACTGCAACCAAGTACAGTCAATTTG
```

```
GAAACGTCTTCAACCTTCTTCACACTGGTGCGAGCTATGTGCGATTCTACCAACGCGGTTTCGGCGCAGTAGGTGTGTCC
AAAAAGTATGGAAAGCGCTCATGGGCTAGATACCCGATTTTCTGGAGTCTTGAAAAGATTGGCAGTCTTCCAAACCCAGA
CCCCTCCGACACAGGGGACATGACAAATAACGCAGACGCCGAGGTTCCAATCCAGTCCTACGAAGAACGAATCAATGATA
AGCTACAGGCCCAGAAGTGGGCTGGTTTGAATGAAGATCGTGATGCTGACCTACTTGTGTTCGTCGGGCGATGGTCGAAG
CAGAAGGGAGTGGATTTGATTGCAGATGTCATGCCAGCGATATTATCCGCCAGACCCCACGTGCAATTGATCTGCGTTGG
ACCTATCGTTGATCTCTATGGTAGACTGGCTGCTACAAAGCTAGAGCGCATCATGGAAATGTTCCCTGGTCGCGTCTTCT
CTAAGCCAGAGTTCACCGTTTTGCCTCCATACGTATTTTCTGGTGCCGACTTCGCTCTGATTCCCTCCAGAGACGAACCA
TTTGGGTTAGTCGCTGTAGAGTTCGGCCGTAAGGGTGCACTGGGAATCGGTTCTCGCATTGGAGGTTTAGGCCAGATGCC
AGGTTGGTGGTACACCGTGGAATCCGACGCAACCCGCCATCTTCTGCATCAGTTGAAGACCGCTATCAAACAAGCGTTGG
ACTCATCACAGGACGCTCGTGAGGAGATGCGCGCCAATTCCGTCAGGCAACATTTCCCCGTTCTTGAATGGATTCAGAAA
CTCGAAGCCTTGCAACGAACAGCGATCCAAATCCATCACACCAAGAACAAGAACACCGTGACAGGCCCGATGCCAGAGTC
GCAGAACTATTGGGAGACTCAAAGCGTACGAATGTCTACGCTGGGCCTTCCAGGACCTACCCAGTCGGTGACAGAGGGTT
TGGATACACCGCCAGGAAGGCTTTTGACGCCCGGCCAGTCTCGATTTGCAGAATTGCAATTGGAGGGAGCTGATGGCAAC
AGGAACAGCAGCCTGGGTCGCAAACTCTCGCTCGGTCGGCGATCTGGACCTGGTCAGGACAGAAAACGTCCCGGCAAGAG
CCCGCCGCGCAGAGCCAGATCCTAGGAGAGGATTTGGAAGGTGAGAACACGGATGCCGAAGAAGAGGGCACCACTACGC
CGCAGGTGAACTATATTTCACCTGAAGAAGCTATGGCTGCAGTTAACAACACTTTGGGAACTCAAGATATCGGAATGGCA
CACACGAACAATAGTACTCACTCGCTCGCTGGTCCTCAAGGATCTACTTACATGTCCGTGCCAGGCTCACCAAACAACAT
GTCACGGGCCTCCTCTCCAATGCCAGGAACCCCGGGGCTGCCCCAATACCCATTCCAGTTCGCATTGGGTTCTGGCGGAA
ATACTCCTTTCACTCACTCCCGCAATGTGTCCATGCTTTCCTTGCCTTCAGTCGTGGCGGACCACAACCAGCCGGTTTTT
GAGCTGCAAAAGGTTGATCCGACCTTTACAGACAGCACACGCCACTTCACGCGACGCTTCGAAGAGATTCTCAACAACCT
GAACAAGAAGAACTCGATGACAGACTGCTGTATCGAGACGTACCTAATGAAGAGCGAGCGTAAATTCTACGACATGTACA
ACGATGCACAATTAAAGAAACAGCCCGATGATCGTGCAGTGTCTGATTCGAATTCAGACACTCAAGATAACCGCGCCTCG
TACGCCACTGTCACTGGAGGTTCGGACTCGAATGATCCGGATGAGATTGATTTATGGCTCTCTCGACTGGGGTATAAACG
ACCGATTGCTATTCAAAGATTCATGAGAAGGCGTCTTGGCAAATGGCCTGTCTACGCTCTATTCCTGGGTCTTGGACAAA
TCATCGCGACCAACTCCGCTCAAATGACCCTGTTGGTCGGTCAGGTAGGAGAAACAGCAACCAAGTTGTACATTATCGCC
ACGATCTACTGCATTTCCTCTATCTGTTGGTGGCTCCTCTTCTATCGATTCCCGTCAGTAATCGTCCTCACTCTCCCCTG
GTTCATTTACTGCATGGCATTTATCATCATTGGCGTCTCTCCATTCGCTCTCACATCTCTCGGTCGAGCCTGGGCCCAGA
ACGTCGCTGCAGGTGTGTATTCCGCCGCATCATCTAGCGGCTCGTTATTCTTCGCCCTCAACTTCGGTGATCAGGGTGCC
GTTCCTATAAAGGATTGGATGTTCCCGCGCAAGTCTCATCCAGGGAATCCAGCAGCTCTACACCGTCGCCTTATGGTACTG
GAGCTCGAAGGTGACCGAAGCAGAGGTGGGAGGCGTGTCCACCGCGGCTCTAAGCTCATGGAGACTCACAGCTGTGGTGA
TGCCCATCGCCGCAGTATGTTTCATAGTCGGCGTGCTTCTCGCGCTCGGCCTACCAAAATACTACCGCCAATCCCCCGGT
AGGATCCTCTTCTTCTACACATCCCTCTTCCGCCGCCGTATTGTCCTCTGGTTCTTCTTCATGGTAATAGTCCAGAACTG
GTTCCTCTCCGCAGCATTTGGTCGCAATTGGTCATTCCTCTGGTCCTCCCAACACGCTAAGGCATGGGAGGTCGTCATCC
TAGTCATCTTTTTCTTCGTCGTCCTCTGGGTAATCATCCTCATCATATTCCGCGCCCTATCCAAGGAACACAGCTGGATT
CTACCCGTATTTGGTCTGAGTCTCGGCGCACCGCGCTGGGCCCAAACATGGTGGGAACGTCCAACATAGGCTACTACCT
GCCATGGGCGGGAAGTCTGACATCCGGTGCCCTCGTGTCGAGATGCGTCTGGCTCTGGCTCGGTGTGCTTGACGAAATCC
AGCAAGTCGGCCTGGGTATGATCCTCCTACAGACACTGACCAGAGTCCACGTGTGCTTCGTTCTGTTGGCCGCACAGGCT
CTCGGATCCATCGCTACGATCTGCGCCCGTGGATTCGCGCCGAATAAGCTCGGGCCCGCGGGAATCTCGCCGAACGTGGG
AACGTCTCTAGATACAGTTGGAAATGCGTGGTTCTGGATCGCGCTCTTCTTCCAGCTTCTGGCTAGGTAAGGCTTCTGTA
TTCCCGGCTTCAATGGATTCAATACTAATGTGGTTCATAGTTGGGGCTTCCTTTTGTTCTATCGTCGTGAGCAGCTTAAT
AGGCCTTAA
```

METHOD FOR MANUFACTURING USEFUL SUBSTANCE IN WHICH HIGH-DENSITY CULTURED STRAIN OF FILAMENTOUS FUNGI IS USED

CROSS-REFERENCE TO RELATED APPLICATION

This application claims priority from Japanese Patent Application No. 2012-247276, filed on Nov. 9, 2012, the entire disclosure of which is incorporated herein by reference.

The present invention relates to a method of producing a useful substance using a filamentous fungus.

TECHNICAL FIELD

Background Art

A filamentous fungus is a collective name for fungi constructed of tubular cells called hyphae, and is used for fermentative production of: low-molecular-weight compounds, for example, chemical products such as an organic acid, a pigment, and an agricultural chemical bulk, and pharmaceutical products such as penicillin and statins; and industrial enzymes such as amylase, cellulase, protease, and lipase.

For example, in Patent Literature 1, there is a disclosure of a method of producing cellulase, including the steps of: producing a disaccharide-containing solution by adding thermophilic fungus-derived β-glucosidase to a glucose-containing solution and subjecting the mixture to a condensation reaction; and producing cellulase by culturing a filamentous fungus using a medium containing the disaccharide-containing solution.

In addition, in Patent Literature 2, there is a disclosure of a method of producing phospholipase, including a step of processing a fungal peptide to truncate a peptide from the C-terminus and/or a peptide from the N-terminus, to thereby produce a core peptide formed of a specific amino acid sequence having phospholipase activity.

In addition, in Patent Literatures 3 to 7, with a view to increasing efficiency of substance production using the filamentous fungus, there is a disclosure of an expression vector constructed so that the filamentous fungus functions as a host, there is also a disclosure of a method involving preparing a transformant by introducing, into the filamentous fungus, a plasmid in which a gene encoding a homologous or heterologous protein is functionally linked to the expression vector, and there is also a disclosure that utilization of the transformant contributes to increased production of enzymes such as amylase and cellulase and low-molecular-weight compounds such as penicillin.

As described above, the filamentous fungus has an advantage of being able to produce a wide variety of useful substances. However, the filamentous fungus causes a problem in that the filamentous fungus cannot be cultured at a high density because of entanglement of hyphae and aggregation of cells in its liquid culture step, a problem in that a production amount of a useful substance lowers, and a problem in that a production step of a useful substance becomes complicated. Accordingly, attempts have been made to solve the problems from various viewpoints (e.g., Patent Literatures 8 and 9).

CITATION LIST

Patent Literature

[PTL 1] JP 2010-227032 A
[PTL 2] JP 2010-172343 A
[PTL 3] JP 2001-46078 A
[PTL 4] JP 2005-52116 A
[PTL 5] JP 2009-118783 A
[PTL 6] JP 11-506025 A
[PTL 7] JP 2007-508022 A
[PTL 8] JP 2002-218970 A
[PTL 9] JP 2010-227031 A
[PTL 10] JP 2010-107126 A
[PTL 11] JP 2010-220590 A

Non Patent Literature

[NPL 1] Hogan, L. H., et al (1994) Altered expression of surface α-1,3-glucan in genetically related strains of *Blastomyces dermatitidis* that differ in virulence. Infect. Immun. 62:3543-3546.
[NPL 2] Rappleye, C. A., et al (2004) RNA interference in *Histoplasma capsulatumdemonstrates* a role for a-(1,3)-glucan in virulence. Mol. Microbiol. 53: 153-165.
[NPL 3] Beauvais, A., et al (2005) Two α(1-3) Glucan Synthases with Different Functions in *Aspergillus fumigates*. Appl. Environ. Microbiol. 71: 1531-1538.
[NPL 4] Maubon, D., et al (2006) AGS3, an α(1-3)glucan synthase gene family member of *Aspergillus fumigatus*, modulates mycelium growth in the lung of experimentally infected mice. Fungal Genet. Biol. 43:366-375.
[NPL 5] Henry C., et al (2011) α1,3 glucansare dispensable in *Aspergillus fumigatus*. Eukariot. Cell 11: 26-29

SUMMARY OF INVENTION

Technical Problem

An object of the present invention is to culture a filamentous fungus at a high density, thereby enabling mass production of a useful substance.

Solution to Problem

The inventors of the present invention have made intensive investigations under the above-mentioned circumstances. As a result, the inventors have found that in the case of using a mutant strain of a filamentous fungus with no expression of α-1,3-glucan, aggregation of cells during culture is significantly suppressed and the cells are homogeneously dispersed in a medium, thereby enabling the filamentous fungus to be cultured at a high density. The inventors have also found that in the case of using such mutant strain, the production amount of a useful substance per unit volume can be increased. The present invention is based on such novel findings.

It is known that α-1,3-glucan is one of the major cell wall constituents in a filamentous fungus, and is involved in pathogenicity expression. In research to investigate a pathogenicity expression mechanism based on a relationship between a fluctuation in α-1,3-glucan in a cell wall and pathogenicity expression, an attempt has been made to elucidate, by changing an α-1,3-glucan amount in a cell wall through the preparation of a glucan synthase gene disruption strain or the suppression of glucan synthase gene expression, a pathogenicity expression mechanism based on a relationship between the fluctuation and pathogenicity expression (e.g., Non Patent Literatures 1 to 4). In addition, there have been made a technical proposal concerning a medicament using α-1,3-glucan as a target molecule (Patent Literature 10), a technical proposal of using a fluctuation in expression amount of glucan synthase gene as an indicator in a method of screening a drug candidate using α-1,3-glucan as a target (Patent Literature 11), and the like. However, there has been no concept of utilizing a fungus with no expression of α-1,3-glucan in increased production of a substance, and the technology development thereof has also not been performed.

Thus, the present invention provides the following items.

Item 1. A method of producing a substance, including the steps of:
culturing a mutant filamentous fungus with no expression of α-1,3-glucan to allow the filamentous fungus to produce a substance;
and collecting the resulting substance.

Item 2. A method according to Item 1, in which the mutant filamentous fungus is deficient in at least one α-1,3-glucan synthase ags gene.

Item 3. A method according to Item 1 or 2, in which the filamentous fungus belongs to a genus *Aspergillus*, a genus *Penicillium*, a genus *Trichoderma*, a genus *Cephalosporiurn*, or a genus *Acremonium*.

Item 4. A method according to Item 3, in which the filamentous fungus includes *Aspergillus nidulans*, *Aspergillus oryzae*, *Aspergillus niger*, or *Aspergillus fumigatus*.

Advantageous Effects of Invention

According to the method of the present invention, the entanglement of hyphae and the aggregation of cells are suppressed in the liquid culture of the filamentous fungus, and hence the filamentous fungus can be cultured at a high density. Therefore, the production amount of a useful substance per unit volume can be drastically increased.

BRIEF DESCRIPTION OF DRAWINGS

FIG. 2 provides graphs showing dry cell weights after culture in Example 1 and Comparative Example 1.

FIG. 3 provides photographs showing flasks after culture in Example 1 and Comparative Example 1.

FIG. 9 is a putative amino acid sequence of AgsA protein of *Aspergillus nidulans* (SEQ ID NO: 1).

FIG. 10A is a part of a nucleotide sequence (including an intron) of a nucleic acid molecule encoding AgsA protein of *Aspergillus nidulans* (SEQ ID NO: 2).

FIG. 10B is a continuation of the nucleotide sequence of FIG. 10A (including an intron) of a nucleic acid molecule encoding AgsA protein of *Aspergillus nidulans* (SEQ ID NO: 2).

FIG. 10C is a continuation of the nucleotide sequence of FIG. 10B (including an intron) of a nucleic acid molecule encoding AgsA protein of *Aspergillus nidulans* (SEQ ID NO: 2).

FIG. 11 is a putative amino acid sequence of AgsB protein of *Aspergillus nidulans* (SEQ ID NO: 3).

FIG. 12A is a nucleotide sequence (including an intron) of a nucleic acid molecule encoding AgsB protein of *Aspergillus nidulans* (SEQ ID NO: 4).

FIG. 12B is a continuation of the nucleotide sequence of FIG. 12A (including an intron) of a nucleic acid molecule encoding AgsB protein of *Aspergillus nidulans* (SEQ ID NO: 4).

FIG. 17 is a putative amino acid sequence of AgsA protein of *Aspergillus oryzae* (SEQ ID NO: 27).

FIG. 18A is a nucleotide sequence of agsA gene of *Aspergillus oryzae* (SEQ ID NO: 28).

FIG. 18B is a continuation of the nucleotide sequence of FIG. 18A of agsA gene of *Aspergillus oryzae* (SEQ ID NO: 28).

FIG. 19 is a putative amino acid sequence of AgsB protein of *Aspergillus oryzae* (SEQ ID NO: 29).

FIG. 20A is a nucleotide sequence of agsB gene of *Aspergillus oryzae* (SEQ ID NO: 30).

FIG. 20B is a continuation of the nucleotide sequence of FIG. 20A of agsB gene of *Aspergillus oryzae* (SEQ ID NO: 30).

FIG. 21 is a putative amino acid sequence of AgsC protein of *Aspergillus oryzae* (SEQ ID NO: 31).

FIG. 22A is a nucleotide sequence of agsC gene of *Aspergillus oryzae* (SEQ ID NO: 32).

FIG. 22B is a continuation of the nucleotide sequence of FIG. 22A of agsC gene of *Aspergillus oryzae* (SEQ ID NO: 32).

DESCRIPTION OF EMBODIMENTS

Figure 1:
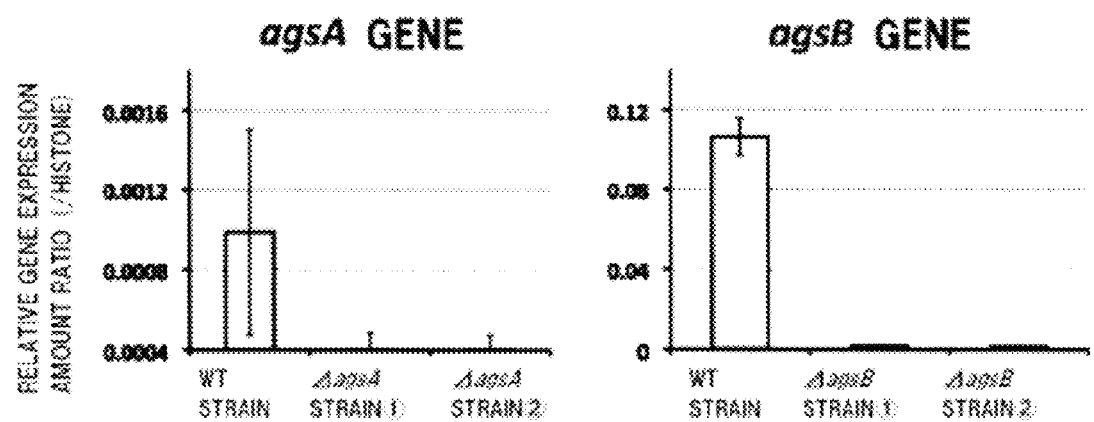
FIG. 1 provides graphs showing expression of agsA gene and agsB gene in quantitative reverse transcription-polymerase chain reaction (RT-PCR) in Production Example 3.

The present invention provides a method of producing a substance, including the steps of:
culturing a mutant filamentous fungus with no expression of α-1,3-glucan to allow the filamentous fungus to produce a substance; and
collecting the resulting substance.

Mutant Strain of Filamentous Fungus

In the present invention, the term "mutant filamentous fungus with no expression of α-1,3-glucan" encompasses not only a mutant strain of a filamentous fungus with no expression of α-1,3-glucan but also a mutant strain of a filamentous fungus with substantially no expression of α-1,3-glucan. More specifically, the mutant strain with substantially no expression of α-1,3-glucan refers to a mutant strain that expresses only a small amount of α-1,3-glucan and shows significant suppression of aggregation of cells, which is the effect of the present invention, and an example thereof is a strain having an expression amount of α-1,3-glucan of 30% or less with respect to that of a wild-type strain, more preferably 10% or less with respect to that of the wild-type strain.

Examples of the filamentous fungus include the genus *Aspergillus*, the genus *Penicillium*, the genus *Trichoderma*, the genus *Cephalosporium*, the genus *Acremonium*, and the genus *Neurospora*. Of those, the genus *Aspergillus* is more preferred. Examples of the filamentous fungi of the genus *Aspergillus* to be used in the present invention include *Aspergillus nidulans*), *Aspergillus oryzae, Aspergillus niger*, and *Aspergillus fumigatus*. Of those, *Aspergillus nidulans, Aspergillus oryzae*, or *Aspergillus niger* is preferred.

The method of the present invention has a feature in using a mutant strain of a filamentous fungus with no expression of α-1,3-glucan. An example of such mutant filamentous fungus is one deficient in at least one α-1,3-glucan synthase ags gene. Examples of the α-1,3-glucan synthase ags genes include: agsA (Genbank accession No. XM_658397) and agsB (Genbank accession No. XM_655819) of *Aspergillus nidulans*; agsA, agsB, and agsC of *Aspergillus oryzae*; ags1 (Genbank accession No. XM_743319) of *Aspergillus fumigatus*; agsE (Genbank accession No. AY530790) of *Aspergillus niger*; and agsB (Genbank accession No. AY530792) of *Penicillium chrysogenum*. Of those, agsA, agsB, and agsC genes of *Aspergillus oryzae* are registered in *Aspergillus* database AspGD (http://www.aspergillusgenome.org) with gene numbers of agsA (AO090026000523), agsB (AO090003001500), and agsC (AO090010000106) genes, respectively. The amino acid sequence of AgsA protein of *Aspergillus nidulans* (SEQ ID NO: 1) is shown in FIG. 9, and the nucleotide sequence of a nucleic acid molecule encoding AgsA protein of *Aspergillus nidulans* (SEQ ID NO: 2) is shown in FIG. 10A to FIG. 10C. In addition, the amino acid sequence of AgsB protein of *Aspergillus nidulans* (SEQ ID NO: 3) is shown in FIG. 11, and the nucleotide sequence of a nucleic acid molecule encoding AgsB protein of *Aspergillus nidulans* (SEQ ID NO: 4) is shown in FIG. 12A and FIG. 12B. The amino acid sequence of AgsA protein of *Aspergillus oryzae* (SEQ ID NO: 27) is shown in FIG. 17, and the nucleotide sequence of a nucleic acid molecule encoding AgsA protein of *Aspergillus oryzae* (SEQ ID NO: 28) is shown in FIG. 18A and FIG. 18B. The amino acid sequence of AgsB protein of *Aspergillus oryzae* (SEQ ID NO: 29) is shown in FIG. 19, and the nucleotide sequence of a nucleic acid molecule encoding AgsB protein of *Aspergillus oryzae* (SEQ ID NO: 30) is shown in FIG. 20A and FIG. 20B. The amino acid sequence of AgsC protein of *Aspergillus oryzae* (SEQ ID NO: 31) is shown in FIG. 21, and the nucleotide sequence of a nucleic acid molecule encoding AgsC protein of *Aspergillus oryzae* (SEQ ID NO: 32) is shown in FIG. 22A and FIG. 22B. Examples of the mutant filamentous fungus include ones deficient in one or two or more of the above-mentioned α-1,3-glucan synthases. In the present invention, when *Aspergillus nidulans* is used as the filamentous fungus, a strain deficient in at least agsB gene is preferred.

In the present invention, examples of the deficiency in α-1,3-glucan synthase ags genes include: a deletion of the whole or part of the coding region of α-1,3-glucan synthase in a genome; an insertion of another nucleic acid molecule into the whole or part of the coding region; and a substitution of the whole or part of the coding region by another nucleic acid molecule. In addition, the deficiency in α-1,3-glucan synthase ags gene encompasses not only an addition, deletion, and substitution of a predetermined nucleic acid molecule to the above-mentioned coding region but also a conditional gene deficiency designed so that α-1,3-glucan is expressed only under a certain condition. Therefore, the method of the present invention also encompasses a method including a step of culturing a mutant strain having the conditional gene deficiency under such a condition that α-1,3-glucan is not expressed.

The method of the present invention may be used for the production of useful substances, for example, enzymes such as amylase and cellulase and low-molecular-weight compounds such as penicillin that the filamentous fungus originally has abilities to produce. In the method of the present invention, transformation may be performed so as to enhance the expression of the useful substances that the filamentous fungus originally has abilities to produce, or so as to express substances that the filamentous fungus originally has no abilities to produce. As such transformation method, a method known per se (such as methods disclosed in JP 2001-46078 A, JP 2005-52116 A, JP 2009-118783 A, JP 11-506025 A, and JP 2007-508022 A) may be used, the method involving utilizing an expression vector constructed so that the filamentous fungus can function as a host, and a plasmid constructed by functionally linking a gene encoding a homologous or heterologous protein to the expression vector.

A method of producing such mutant strain may be performed by, for example, the construction of a disruption cassette for a gene encoding α-1,3-glucan synthase and the introduction of the cassette into a genome gene by appropriately using a method known per se (e.g., methods described in Non Patent Literatures 2 to 5).

The useful substances that can be produced by the present invention are not particularly limited, and examples thereof include: low-molecular-weight compounds such as penicillin, statins, cephalosporin, kojic acid, citric acid, and malic acid; and high-molecular-weight compounds such as amylase, cellulase, protease, lipase, peptidase, esterase, and oxidase. In addition to the foregoing, examples of the useful substances include chemical products such as an organic acid, a pigment, and an agricultural chemical bulk, and various substances to be used as pharmaceutical products. In addition, the method of the present invention is also applicable to, for example, the production of bioethanol through biomass decomposition (e.g., one using a mold genetically modified so as to highly produce cellulase or the like).

Culturing Step

The method of the present invention includes a step of culturing a mutant filamentous fungus with no expression of α-1,3-glucan to allow the filamentous fungus to produce a substance. A medium to be used in the step is not particularly limited, and there may be used a wide range of media that may be used for the culture of a filamentous fungus. Examples thereof include CD minimal medium, YPD medium, TSB medium, malt medium, and PDA medium. To the medium, glucose, starch, soluble starch, or the like may be added as a carbon source. The addition amount of such carbon source is not particularly limited and may be appropriately set within a range of, for example, from 0.5% to 10%, more preferably from 1% to 4%. A culture temperature is not particularly limited and may be appropriately set within a range of from 20° C. to 45° C., more preferably from 25° C. to 37° C. A culture time is also not particularly limited and may be appropriately set within a range of, for example, from 12 hours to 72 hours, more preferably from 24 hours to 48 hours.

A method of collecting the useful substance from the culture medium is not particularly limited, and there may be appropriately used a method known per se (e.g., centrifugation, recrystallization, a distillation method, a solvent extraction method, or chromatography).

EXAMPLES

Production Example 1

Construction of Disruption Cassette for agsA Gene

To construct a disruption cassette for agsA gene, a first round of PCR amplified gene fragments containing a 5' non-coding region (amplicon 1) and a coding region (amplicon 2) from an *A. nidulans* ABPU1 genomic DNA template, and amplified pyrG gene (amplicon 3) from an *A. oryzae* genomic DNA template. Amplicon 1 was amplified using primers agsA-LU (5'-AGTGGAGGAGTTAGGGAGTGAT-3' (SEQ ID NO: 5)) and agsA-LL (5'-CACAGGGTACGTCTGTTGT-GAAAGAGTAAGGTAGAAGCCCC-3' (SEQ ID NO: 6)), amplicon 2 was amplified using agsA-RU (5'-TTCTTCT-GAGGTGCAGTTCAGCAGATTATTACGCACCGGA-3' (SEQ ID NO: 7)) and agsA-RL (5'-AACCGTGGTTTTGGTGGCAAAG-3' (SEQ ID NO: 8)), and amplicon 3 was amplified using agsA-PU (5'-TACCT-TACTCTTTCACAACAGACGTACCCTGTGATGTTC-3' (SEQ ID NO: 9)) and agsA-PL (5'-GTAATAATCTGCT-GAACTGCACCTCAGAAGAAAAGGATG-3' (SEQ ID NO: 10)). The primers agsA-LU, agsA-RU, agsA-PU, and agsA-PL are chimeric oligonucleotides each containing a reverse-complement sequence for PCR fusion. The resulting three PCR products were gel-purified and used as substrates for a second round of PCR using agsA-LU and agsA-RL. The second round of PCR fused the three fragments obtained in the first round to produce a disruption cassette. All PCR reactions were performed using Gene Amp PCR System 9700 (Applied Biosystems, CA, USA) and Prime-STAR HS DNA polymerase (manufactured by Takara Bio Inc.). The resulting PCR product was gel-purified and used to transform an ABPU1 strain.

Production Example 2

Construction of Disruption Cassette for agsB Gene

A disruption cassette for agsB gene was constructed in the same manner as in Production Example 1 described above except that: primers agsB-LU (5'-GCAATGAGAGCTG-GAATCAGTG-3' (SEQ ID NO: 11)) and agsB-LL (5'-TGAGTCGGCCACAGCGGATGGAAT-TCGTCGTCTGGCTGTGAGTGTAAC-3' (SEQ ID NO: 12)) (for amplicon 1), agsB-RU (5'-TCTTCCAGT-TACTCCGTCGGTACCCAGCAACATGCTGGCCAT-ACGAC-3' (SEQ ID NO: 13)) and agsB-RL (5'-AAAGTCCTGGGTCTCTTCGTTC-3' (SEQ ID NO: 14)) (for amplicon 2), and argB-F (5'-GAATTC-CATCCGCTGTGGCCGACTCA-3' (SEQ ID NO: 15)) and argB-R (5'-GGTACCGACGGAGTAACTGGAAAGA-TACGA-3' (SEQ ID NO: 16)) (for amplicon 3) were used for the first round of PCR; and the primers agsB-LU and agsB-RL were used for the second round of PCR.

Production Example 3

Production of Mutant Strain and Measurement of α-1,3-Glucan Expression Amount A modified protoplast-PEG method was used for transformation for agsA and agsB gene deletion disruption, and the DNA fragments for agsA and agsB gene deletion disruption produced in the foregoing were used as DNA fragments for the transformation. A conidial suspension of *Aspergillus nidulans* ABPU1 ΔligD::ptrA (biotin (biA1), arginine (argB2), uridine (pyrG89), and pyridoxine (pyroA4)-requiring strain (provided by Dr. Tomonori Fujioka, Graduate School of Agricultural Science, Tohoku University)) was inoculated into YPD medium, and cultured with shaking at 37° C. for 20 hours. After the collection of the cells using a 17G1 sterilized glass filter, the cells were transferred to a centrifugation tube having a volume of 50 ml, and washed with sterile water. After that, the cells were suspended with addition of 30 ml of a protoplast forming solution (0.8 M NaCl, 10 mM $NaH_2PO_4$, 10 mg/ml Lysingenzyme (manufactured by Sigma Chemical Corporation), 5 mg/ml Cellulase Onozuka R-10 (manufactured by Yakult Pharmaceutical Ind. Co., Ltd.), and 2.5 mg/ml Yatalase (manufactured by Takara Bio Inc.), and shaken at 30° C. and 90 rpm for 3 hours to perform a protoplast forming reaction. The cells were filtered through sterilized MIRACLOTH (manufactured by CALBIOCHEM), and the protoplasts in the filtrate were obtained as a precipitate by centrifugation at 3,000×g and 4° C. for 5 minutes. The protoplasts were washed once with 0.8 M NaCl, and precipitated by centrifugation at 3,000×g and 4° C. for 5 minutes. The protoplasts were suspended in Solution 1 (0.8 M NaCl, 10 mM $CaCl_2$, 10 mM Tris-HCl, pH 8.0). A 200 μl aliquot of the protoplast suspension was transferred to centrifugation tubes each having a volume of 15 ml. To each of the tubes, 40 μl of Solution 2 (40% (w/v) PEG#4000, 50 mM $CaCl_2$, 50 mM Tris-HCl, pH 8.0) and 5 μl of each of the above-mentioned DNA solutions for transformation (5 μg in terms of DNA amount) were added, and the contents were mixed well and left to stand in ice for 30 minutes. 1 ml of Sol. 2 was added thereto, and the contents were mixed and left to stand at room temperature for 20 minutes. Sol. 2 was removed to a possible extent by washing twice with 5 ml of Sol. 1. In the case of selecting an agsA gene disruption strain, the protoplast suspension was added to Czapek-Dox (CD) soft agar medium supplemented with biotin, arginine, and pyridoxine at final concentrations of 0.02 μg/ml, 0.2 mg/ml, and 0.5 μg/ml, respectively, the medium having been warmed to 50° C., the contents were mixed, and the mixture was overlaid on CD agar medium supplemented with biotin, arginine, and pyridoxine at final concentrations of 0.02 μg/ml, 0.2 mg/ml, and 0.5 μg/ml, respectively. After that, the culture was continued at 30° C. until conidiation. The selection of the agsA gene disruption strain from the transformant was performed as follows: genomic DNA of the transformant was subjected to a PCR using the following primers (5'-GTACGGTGTAAGCTGCTCGCTGGAC-3' (SEQ ID NO: 17) and 5'-TCCTGGATCTTGTAAACTGAGTCTC-3' (SEQ ID NO: 18)), a strain in which only the amplified fragment of about 6,200 by was found was selected as an agsA gene disruption strain candidate, and finally, it was confirmed by quantitative RT-PCR that the agsA gene was not expressed (FIG. 1). In the case of selecting the agsB gene disruption strain, the protoplast suspension was added to Czapek-Dox (CD) soft agar medium supplemented with biotin, uridine, uracil, and pyridoxine at final concentrations of 0.02 μg/ml, 5 mM, 10 mM, and 0.5 μg/ml, respectively, the medium having been warmed to 50° C., the contents were mixed, and the mixture was overlaid on CD agar medium supplemented with biotin, uridine, uracil, and pyridoxine at final concentrations of 0.02 μg/ml, 5 mM, 10 mM, and 0.5 μg/ml, respectively. After that, the culture was continued at 30° C. until conidiation. The selection of the agsB gene disruption strain from the transformant was performed as follows: genomic DNA of the transformant was subjected to a PCR using the following primers (5'-AGGAAAGACTGTTGGATGAG-3' (SEQ ID NO: 19) and 5'-GACTTATTCGTGTTGACGTTGTA-3' (SEQ ID NO: 20)), a strain in which only the amplified fragment of about 5,150 by was found was selected as an agsB gene disruption strain candidate, and finally, it was confirmed by quantitative RT-PCR that the agsB gene was not expressed (FIG. 1).

Example 1 and Comparative Example 1

The ΔagsB strain obtained in Production Example described above was cultured under the following culture conditions, and a cell amount in a culture medium, a residual glucose amount, and a pH were measured every 12 hours after the culture, and a dry cell weight after the culture was measured (Example 1). A dry cell weight after the culture was measured in the same manner as described above except for using a wild-type strain in place of the ΔagsB strain Comparative Example 1

Culture Conditions

Figure 4:
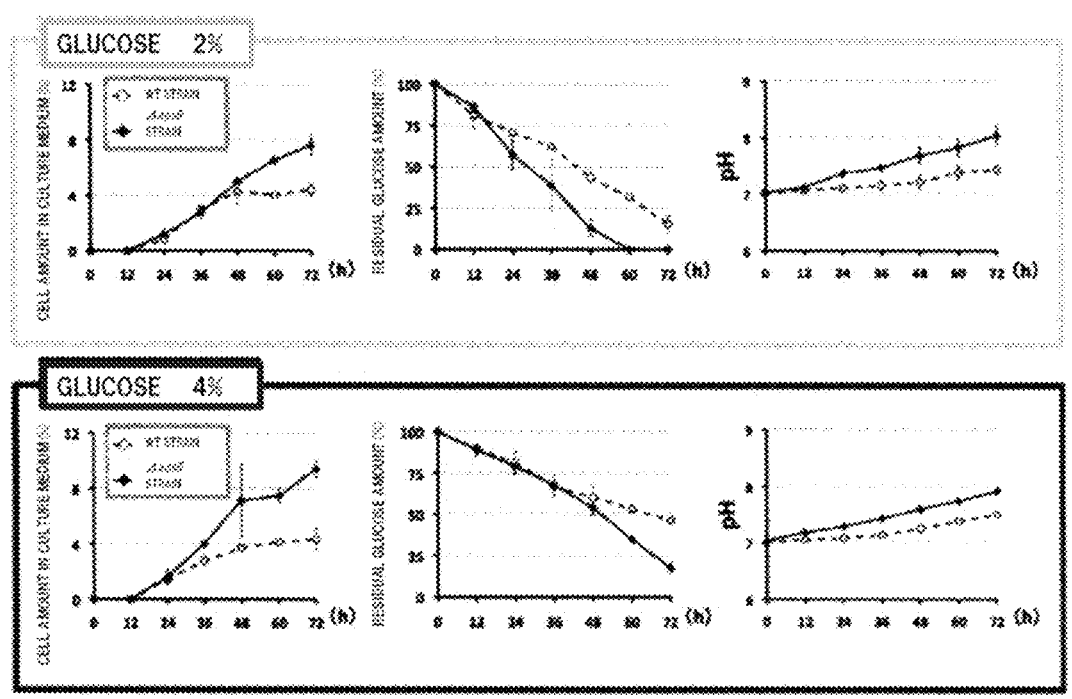
FIG. 4 provides graphs showing cell amounts in culture media, residual glucose amounts, and pH transitions at respective glucose concentrations in respective strains in Example 1 and Comparative Example 1.

Medium: CD minimal medium: 200 ml (500-ml flask with baffles)
Culture temperature: 37.0° C.
Culture time: 72 hr
Number of revolutions: 160 rpm
Number of conidia: $10^8$ conidia/L
Carbon source: glucose concentration: 2% or 4%
Number of trials: 5 times.
The results are shown in FIG. 2 to FIG. 4.
FIG. 2 provides graphs showing the dry cell weights after the culture. As shown in FIG. 2, the cell amount is increased in the ΔagsB strain as compared to the wild-type strain in liquid culture. In addition, in the ΔagsB strain, the cell amount is increased at a glucose concentration of 4% as compared to a glucose concentration of 2%. FIG. 3 provides photographs showing flasks after the above-mentioned test at a glucose concentration of 2%. As shown in FIG. 3, the ΔagsB strain grows homogeneously in the liquid medium, whereas the wild-type strain aggregates. FIG. 4 provides graphs showing the cell amounts in culture media, residual glucose amounts, and pH transitions at the respective glucose concentrations in the respective strains. In the wild-type strain, the increase in cell amount in the culture medium stopped at about 4% in both the cases of 2% and 4% glucose. On the other hand, in the ΔagsB strain, glucose was depleted in about 60 hours in the case of 2% glucose, but glucose was not depleted and the cell weight continued to be increased in the case of 4% glucose.

As understood from FIG. 2 to FIG. 4, the wild-type strain aggregates, and hence the cell amount in the strain cannot be increased to a certain level or more, whereas the ΔagsB strain grows homogeneously in the culture medium, and hence the cell amount in the strain can be increased to a great extent as compared to the wild-type strain.

Example 2 and Comparative Example 2

Figure 5:
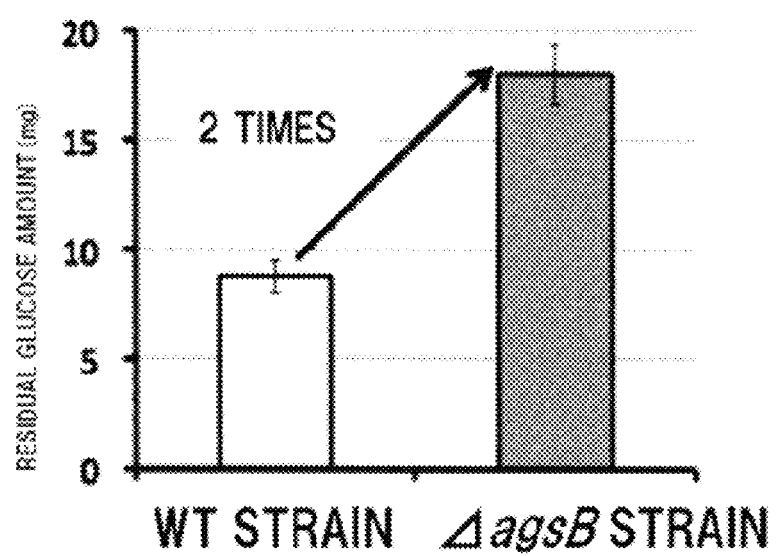
FIG. 5 is a graph showing dry cell weights after culture in Example 2 and Comparative Example 2.

The ΔagsB strain (Example 2) obtained in Production Example described above and the wild-type strain (Comparative Example 2) were each cultured with a jar-type culture device under the following culture conditions, and dry cell weights after the culture were measured:
Culture Conditions
Medium: CD medium: 3 L
Culture temperature: 37.0° C.
Culture time: 48 hr
Number of revolutions: 300 rpm
Number of conidia: $10^8$ conidia/L
Carbon source: glucose concentration: 2%
Amount of applied pressure: 0.3 MPa
Number of trials: 5 times each
The results are shown in FIG. 5. As shown in FIG. 5, also in the jar-type culture device, the cell amount is increased to a great extent in the ΔagsB strain as compared to the wild-type strain.

Example 3 and Comparative Example 3

The production amount of penicillin was measured for evaluating an ability to produce a low-molecular-weight compound.

Figure 6:
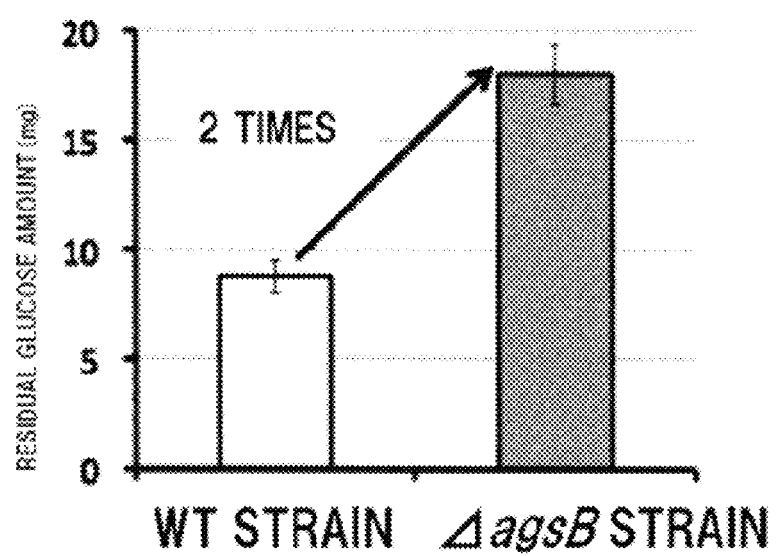
FIG. 6 is a graph showing dry cell weights and penicillin concentrations after culture in Example 3 and Comparative Example 3.

Specifically, first, the ΔagsB strain obtained in Production Example described above (Example 3) and the wild-type strain (Comparative Example 3) were cultured under the following culture conditions:
Culture Conditions
Medium: YPD medium: 100 mL (200-mL flask)
Culture temperature: 37° C.
Culture time: 48 hr
Number of revolutions: 160 rpm
Number of conidia: $10^7$ conidia/100 mL
Carbon source: glucose concentration: 2%
The culture medium was centrifuged, the culture supernatant was applied onto a paper disc, and the production amount of penicillin was measured by measuring the diameter of an inhibition zone with respect to standard cells for penicillin assay. Specifically, *Bacillus stearothermophilus* var. *calidolactis* (NBRC 100862: transferred from National Institute of Technology and Evaluation) as a standard strain for penicillin assay was mixed into agar medium containing 3% Tryptic soy broth (manufactured by Becton, Dickinson and Company) so as to achieve a final turbidity of O.D.=0.1, and 100 μl of the culture supernatant was impregnated into a sterilized paper disc placed at the center of a dish. The dish was incubated at 55° C. for 16 hours, and the diameter of an inhibition zone in which the standard strain for penicillin assay was unable to grow was measured. The production amount of penicillin was calculated from the diameters of inhibition zones obtained by applying commercially available penicillin G (manufactured by SIGMA) adjusted to 0.01, 0.025, 0.05, and 0.1 μg/ml onto paper discs in the same manner as described above. The production amount of penicillin was 15.9 ng/ml in the wild-type strain, whereas the production amount of penicillin was increased to a great extent to 58.6 ng/ml in the ΔagsB strain (FIG. 6).

In addition, dry cell weights were measured using the precipitates obtained by centrifugation. The dry cell weight was 175.7 mg in the wild-type strain, whereas the dry cell weight was also increased by about 1.3 times to 227.6 mg in the ΔagsB strain (FIG. 6).

Example 4 and Comparative Example 4

The production amount of amylase was measured for evaluating an ability to produce a high-molecular-weight compound.

Specifically, the ΔagsB strain obtained in Production Example described above (Example 4) and the wild-type strain (Comparative Example 4) were cultured under the following culture conditions:
Culture Conditions
  Medium: CD minimal medium: 200 mL (500-mL flask)
  Culture temperature: 37° C.
  Culture time: 48 hr or 36 hr
  Number of revolutions: 160 rpm
  Number of conidia: $10^7$ conidia/100 mL
  Carbon source: 2% starch or 2% soluble starch The cells were filtered from the culture medium, and the culture supernatant was measured for its amylase activity. Specifically, the cells after the elapse of 24 hours, 36 hours, and 48 hours (for only the starch addition condition) from the start of the culture were filtered through MIRACLOTH (manufactured by CALBIOCHEM), and the culture filtrate was measured for its amylase activity with an α-amylase measurement kit (manufactured by Kikkoman Biochemifa Company). The measurement was performed according to a method described in the manufacturer's instructions included with the kit, and the amylase activity in the culture supernatant was evaluated based on the definition that 1 U was a titer for releasing 1 μmol of CNP from N3-G5-β-CNP per minute. In addition, the filtered cells were lyophilized, and dry cell weights were measured. The results are shown in FIG. 7.

Figure 7:
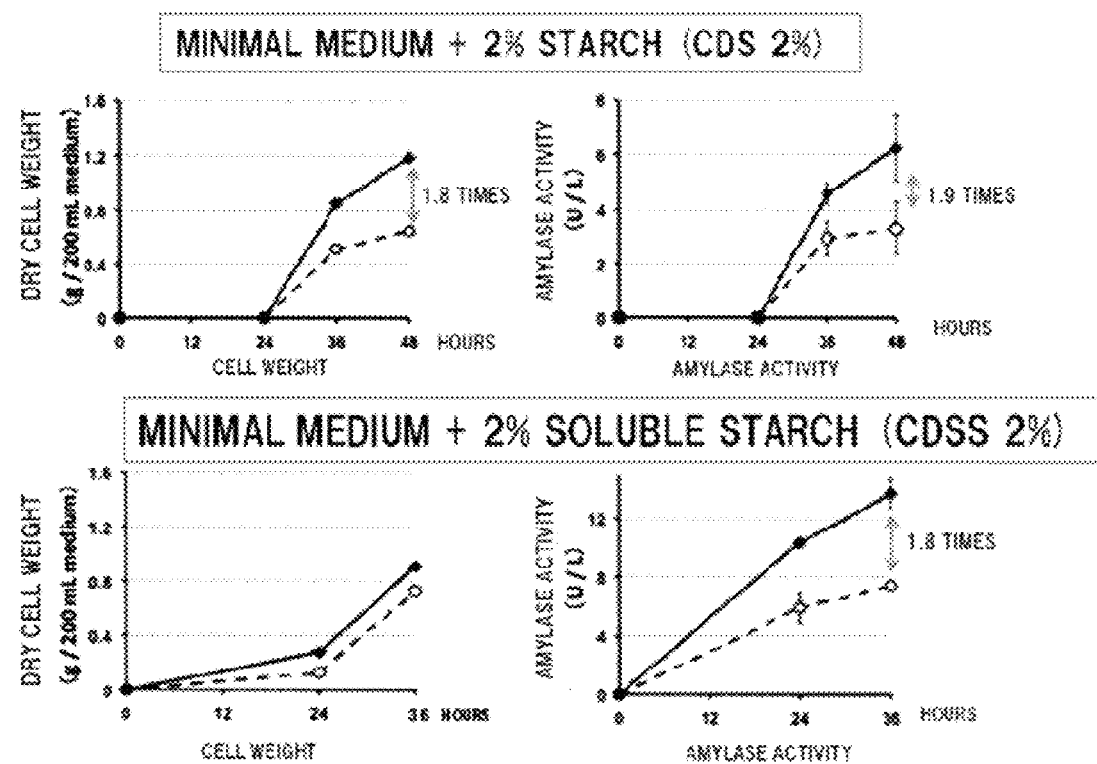
FIG. 7 provides graphs showing transitions of dry cell weights and amylase activities in Example 4 and Comparative Example 4.

As apparent from FIG. 7, it is found that the ΔagsB strain shows amylase activities about 2 times as high as those of the wild-type strain both under the starch addition condition and under the soluble starch addition condition.

Example 5 and Comparative Example 5

Figure 8:
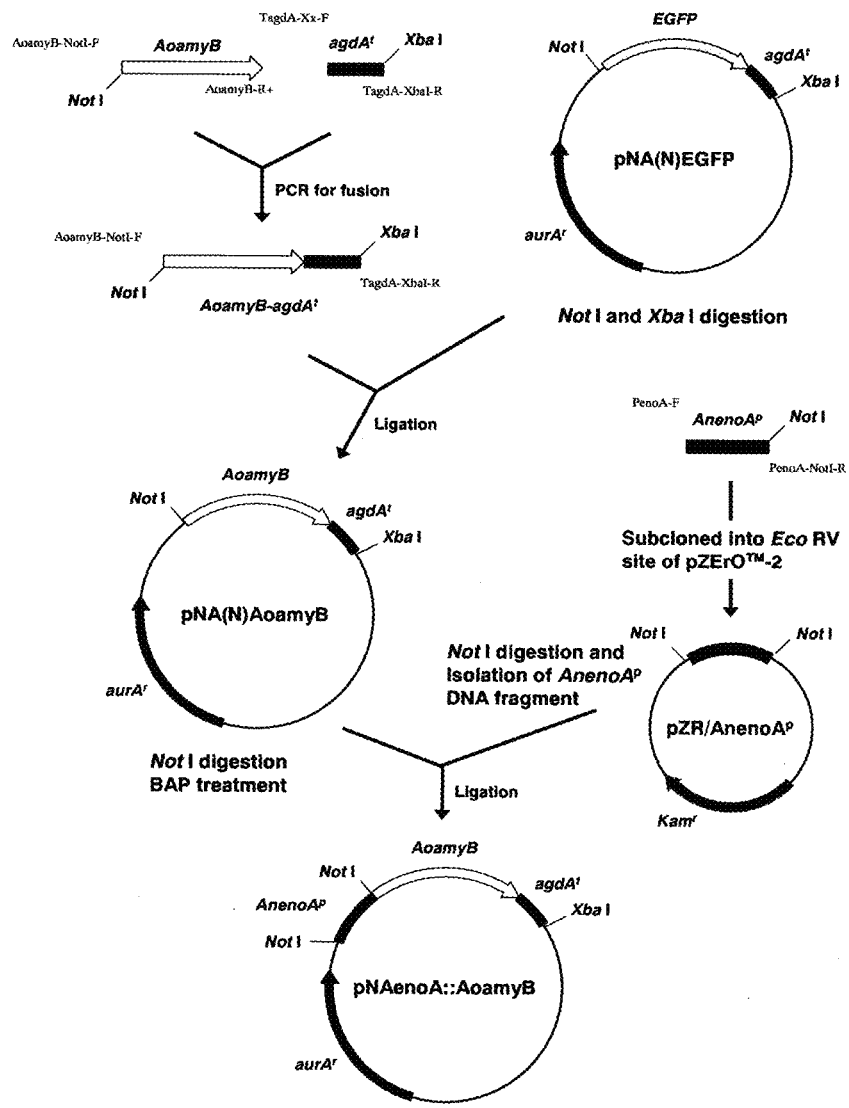
FIG. 8 is an illustration of an outline of the design of a ΔagsB strain highly expressing a heterologous protein.

Method of producing vector highly expressing *Aspergillus oryzae* amylase (FIG. 8)

Amylase gene was amplified from genomic DNA of *Aspergillus oryzae* through a PCR reaction, and connected to a terminator of agdA gene of *Aspergillus nidulans*. The DNA fragment was defined as AoamyB-agdA$^t$. The amylase gene was amplified using as PCR primers AoamyB-Not I-F (sequence: 5'-TGAATTCGCGGCCGCTATTTAT-GATGGTCGCGTGGTG-3' (SEQ ID NO: 21)) and AoamyB-R+(sequence: 5'-CTTCTTGAGTGAGCT-CACGAGCTACTACAGATCT-3' (SEQ ID NO: 22)), and the terminator of the agdA gene was amplified using as PCR primers TagdA-Xx-F (sequence: 5'-TGTAGTAGCTCGT-GAGCTCACTCAAGAAGCGTAACAGGATAGCCT-3' (SEQ ID NO: 23)) and TagdA-XbaI-R (sequence: 5'-GC-TATCTAGAGGCCTGCAGGAGATC-3' (SEQ ID NO: 24)). AoamyB-Not I-F has added thereto a recognition sequence for a restriction enzyme Not I (underlined part). In addition, TagdA-Xx-F has added thereto a sequence that overlaps part of the sequence of AoamyB gene (underlined part), and TagdA-XbaI-R has added thereto a recognition sequence for a restriction enzyme Xba I (underlined part). The gene fragment amplified using AoamyB-Not I-F and AoamyB-R+(AoamyB fragment) and the gene fragment amplified using TagdA-Xx-F and TagdA-XbaI-R (agdA$^t$ fragment) were connected using a fusion PCR method. This method is a method involving performing a PCR reaction using as a template a mixture of the AoamyB fragment and the agdA$^t$ fragment and using AoamyB-Not I-F and TagdA-XbaI-R, the method being able to connect both the gene fragments. The DNA fragment AoamyB-agdA$^t$ after the connection was digested with the restriction enzymes Not I and Xba I and introduced into the Not I and Xba I sites of pNA (N) EGFP (Furukawa et al. Biosci. Biothechnol. Biochem., 71(7), 1724-1730, 2007). pNA(N)EGFP is a vector having aureobasidin resistance gene (auA$^r$) as a selection marker in *Aspergillus nidulans*, and the digest of the vector with Not I and Xba I was used for gene introduction. The plasmid pNA(N)AoamyB obtained by the introduction of the DNA fragment AoamyB-agdA$^t$ was digested with the restriction enzyme Not I and then subjected to Bacterial alkaline phosphatase (BAP) (manufactured by Takara) treatment, and a promoter AnenoA$^p$, which was strongly expressed in *Aspergillus nidulans*, was introduced therein. AnenoA$^p$ was amplified from genomic DNA of *Aspergillus nidulans* using PCR primers PenoA-F (sequence: 5'-TGGTAAGAGTCGTCATATCGAG-3' (SEQ ID NO: 25)) and PenoA-Not I-R (sequence: 5'-TAGCGGCCGCGAATTCGATGAACTAGAAGGA-TAGAG-3' (SEQ ID NO: 26)). PenoA-Not I-R has added thereto a recognition sequence for the restriction enzyme Not I (underlined part). A fragment of AnenoA$^p$ in which the Not I site was added to both ends of the fragment was obtained by once introducing a fragment of AnenoA$^p$ into the EcoRV site of a plasmid pZEro™-2 (manufactured by Invitrogen), followed by digestion with Not I. The fragment of AnenoA$^p$ was introduced into the Not I site of pNA(N) AoamyB to produce a vector pNAenoA::AoamyB highly expressing *Aspergillus oryzae* amylase. The vector may be introduced into the ΔagsB strain of *Aspergillus nidulans* to produce a ΔagsB strain highly expressing a heterologous protein.

Example 6 and Comparative Example 6

Amylase activity was measured in a strain highly expressing amylase. Specifically, the vector pNAenoA::AoamyB highly expressing *Aspergillus oryzae* amylase produced by the method described in Example 5 and Comparative Example 5 was introduced into the wild-type strain and α-1,3-glucan-deficient strain of *Aspergillus nidulans* (AG-deficient strain) to produce a wild-type strain and an AG-deficient strain each highly expressing a heterologous protein. Those strains were each measured for its amount of amylase to be secreted into the culture supernatant.

Specifically, the AG-deficient strain and the wild-type strain, and the AG-deficient strain highly expressing amylase and the wild-type strain highly expressing amylase were cultured under the following culture conditions:
Culture Conditions
  Medium: CD minimal medium 50 mL (200-mL flask)
  Culture temperature: 37° C.
  Culture time: 24 hr
  Number of revolutions: 160 rpm
  Number of conidia: $10^7$ conidia/100 mL
  Carbon source: 2% maltose The cells were filtered from the culture medium, and the culture supernatant was measured for its amylase activity. Specifically, the cells after the elapse of 24 hours from the start of the culture were filtered through MIRACLOTH (manufactured by CALBIOCHEM), and the culture filtrate was measured for its amylase activity with an α-amylase measurement kit (manufactured by Kikkoman Biochemifa Company). The measurement was performed according to a method described in the manufacturer's instructions included with the kit, and the amylase activity in the culture supernatant was evaluated based on the definition that 1 U was a titer for releasing 1 μmol of CNP from N3-G5-β-CNP per minute. The results are shown in Table 1 below.

TABLE 1

Production amounts of amylase in wild-type strain and AG-deficient strain highly expressing amyB (U/100 mL)

| Strain | *Aspergillus oryzae* amyB gene | | |
|---|---|---|---|
| | Non-recombinant strain | High expressing strain | |
| Wild-type strain | 0.21 | 0.56 | |
| AG-deficient strain | N.D. | 3.52 | 6.3 times |

As apparent from Table 1, it is found that the AG-deficient strain highly expressing amylase shows amylase activity about 6 times as high as that of the wild-type strain highly expressing amylase.

Example 7 and Comparative Example 7

A triple gene disruption strain of α-1,3-glucan synthase (ags) gene was established in *Aspergillus oryzae* to compare culture properties.

Figure 13:
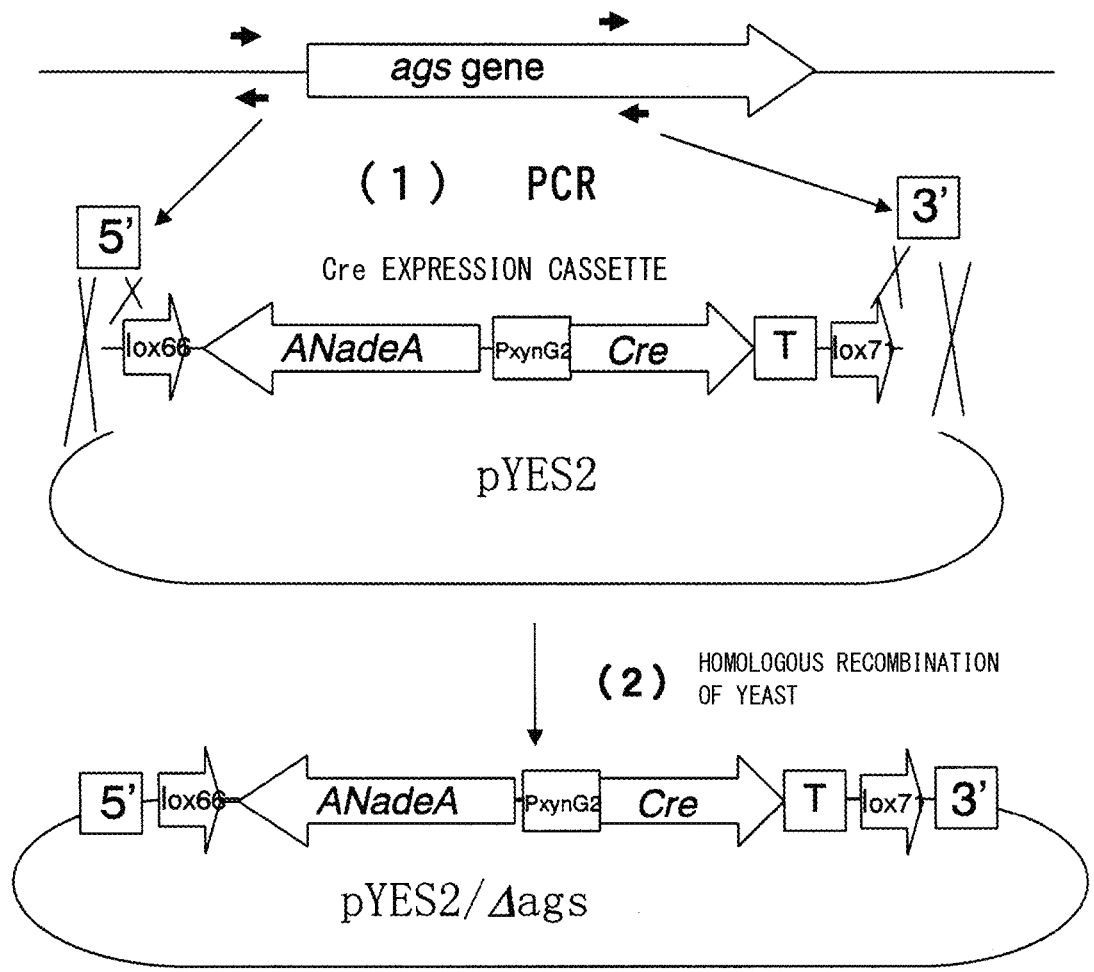
FIG. 13 is an illustration of an outline of the production of an ags gene disruption strain in Example 7.
Figure 14:
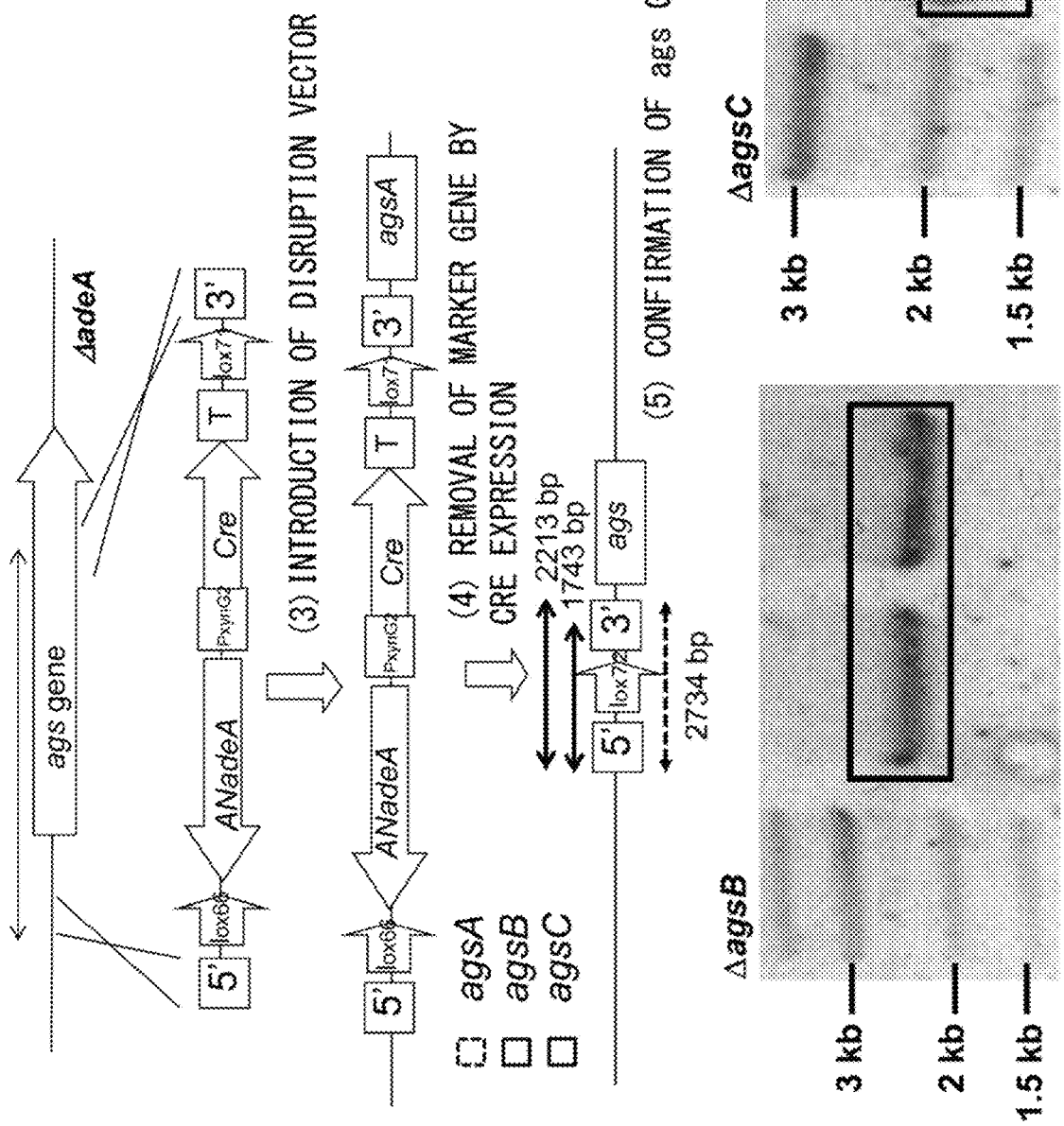
FIG. 14 is an illustration of an outline of the introduction of a vector for ags gene disruption in Example 7.
Figure 15:
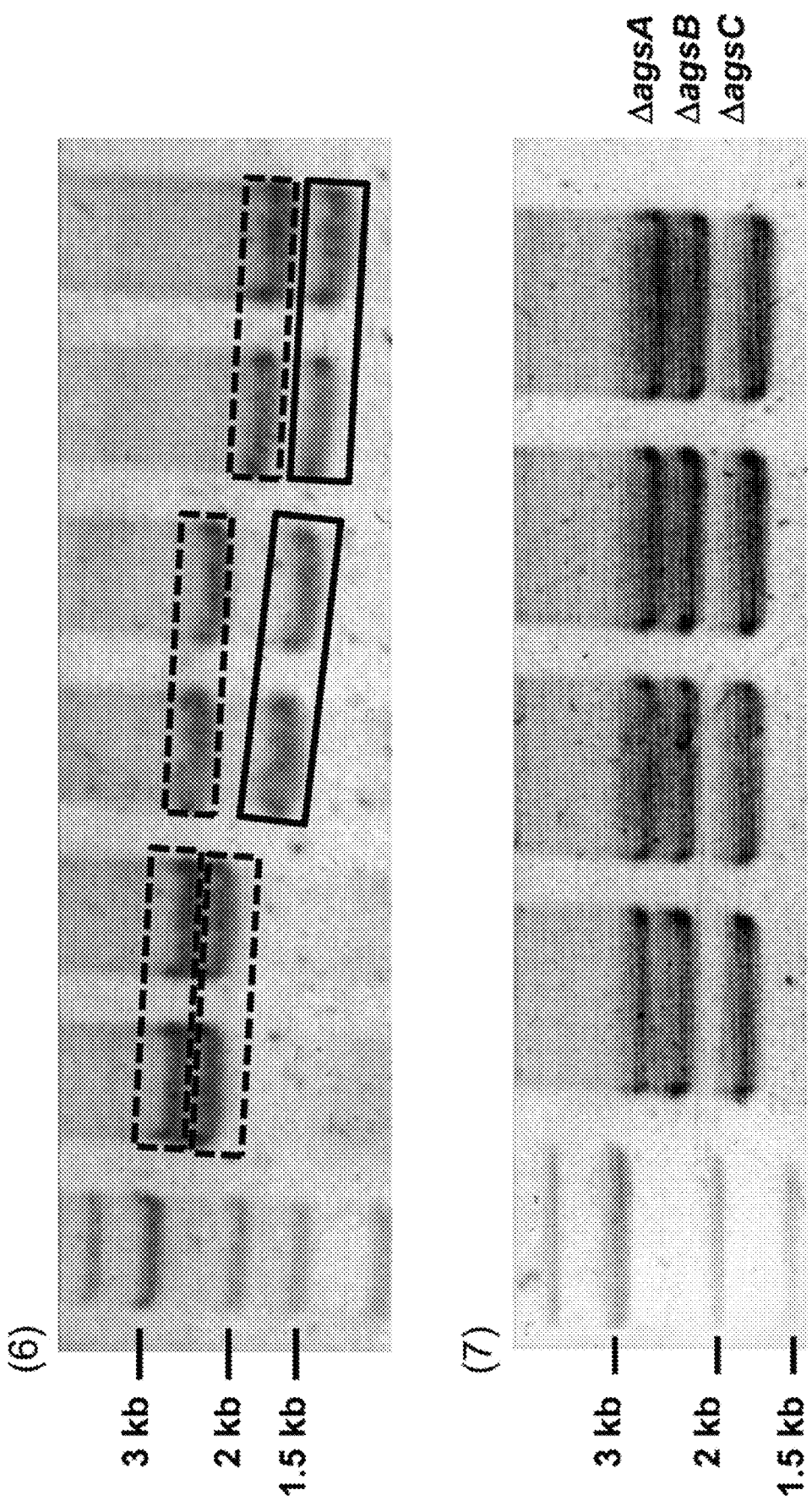
FIG. 15 provides photographs showing an outline of the production of a double gene disruption strain and a triple gene disruption strain in Example 7.

Three kinds of ags genes are present in the genome of *Aspergillus oryzae* and are named agsA (AO090026000523), agsB (AO090003001500), and agsC (AO090010000106), respectively (the gene numbers are registered in *Aspergillus* database AspGD (http://www.aspergillusgenome.org)). A triple gene disruption strain of those three kinds of ags genes was established using a multiple gene disruption method involving using a Cre-loxP system (see Applied and Environmental Microbiology, Volume 78 Number 12 Jun. 2012 p. 4126-4133). It was confirmed by the following method that all the three genes were disrupted. An outline of a production test on the triple gene disruption strain is illustrated in FIG. 13 to FIG. 15. Specifically, first, the 5' upstream region of each ags gene and a region in the ags gene were amplified by a PCR (FIG. 13(1)). In this case, a reverse primer in the 5' upstream region and a forward primer in the ags gene include homologous regions of loxP sequence. In addition, the sequences of primers for disruption are shown in Table 2.

TABLE 2

```
Primer for agsA disruption agsA-up: Fv:       5'-ATGTAAGCGTGACATAACTAATTACATGATGCGGCCCTCTCGATAAGGGCGTTACGGCTC-3'
                   (SEQ ID NO: 33)
agsA-up-Rv loxP:   5'-CCGAGACTCCTCATTGGAGTTAACGAGCTCACGATGCTCC-3'
                   (SEQ ID NO: 34)
agsA-down-Fw: loxP: 5'-GCTGGCGTAATAGCGAAGAGAAGTCGGCGTCTGGTCAGTC-3'
                   (SEQ ID NO: 35)
agsA-down-Rv:      5'-ACTACTAGCAGCAGCTGTAATACGACTCACTCACTATAGGGAATATTGGTCATATCCAGAGTCGCCT-3'
                   (SEQ ID NO: 36)

Primer for agsB disruption agsB-up Fv:        5'-ATGTAAGCGTGACATAACTAATTACATGATGCGGCCCTCTTCCTTCGCCATTCACACGTC-3'
                   (SEQ ID NO: 37)
agsB-up-Rv loxP:   5'-CCTAACCGAGACTCCTCATTGGAGTAACAGGGCTCAGATGTGAGG-3'
                   (SEQ ID NO: 38)
agsB-down-Fw loxP: 5'-CGCCAGCTGGCGTAATAGCGAAGAGACGCGAAGAATCAACCGGTG-3'
                   (SEQ ID NO: 39)
agsB-down-Rv:      5'-ACTACTAGCAGCAGCTGTAATACGACTCACTCACTATAGGGAATATTCCACCGTCATATCCGTACTG-3'
                   (SEQ ID NO: 40)

Primer for agsB disruption agsC-up Fv:        5'-ATGTAAGCGTGACATAACTAATTACATGATGCGGCCCTCTACGAGGATTGTTTGAAGAGC-3'
                   (SEQ ID NO: 41)
agsC-up-Rv loxP:   5'-CCTAACCGAGACTCCTCATTGGAGTTCCATGATTGGGAGAGTCGC-3'
                   (SEQ ID NO: 42)
agsC-down-Fw loxP: 5'-CGCCAGCTGGCGTAATAGCGAAGAGACCACGGAATCCATCAGCTG-3'
                   (SEQ ID NO: 43)
agsC-down-Rv:      5'-ACTACTAGCAGCAGCTGTAATACGACTCACTCACTATAGGGAATATTATCTGATATCGACTTATCCG-3'
                   (SEQ ID NO: 44)
```

Next, by means of a homologous recombination system of yeast, a Cre expression cassette including a selection marker in *Aspergillus oryzae* (adeA) was linked to the 5' upstream region of the ags gene and the region in the ags gene to construct a vector for ags gene disruption (FIG. 13(2)). Next, the resulting ags gene disruption vector was introduced into the wild-type strain of *Aspergillus oryzae* (adeAΔ strain) (FIG. 14(3)). The strain was transferred to a medium containing xylose (1%) to induce the expression of Cre (FIG. 14(4)). Through this operation, recombination occurs in the loxP sequence by virtue of the action of Cre. Disruption was confirmed by the respective ags gene-specific primers (FIG. 14(5)). The sequences of the primers are shown in Table 3.

TABLE 4

Wet cell weights of wild-type strain and ags triple gene disruption strain (agsAΔagsBΔagsCΔ strain) of *Aspergillus oryzae* (mg/50 mL medium)

| Strain | Cell weight (mg) | |
| --- | --- | --- |
| | Glucose culture | Maltose culture |
| Wild-type strain | 443.6 | 444.2 |
| agsAΔagsBΔagsCΔ | 579.8 | 531.6 |

TABLE 3

```
Primer used for confirmation of agsA disruption agsA-up Fv:    5'-ATGTAAGCGTGACATAACTAATTACATGATGCGGCCCTCTCGATAAGGGCGTTACGGCTC-3'
               (SEQ ID NO: 45)
agsA:          5'-AGGCATAGACACAAGCGATG-3'
               (SEQ ID NO: 46)

Primer used for confirmation of agsB disruption agsB-up Fv:    5'-ATGTAAGCGTGACATAACTAATTACATGATGCGGCCCTCTTCCTTCGCCATTCACACGTC-3'
               (SEQ ID NO: 47)
agsB-down-Rv:  5'-ACTACTAGCAGCAGCTGTAATACGACTCACTCACTATAGGGAATATTCCACCGTCATATCCGTACTG-3'
               (SEQ ID NO: 48)

Primer used for confirmation of agsB disruption agsC-up Fv:    5'-ATGTAAGCGTGACATAACTAATTACATGATGCGGCCCTCTACGAGGATTGTTTGAAGAGC-3'
               (SEQ ID NO: 49)
agsC:          5'-CGTACTTCCAACGATGATCC-3'
               (SEQ ID NO: 50)
```

Next, a double gene disruption strain was produced by the same method except for using a single disruption strain as a host (FIG. 15(6)). Specifically, the ΔagsA strain was used as a host strain, and agsB and agsC genes were each disrupted (ΔagsAΔagsB, ΔagsAΔagsC). In addition, in the same manner as described above, the ΔagsC strain was used as a host strain, and agsB gene was disrupted (ΔagsCΔagsB). In addition, a triple gene disruption strain was produced by the same method except for using a double gene disruption strain as a host (FIG. 15(7)). Specifically, the ΔagsAΔagsB strain was used as a host strain, and agsC gene was disrupted.

Next, the ags triple gene disruption strain of *Aspergillus oryzae* produced through the above-mentioned operation was observed for its culture properties at the time of liquid culture.

Specifically, the ags triple gene disruption strain and wild-type strain of *Aspergillus oryzae* were cultured under the following culture conditions:

Culture Conditions

Medium: CD minimal medium: 50 mL (200-mL flask)

Culture temperature: 30° C.

Culture time: 48 hr

Number of revolutions: 160 rpm

Number of conidia: $10^7$ conidia/100 mL

Carbon source: 2% glucose or 2% maltose

Figure 16:
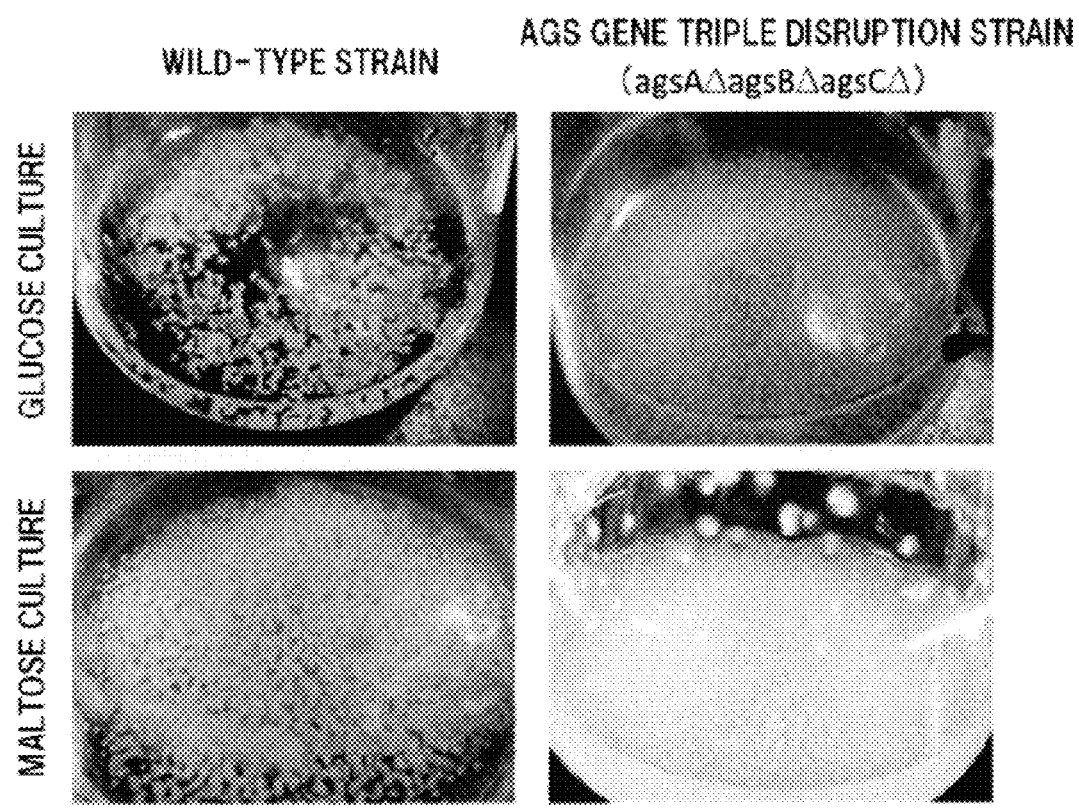
FIG. 16 provides photographs showing the culture properties of a wild-type strain and ags triple gene disruption strain (agsAΔagsBΔagsCΔ strain) of an *Aspergillus* in Example 7 and Comparative Example 7.

The results are shown in FIG. 16 and Table 4.

As shown in FIG. 16, the wild-type strain of *Aspergillus oryzae* also grows in a particulate form owing to the aggregation of hyphae, whereas the ags triple gene disruption strain of *Aspergillus oryzae* grows in a relatively dispersed state owing to less aggregation property of hyphae. In addition, similar results were obtained in the medium using glucose or maltose as the carbon source. As a result of comparison between cell weights after 48 hours of the culture, the ags triple gene disruption strain of *Aspergillus oryzae* showed an increase in cell weight as compared to the wild-type strain (Table 4). The cell weight of the ags triple gene disruption strain of *Aspergillus oryzae* reached 130% relative to that of the wild-type strain. Thus, high density culture can be performed through the deficiency in ags gene as with the case of *A. nidulans*.

INDUSTRIAL APPLICABILITY

According to the present invention, in the method of producing a substance using a filamentous fungus, the production amount of a useful substance can be drastically increased. In addition, a wide variety of useful substances can be produced without any particular limitation by the method of the present invention. Thus, the method of the present invention is very useful in industry.

Sequence Listing Free Text

SEQ ID NO: 5 is a primer.
SEQ ID NO: 6 is a primer.
SEQ ID NO: 7 is a primer.
SEQ ID NO: 8 is a primer.
SEQ ID NO: 9 is a primer.
SEQ ID NO: 10 is a primer.
SEQ ID NO: 11 is a primer.

SEQ ID NO: 12 is a primer.
SEQ ID NO: 13 is a primer.
SEQ ID NO: 14 is a primer.
SEQ ID NO: 15 is a primer.
SEQ ID NO: 16 is a primer.
SEQ ID NO: 17 is a primer.
SEQ ID NO: 18 is a primer.
SEQ ID NO: 19 is a primer.
SEQ ID NO: 20 is a primer.
SEQ ID NO: 21 is a primer.
SEQ ID NO: 22 is a primer.
SEQ ID NO: 23 is a primer.
SEQ ID NO: 24 is a primer.
SEQ ID NO: 25 is a primer.
SEQ ID NO: 26 is a primer.
SEQ ID NO: 33 is a primer.
SEQ ID NO: 34 is a primer.
SEQ ID NO: 35 is a primer.
SEQ ID NO: 36 is a primer.
SEQ ID NO: 37 is a primer.
SEQ ID NO: 38 is a primer.
SEQ ID NO: 39 is a primer.
SEQ ID NO: 40 is a primer.
SEQ ID NO: 41 is a primer.
SEQ ID NO: 42 is a primer.
SEQ ID NO: 43 is a primer.
SEQ ID NO: 44 is a primer.
SEQ ID NO: 45 is a primer.
SEQ ID NO: 46 is a primer.
SEQ ID NO: 47 is a primer.
SEQ ID NO: 48 is a primer.
SEQ ID NO: 49 is a primer.
SEQ ID NO: 50 is a primer.
SEQ ID NO: 33 is a primer.

The invention claimed is:

1. A method for increasing the production amount of protein per unit volume in a mutant filamentous fungus which lacks α-1,3-glucan compared to the corresponding parent filamentous fungus comprising the steps of:
   culturing the mutant filamentous fungus to allow said fungus to undergo a hyphal growth and produce the protein; and collecting the produced protein,
   wherein the mutant filamentous fungus is a mutant *Aspergillus oryzae,* and wherein the mutant filamentous fungus is deficient in agsB gene encoding α-1,3-glucan synthase and further deficient in at least one α-1,3-glucan synthase ags gene other than the agsB gene, and wherein the culturing step is conducted in liquid culture medium.

2. A method according to claim 1, wherein the protein is selected from the group consisting of amylase, cellulase, protease, lipase, peptidase, esterase, and oxidase.

3. The method according to claim 1, wherein a culture time of the mutant filamentous fungus is more than 24 hours in the culturing step.

4. The method according to claim 1, wherein the mutant filamentous fungus is cultured to the vegetative growth stage in the culturing step.

5. The method according to claim 1, wherein the culturing step is conducted for 12 hours or more.

6. A method for increasing the density of hyphae of a mutant filamentous fungus which lacks α-1,3-glucan compared to the corresponding parent filamentous fungus comprising the steps of:
   culturing the mutant filamentous fungus to allow for said fungus undergoing a hyphal growth to reach the increased level of the density of hyphae which is associated with protein production in said mutant filamentous fungus and
   collecting the produced protein,
   wherein the mutant filamentous fungus is a mutant *Aspergillus oryzae,* and wherein the mutant filamentous fungus is deficient in agsB gene encoding α-1,3-glucan and further deficient in at least one α-1,3-glucan synthase ags gene other than the agsB gene, and wherein the culturing step is conducted in liquid culture medium.

7. The method according to claim 6, wherein a culture time of the mutant filamentous fungus is more than 24 hours in the culturing step.

8. The method according to claim 6, wherein the mutant filamentous fungus is cultured to the vegetative growth stage in the culturing step.

9. The method according to claim 6, wherein the culturing step is conducted for 12 hours or more.

* * * * *

```
                        SEQUENCE LISTING

<160> NUMBER OF SEQ ID NOS: 50

<210> SEQ ID NO 1
<211> LENGTH: 2402
<212> TYPE: PRT
<213> ORGANISM: Aspergillus nidulans

<400> SEQUENCE: 1

Met Arg Trp Arg Pro Leu Asn Pro Leu Leu Pro Leu Leu Ala Ala Thr
1               5                   10                  15

Ala Ala Gly Trp Pro Tyr Glu Glu Ser Leu Val Asp Tyr Asn Leu Asn
            20                  25                  30

Val Asn Lys Asn Ala Ala Thr Pro Ala Asp Tyr Tyr Ala Pro Glu Trp
        35                  40                  45

Arg Asn His Thr Tyr Met Pro Ser Pro Glu Asn Trp Arg Phe Pro Phe
    50                  55                  60

Tyr Thr Leu Phe Leu Asp Arg Phe Val Asn Gly Asp Pro Thr Asn Asp
65                  70                  75                  80

Asn Ile Asn Gly Thr Val Tyr Glu His Asp Leu Asn Ser Asn Gln Met
                85                  90                  95

Arg His Gly Gly Asp Ala Gln Gly Leu Val Asp Thr Leu Asp Tyr Leu
            100                 105                 110

Gln Gly Met Gly Ile Lys Gly Ile Tyr Leu Ala Gly Thr Ile Leu Met
        115                 120                 125

Asn Gln Pro Trp Gly Ala Asp Gly Tyr Ser Ile Leu Asp Thr Thr Leu
    130                 135                 140

Leu Asp Gln His Phe Gly Thr Ile Gln Thr Trp Arg Asn Ala Ile Thr
145                 150                 155                 160

Glu Ile His Lys Arg Gly Met Tyr Val Leu Phe Asp Asn Thr Ile Ala
                165                 170                 175

Thr Met Gly Asp Leu Ile Gly Phe Lys Gly Tyr Leu Asn Val Ser Ala
            180                 185                 190

Pro Phe Ser Val Lys Glu His Glu Ala Val Trp Lys Ser Asp Arg Arg
        195                 200                 205

Tyr Val Asp Phe Asp Phe Gly Asn Thr Tyr Asn Gln Thr Cys Glu Tyr
    210                 215                 220

Pro Arg Phe Trp Asn Glu Thr Gly Trp Pro Val Asp Lys Asp Val Arg
225                 230                 235                 240

Asp Glu Leu Gln Gly Cys Tyr Ser Ser Asp Phe Asp Gln Tyr Gly Asp
                245                 250                 255
```

```
Arg Glu Ala Phe Gly Val Tyr Pro Asp Trp Gln Arg Gln Leu Ala Lys
        260                 265                 270

Phe Ala Ser Val Gln Asp Arg Leu Arg Glu Trp Asn Pro Ser Val Arg
            275                 280                 285

Glu Arg Leu Ile Arg His Ser Cys Met Ile Ile Lys Ala Leu Asp Ile
    290                 295                 300

Asp Gly Phe Arg Tyr Asp Lys Ala Thr Gln Ala Thr Val Asp Ala Leu
305                 310                 315                 320

Gly Asp Met Ser Ser Ala Tyr Arg Glu Cys Ala Arg Glu Val Gly Lys
                325                 330                 335

Asn Asn Phe Phe Leu Pro Gly Glu Ile Thr Gly Gly Asn Asn Phe Gly
            340                 345                 350

Ser Ile Tyr Leu Gly Arg Gly Arg Gln Pro Asn Gln Tyr Pro Asp Ser
        355                 360                 365

Ala Met Asp Ser Met Ala Met Asn Asn Glu Ser Asp His Gln Tyr Phe
    370                 375                 380

Leu Arg Glu Asp Gly Leu Gln Ala Leu Asp Ser Ala Ala Phe His Tyr
385                 390                 395                 400

Ser Ile Tyr Arg Ser Leu Thr Arg Phe Leu Gly Leu Asp Gly Asn Leu
                405                 410                 415

Ala Ala Gly Tyr Asp Thr Pro Ile Asp Trp Thr Asp Ala Trp Asn Val
            420                 425                 430

Met Val Met Thr Asn Asp Met Ile Asn Ala Asn Thr Gly Lys Phe Asp
        435                 440                 445

Pro Arg His Met Phe Gly Ala Thr Asn Gln Asp Val Phe Arg Trp Pro
    450                 455                 460

Ala Ile Lys Gln Gly Ile Glu Arg Gln Leu Leu Ala Met Phe Ile Thr
465                 470                 475                 480

Thr Leu His Leu Pro Gly Ile Pro Ile Leu Trp Gly Glu Gln
                485                 490                 495

Gly Phe Tyr Ile Leu Asp Ala Thr Ala Asp Asn Tyr Val Tyr Gly Arg
            500                 505                 510

Gln Ala Met Ser Pro Ala Thr Ala Trp Lys Thr His Gly Cys Phe Gln
        515                 520                 525

Leu Thr Ala Asp Gln Tyr His Asn Trp Pro Ile Ser Lys Gly Arg Glu
    530                 535                 540

Gly Cys His Asp Glu Thr Val Thr Tyr Asp His Arg Asp Pro Ser His
545                 550                 555                 560

Pro Leu Arg Asn Ile Ile Lys His Met Tyr Gln Leu Arg Gln Asp Tyr
                565                 570                 575

Gln Val Leu Asn Asp Gly Tyr Ser Val Gln Lys Leu Ser Asn Gln Thr
            580                 585                 590

Arg Gln Ile Phe Tyr Pro Gly Ser Asn Gly Thr Ala Thr Glu Thr Gly
        595                 600                 605

Met Trp Ser Val Leu Arg Asp Ser Val Tyr Lys Ile Gln Glu Leu His
    610                 615                 620

Asn Glu Gln Pro Val Trp Leu Val Tyr Gln Asn Asp Asn Lys Thr Val
625                 630                 635                 640

Glu Tyr Asn Phe Asp Cys Ser Asp Asn Asp Thr Ala Leu Ile Ser Pro
                645                 650                 655

Phe Ala Thr Lys Thr Thr Val Val Asn Leu Phe Tyr Pro His Asp Glu
            660                 665                 670
```

-continued

Tyr Asp Leu Lys Asp Gly Pro Lys Leu His Leu Asn Gly Ser Ala
            675                 680                 685

Glu Phe Asn Gly Cys Leu Asp Ser Met Thr Leu Lys Pro Phe Glu Phe
690                 695                 700

Lys Ala Phe Val Pro Lys Glu Arg Phe Val Lys Pro Arg Pro Met Ile
705                 710                 715                 720

Thr Lys Ile Thr Pro Gly His Asp Gln Pro Ile Ile Ser Lys Val Val
            725                 730                 735

Ala Ser Glu Ala Glu Asp Leu Asp Leu Ser Ile Tyr Phe Ser Ala Glu
                740                 745                 750

Met Asp Cys Asp Ser Val Thr Lys Ala Ile Lys Val Gln Ser Thr Thr
            755                 760                 765

Glu Val Asn Lys Thr Ala Leu Ile Asp Lys Asp Ser Val Lys Cys Arg
770                 775                 780

Arg Ile Asp Pro Asn Glu Thr Arg Trp Thr Ala Gln Leu Pro Ser Val
785                 790                 795                 800

Trp Ala Trp Ser Ser Lys Leu Thr Gly Val Tyr Asn Gly Ile His Arg
                805                 810                 815

Leu Thr Val Thr Asn Ala Thr Ser Glu Val Gly Gly Ser Thr Gln Ala
            820                 825                 830

Val Asp His Phe Leu Ile Arg Ile Gly Gln Ile Asp Asn Pro Met Val
                835                 840                 845

Phe Thr Thr Ala Asn Tyr Ser Thr Asp Leu Leu His Gln His Glu Asn
            850                 855                 860

Gly Thr Leu Tyr Ile Arg His Lys Ala Ala Gly Ala Asp Lys Tyr Arg
865                 870                 875                 880

Tyr Ser Thr Asn Trp Gly Ser Ser Phe Ser Asn Trp Arg Glu Tyr Lys
                885                 890                 895

Gly Gly Asp Glu Phe Ile Glu Glu Gln Pro Trp Ser Gly Thr Lys Lys
            900                 905                 910

Gln Lys Trp Asn Gly Lys His Val Arg Val Glu Tyr Trp Ser Lys Leu
            915                 920                 925

Thr Gly Ser Ser Ser Tyr Val Gln Glu Gly Asp Tyr Asp Thr Lys His
930                 935                 940

Gln Arg Arg Phe Pro His Leu Phe Phe Asn Gly Pro Tyr Asn Gln Tyr
945                 950                 955                 960

Gly Tyr Asp Ala Gly Leu Asp Asn Glu Val Lys Gln Asp Ser Asp Gly
                965                 970                 975

Tyr Trp Lys Tyr Arg Leu Arg Ala Glu Phe Pro Ala Gln Gly Gln Phe
            980                 985                 990

Asn Val Trp Gly Met Asn Pro Asp Gly Lys Pro Asp Gln Ser Phe Val
            995                 1000                1005

Phe Gly Asp Leu Asp Ser Asp Gly Val Leu Asp Arg Met Pro Pro
1010                1015                1020

Ser Ser Leu Asn Thr Leu Ser Ile Asn Val Thr Asp Arg Pro Pro
1025                1030                1035

Ser Ser Tyr Leu Ser Trp Asn Ile Trp Val Asp Asp Gly Thr Met
1040                1045                1050

Ser Ile Gln Phe Gln Pro Thr Gly Ser Arg Thr Ile Gln Met Val
1055                1060                1065

Val Tyr Phe Leu Leu Trp Phe Val Pro Leu Val Thr Ala Ile Gly
1070                1075                1080

Cys Val Tyr Ala Phe Met Lys Ser Phe Tyr Gln Val Lys Phe Asn

-continued

```
            1085                1090                1095
Gln Ile Gly Ile Ser Gln Lys Arg Ser Leu Phe Gly Phe Ser Val
            1100                1105                1110
Gly Arg Lys Pro Ser Leu Asn Pro Leu Thr Arg Leu Ala Asn Lys
            1115                1120                1125
Ser Gly Phe Leu Gln Ser Thr Pro Val Phe Gly Thr Gly Ser Ser
            1130                1135                1140
Arg Arg Arg Ser Val Leu Ile Ala Thr Met Glu Tyr Asp Ile Glu
            1145                1150                1155
Asp Trp Gly Ile Arg Ile Lys Ile Gly Gly Leu Gly Val Met Ala
            1160                1165                1170
Gln Leu Met Gly Lys Asn Leu Gly His Gln Asp Leu Ile Trp Val
            1175                1180                1185
Val Pro Cys Ala Gly Asp Val Asp Tyr Pro Glu Asp Gln Pro Ala
            1190                1195                1200
Glu Pro Met Phe Val Thr Val Leu Gly Asn Ile Tyr Glu Val Lys
            1205                1210                1215
Val Gln Tyr His Val Leu Asn Asn Ile Thr Tyr Val Leu Leu Asp
            1220                1225                1230
Ala Pro Val Phe Arg Gln Gln Ser Lys Ala Glu Pro Tyr Pro Ala
            1235                1240                1245
Arg Met Asp Asp Leu Asp Ser Ala Ile Tyr Tyr Ser Ala Trp Asn
            1250                1255                1260
Gln Cys Ile Ala Glu Thr Ile Lys Arg Phe Pro Ile Asp Leu Tyr
            1265                1270                1275
His Ile Asn Asp Tyr His Gly Ser Ile Ala Pro Leu Tyr Leu Leu
            1280                1285                1290
Pro Gln Thr Ile Pro Val Cys Leu Ser Leu His Asn Ala Glu Phe
            1295                1300                1305
Gln Gly Leu Trp Pro Met Arg Thr Gln Lys Glu Arg Asp Glu Val
            1310                1315                1320
Cys Ser Val Phe Asn Ile Asp Val Asp Val Ala Arg Arg Tyr Val
            1325                1330                1335
Gln Phe Gly Glu Val Phe Asn Met Leu His Ala Gly Ala Ser Tyr
            1340                1345                1350
Leu Arg Val His Gln Gln Gly Phe Gly Ala Val Gly Val Ser Arg
            1355                1360                1365
Lys Tyr Gly Lys Arg Ser Tyr Ala Arg Tyr Pro Ile Phe Trp Gly
            1370                1375                1380
Leu Lys Lys Val Gly Asn Leu Pro Asn Pro Asp Pro Ser Asp Thr
            1385                1390                1395
Ala Glu Trp Asn Lys Glu Leu Pro Lys Glu Ser Glu Ile Gln Val
            1400                1405                1410
Asp Gln Asn Tyr Glu Ala Ser Arg Ala Glu Leu Lys Arg Gln Ala
            1415                1420                1425
Gln Glu Trp Ala Gly Leu Glu Gln Asn Pro Asn Ala Asp Leu Met
            1430                1435                1440
Val Phe Val Gly Arg Trp Ser Met Gln Lys Gly Ile Asp Leu Ile
            1445                1450                1455
Ala Asp Val Met Pro Ala Val Leu Glu Ala His Pro Asn Val Gln
            1460                1465                1470
Leu Ile Cys Val Gly Pro Val Ile Asp Leu Tyr Gly Lys Phe Ala
            1475                1480                1485
```

```
Ala Leu Lys Leu Asp Arg Met Met Gln Leu Tyr Pro Gly Arg Val
    1490            1495                1500
Phe Ser Lys Pro Glu Phe Thr Ala Leu Pro Pro Tyr Ile Phe Ser
    1505            1510                1515
Gly Ala Glu Phe Ala Leu Ile Pro Ser Arg Asp Glu Pro Phe Gly
    1520            1525                1530
Leu Val Ala Val Glu Phe Gly Arg Lys Gly Ala Leu Gly Ile Gly
    1535            1540                1545
Ala Arg Val Gly Gly Leu Gly Gln Met Pro Gly Trp Trp Tyr Asn
    1550            1555                1560
Val Glu Ser Thr Thr Thr Ala His Leu Leu His Gln Phe Lys Leu
    1565            1570                1575
Ala Ile Gly Cys Ala Leu Asn Ser Lys Pro Gln Val Arg Ala Arg
    1580            1585                1590
Met Arg Ala Arg Ser Ala Lys Gln Arg Phe Pro Val Ala Gln Trp
    1595            1600                1605
Val Glu Asp Leu Glu Ile Leu Gln Ser Thr Ala Met Arg Ile His
    1610            1615                1620
Ser Lys Gly Leu Ala Lys Ala Ser Val Gln Pro Tyr Asn Ser Gly
    1625            1630                1635
Ser Asn Thr Pro Leu Gly Met Met Thr Pro Pro Ile Ala Ser Thr
    1640            1645                1650
Gly Thr Val Thr Pro Thr Gly Ile Gln Thr Pro Leu Ala His
    1655            1660                1665
Ser Arg Ser Gly Ser Tyr Ser Asn Ile Asn Arg Leu Ser Ala Tyr
    1670            1675                1680
Gly Pro Gln Gln Arg Asn Thr Ile Ile Tyr Ser Arg Asp Pro Ser
    1685            1690                1695
Pro Gly Gly Glu Asp Gln Pro Arg Ser Gly Ile Arg Gln Leu Ser
    1700            1705                1710
Leu Gly Val Arg Ala Gly Pro Gly His Leu Met Arg Arg Gly Arg
    1715            1720                1725
Arg Arg Leu Arg Arg Asn Ser His Ala Gly Thr Asp Glu Asn Ala
    1730            1735                1740
Ser Val Ser Met Thr Glu Glu Ser Ser Asp Asp Asp Ile Ile Pro
    1745            1750                1755
Ser Phe Tyr Gly Glu Glu Glu Tyr Thr Leu Thr Pro Glu Gln Ala
    1760            1765                1770
Glu Glu Val Arg Arg Ala Asp Met Thr Pro Gln Gln Glu Gln Asn
    1775            1780                1785
His Gly Ser Val Arg Asp Phe Phe Thr Arg Arg His Ser Ser Gln
    1790            1795                1800
Ser Ser Ile Leu Ser Arg Ser Val Leu Ser Pro Ala Ser Ser Thr
    1805            1810                1815
Thr Phe Asp Gly Asp Glu Thr Phe Val Pro Pro Ala Pro Pro Phe
    1820            1825                1830
Ala Glu Pro Gly Asn Arg Leu Ser Ser Ala Ser Val Leu Ser Val
    1835            1840                1845
Asp Ser Val Val Gly Glu Lys Lys Asp Tyr Lys Leu Gln Lys Val
    1850            1855                1860
Asp Pro Thr Phe Thr Asp Ser Thr Gly Glu Phe Tyr Lys Val Phe
    1865            1870                1875
```

-continued

Glu Arg Lys Leu Glu Lys Leu Asn Gly Ser Asn Ser Ile Ser Gln
1880                1885                1890

Leu Cys Ile Glu Glu Tyr Leu Glu Lys Ser Glu Lys Lys Trp Phe
1895                1900                1905

Asp Arg Phe Arg Asp Ala Arg Leu Gly Arg Lys Gln Ser Pro Ser
1910                1915                1920

Ser Ser Ile Phe Arg Thr Lys Phe Glu Gly Ser Ser Pro Met Ala
1925                1930                1935

Leu Val Ser Asn Asp Glu Val Gly Ser Arg Ala Ser Gly Ser Glu
1940                1945                1950

Pro Arg Met Arg Pro Asp Glu Phe Cys Leu Gly Asn Asp Tyr Val
1955                1960                1965

Pro Pro Ser Gly Leu Lys Lys Trp Met Gln Val Arg Ile Phe Asp
1970                1975                1980

Trp Pro Ile Tyr Ser Phe Ile Leu Gly Leu Gly Gln Ile Ile Ala
1985                1990                1995

Ala Asn Ser Tyr Gln Ile Thr Leu Leu Thr Gly Glu Val Gly Gln
2000                2005                2010

Arg Pro Glu Lys Leu Tyr Gly Ile Ala Thr Val Tyr Leu Val Ser
2015                2020                2025

Ser Ile Val Trp Trp Phe Leu Phe Arg Phe Cys Lys Ser Val Val
2030                2035                2040

Val Leu Ser Leu Pro Trp Leu Phe Tyr Gly Phe Ala Phe Val Leu
2045                2050                2055

Ile Gly Val Ala His Tyr Glu Gly Asp Ser Phe Ala Arg Ala Trp
2060                2065                2070

Ile Gln Asn Val Gly Ala Gly Val Tyr Ala Ala Ala Ser Ala Ser
2075                2080                2085

Gly Ser Leu Phe Phe Ala Leu Asn Phe Gly Asp Glu Asn Gly Ala
2090                2095                2100

Pro Val Lys Asn Trp Val Trp Arg Ala Cys Ile Ile Gln Gly Thr
2105                2110                2115

Gln Gln Ala Tyr Ile Ile Gly Leu Trp Tyr Trp Gly Thr Ser Ile
2120                2125                2130

Ser Gln Ala Val Thr Arg Gly Val Pro Asp Val Gln Ala His Ile
2135                2140                2145

Thr Glu Thr Trp Arg Met Thr Thr Ile Cys Met Pro Ile Ala Val
2150                2155                2160

Phe Leu Trp Val Leu Gly Ile Leu Val Phe Phe Gly Leu Pro Asn
2165                2170                2175

Tyr Tyr Arg Gln Thr Pro Gly Lys Val Pro Ser Phe Tyr Gln Ser
2180                2185                2190

Val Cys Arg Arg Lys Ile Ile Leu Trp Asn Phe Val Val Ile
2195                2200                2205

Leu Gln Asn Phe Phe Leu Ser Ala Pro Tyr Gly Arg Asn Trp Ser
2210                2215                2220

Phe Leu Trp Ser Ser Val His Ala Glu Pro Trp His Ile Gly Leu
2225                2230                2235

Leu Val Val Ala Phe Phe Gly Val Ala Trp Val Leu Ile Leu Cys
2240                2245                2250

Ile Phe Ala Arg Leu Ser Lys Ser His Ser Trp Ile Leu Pro Val
2255                2260                2265

Phe Ala Cys Gly Leu Gly Ala Pro Arg Trp Ala Gln Ile Trp Trp

```
         2270             2275              2280
Gly Val Ser Gly Met Gly Leu Phe Leu Pro Trp Ala Gly Ser Tyr
     2285             2290              2295
Thr Thr Gly Ala Leu Val Ser Arg Ser Leu Trp Leu Trp Leu Gly
     2300             2305              2310
Ile Leu Asp Ser Leu Gln Gly Leu Gly Phe Gly Met Ile Leu Leu
     2315             2320              2325
Gln Thr Leu Thr Arg Met His Ile Cys Phe Thr Leu Leu Ala Ser
     2330             2335              2340
Gln Val Leu Gly Ser Ile Ala Thr Ile Cys Ala Arg Ala Phe Ala
     2345             2350              2355
Pro Asn Asn Ile Gly Pro Gly Pro Ile Ser Pro Asp Ile Thr Asp
     2360             2365              2370
Gly Ala Gly Ala Val Ala Asn Ala Trp Phe Trp Ile Ala Leu Phe
     2375             2380              2385
Phe Gln Leu Leu Ile Cys Ser Phe Pro Ile Asp Val Met Ser
     2390             2395              2400

<210> SEQ ID NO 2
<211> LENGTH: 7919
<212> TYPE: DNA
<213> ORGANISM: Aspergillus nidulans

<400> SEQUENCE: 2
atgaggtgga ggcctttaaa cccgttactt ccgctgcttg cagcaaccgc agcaggctgg      60
ccctacgaag agtcattagt tgattataat ctcaacgtga acaaaaacgc tgccacccca     120
gcagattatt acgcaccgga atggaggaac cacacatata tgccgtcgcc agagaactgg     180
aggtttccat tctacaccct gtttctggac agattcgtca acggcgaccc tactaacgat     240
aatattaacg gaactgtcta tgaacatgat ttgaactcca accagatgcg acacggcggt     300
gatgcacaag gctggtagaa cactcgactacc ttcaaggaatgggaatcaaggtctga        360 ttttttgtttt cgtctcagct tcagccttcg ctaaccagat cttgtttagg ggatctacct     420
cgcgggtact attctcatga atcaaccctg gggcgcagac ggttattcga ttttggacac     480
tacgctgctg atcagcacct cgggaccat ccaaacctgg agaaatgcaa tcacagagat     540
tcacaagcgt gggatgtacg tcttattcga caacactatc gctacgtgag tctgctggtt     600
ttccaagtca aatgcgcgaa tgctaactac acccaaggat gggcgatttg atcggattca     660
aaggttattt gaacgttagc gccccgttct ctgtcaaaga gcacgaagct gtttggaagt     720
ctgaccgtcg ctacgtcgat tttgattttg gaaacaccta caatcagacc tgcgagtacc     780
ctcgattctg gaacgagact ggctggcccg ttgataaaga cgttcgtgat gagctacaag     840
gttgctatag tagtgatttc gatcaatacg gtgacaggga agctttcggt gtatatccag     900
actggcagcg acagctggcc aagtttcat cagtccagga tcgtctccgt gaatggaacc     960
caagcgttcg cgagagacta atcagacatt cctgcatgat tatcaaagct cttgacattg    1020
acggatttcg ctatgacaaa gccacgcagg ccacagtgga cgcccttgga gacatgtcga    1080
gtgcttatcg tgagtgtgcc cgtgaggtcg gtaaaaacaa cttttttcctc ccaggtgaga    1140 ttactggtgg aaacaatttc ggctcgatct atctcggacg aggaagacag cccaaccaat    1200
acccagactc tgctatggat tctatggcca tgaacaacga gtcggatcac caatattttc    1260
ttcgtgaaga tggtttacag gcgctcgata gcgctgcctt ccactactca atctatcgat    1320
ccctcacccg gttccttggc ctcgacggaa atcttgctgc tggttacgat acgccgattg    1380
```

```
actggacaga tgcctggaat gtaatggtga tgaccaatga catgataaac gcgaataccg   1440
gtaaatttga cccgcgacac atgtttggtg ccacgaacca ggatgttttt cgttggccag   1500
ccatcaaaca gggtatcgaa cgccaactcc tggcgatgtt cattacaaca cttcacctcc   1560
cgggtattcc aatattgttg tggggtgaag agcaaggttt ctatatcttg gacgccactg   1620
cagacaacta tgtctacggc cgccaggcga tgtcaccagc cacagcttgg aaaacccatg   1680
gatgcttcca attgacagca gatcagtacc acaactggcc tatcagcaaa ggacgtgaag   1740
gctgtcatga cgagacagta acctatgacc accgcgaccc gtctcatccg ctccgaaata   1800
tcatcaaaca tatgtaccag ttgcgacaag attaccaggt tttgaacgac ggatattctg   1860
tccagaaact ctccaatcaa acccgccaga ttttctatcc aggctcgaac ggaacggcta   1920
cggagaccgg aatgtggtct gtcttacgag actcagttta caagatccag gagctacaca   1980
acgagcaacc ggtttggctt gtataccaga tgacaacaa gacggtggaa tacaattttg    2040
actgcagtga taatgacacg gcgttgatat ccccctttgc caccaaaacc acggttgtca   2100 atctcttta cccgcatgac gaatatgact tgaaggacgg tccaaagaag ctccatctta    2160
atggctcagc ggagttcaat ggatgccttg atagcatgac gctgaagcct ttcgaattca   2220
aggctttcgt tccgaaagag cgatttgtga agcctagacc catgattacc aaaatcacac   2280
caggacacga ccaaccgatc atttccaaag tcgtggcgag cgaggcagag gatcttgatt   2340
tgagcattta cttctctgcg gagatggact gcgactcagt cacaaaagcg atcaaagtgc   2400
agtccaccac agaagtcaat aagacagctt tgattgacaa agacagcgtg aaatgcagga   2460
ggattgatcc aaacgaaacg cggtggactg cccagctacc cagcgtctgg gcgtggtcgt   2520
caaagttgac cggagtatac aatggaattc atcggctgac cgtcaccaat gccaccagcg   2580
aggttggagg ctcaacacag gctgttgatc actttctcat tcgcattggt caaatagaca   2640
atcccatggt cttcaccacg gccaattact ccactgacct acttcaccag cacgagaacg   2700
gaacactcta tattcgacac aaagccgctg gtgctgataa atatcgttat tccaccaatt   2760
ggggaagctc ttttttcaaac tggcgcgaat acaaaggtgg cgacgaattc attgaagaac   2820
aaccatggtc cggaactaaa aagcagaaat ggaatgggaa gcatgtccgc gttgagtact   2880
ggagcaagtt gactggtagc agcagctatg tccaagaagg tgactatgat accaagcatc   2940
aaagacgctt cccgcacctc ttcttcaatg ggccttacaa ccagtatgga tacgatgcag   3000
gactggacaa tgaggtgaaa caggacagtg acgggtactg gaaatatcgg ctccgagcgg   3060
aattccctgc tcagggacag tttaatgttt ggggtatgaa cccagacggg aagcccgacc   3120
agagttttgt gtttggtgat cttgattctg acggtgtttt ggaccgcatg ccaccatcct   3180
ccctgaacac ccttttctatt aacgtcaccg acaggccacc gtcgtcctat ctatcttgga   3240
atatttgggt cgatgacggt accatgagca tccagtttca accgactggc tcgaggacaa   3300
tccagatggt agtttatttc ttgctttggt tcgtaccgct tgtgacagct atcggatgcg   3360
tatatgcttt catgaaatcg ttttaccagg tcaaattcaa ccagattgga atcagccaga   3420
agcggtcatt attcggtttc tcagtcggcc ggaagccttc attgaatcca ctgacgcggc   3480
ttgccaataa atccggattt ctccaaaagca cgcctgtctt tggaacaggg tcttctcgca   3540
ggcgcagtgt tctcatcgcc actatggagt atgacattga ggactggggt atcaggatta   3600
aaattggtgg tcttggagtc atggcacagc tcatggcaa gaacctcggg catcaagatc    3660
tcatttgggt tgtcccatgt gcgggggacg tagactaccc agaggatcag ccagctgagc   3720
```

-continued

```
caatgtttgt gactgttctc gggaacatct acgaagtcaa ggttcagtat catgtcctga    3780
acaatattac atatgttctt ctcgatgcgc ccgttttccg tcaacagtca aaggctgagc    3840
cctaccctgc tcgcatggac gaccttgata gtgcgatata ctattccgcc tggaatcagt    3900
gcattgctga gaccatcaag cgcttcccta tcgaccttta tcatatcaat gattatcatg    3960
gttctattgc gcctctctac cttcttcccc agacgatccc tgtttgtctt tcgcttcaca    4020
acgccgaatt tcagggtctc tggcccatgc gcacacaaaa ggaaagggat gaggtttgct    4080
ctgttttcaa tatcgacgtc gatgtcgcca ggcgatatgt ccaatttggc gaagtttta    4140 acatgctcca tgccggtgct agctaccttc gtgtccacca acaagggttc ggcgctgtag    4200
gtgtttccag gaaatatgga aaacgctcgt acgcgcgcta tcccatcttc tggggtctca    4260
agaaggttgg gaatcttccg aacccagatc cttctgacac ggctgaatgg aacaaggaac    4320
tgcctaaaga aagtgagatc caggtagacc agaactacga ggcaagcagg gcagagctga    4380
aacggcaagc gcaggaatgg gcgggccttg aacaaaaccc taatgctgac cttatggttt    4440
tcgtgggacg gtggtcgatg cagaaaggaa tcgatctgat agctgatgtt atgcccgctg    4500
ttttggaggc tcatcccaat gttcagctga tctgtgtcgg cccagtcatt gacctttatg    4560
gaaaatttgc cgccctgaag cttgaccgga tgatgcagct ctaccctggg cgtgtgttct    4620
caaagcccga gtttacagca cttcctccat acatattttc aggagcggag tttgccttga    4680
tcccatcccg tgacgaaccg ttcggactgg ttgccgttga atttggtcgc aagggagcct    4740
tgggaatcgg tgcacgtgtt ggagggcttg ccagatgcc gggttggtgg tataatgttg    4800
aatcaacaac tactgcccat ctgcttcatc aatttaaact agctatcgga gtgccttga    4860 actcgaaacc ccaagttagg gcaaggatgc gtgcaagatc tgcaaagcag cgtttccctg    4920
ttgctcaatg ggttgaggac ctcgagattc tacagtcaac ggccatgcga atccacagca    4980
aaggcttggc taaggcgagc gtccagccct ataactcagg aagcaacacc ccacttggca    5040
tgatgacgcc cccttattgcg tcgactggga ctgttacccc gacgggaatc cagacacctc    5100
ctcttgccca ttcgcgatca ggaagctact caaacatcaa ccgcctcagt gcttatgggc    5160
ctcagcaacg taacacgata atctacagcc gagacccaag cccaggcggc gaagaccagc    5220
ctagatctgg tattcgacag ttatcacttg gtgttagggc tgggcctgga catcttatgc    5280
gtcgtggccg ccgcaggttg agaagaaata gccacgcggg gacggacgag aacgccagcg    5340
tctccatgac ggaggagagt agcgacgacg atataatccc aagtttctac ggggaagagg    5400
agtacacgct taccctgaa caggctgagg aagtacgtcg cgcagatatg acaccacagc    5460
aggaacagaa tcatggctcg gttagggact tctttacccg tcgtcactcg agtcagagct    5520
cgattttgtc tcgtagtgtt ttgtctccag ccagttcgac tacgtttgac ggggacgaga    5580
ccttcgttcc acccgcacca ccgtttgcag aacctggaaa ccgtctcagc agtgcgtcgg    5640
tactctctgt tgactcagta gtgggcgaga agaaagatta caaactgcaa aaagttgatc    5700
ctacatttac cgatagcact ggcgaattct acaaggtttt tgaaagaaaa ctagaaaagc    5760
tcaatggctc gaactccatc tcccaacttt gcatcgagga atatctggag aagagcgaaa    5820
agaaatggtt tgaccgattc cgtgatgcac gacttggccg caaacagtcc ccgtcgtctt    5880
ccattttccg caccaagttt gaaggctcct cgcctatggc actcgtatca aacgatgaag    5940
tcggatcgcg cgcgagtgga agcgagcccc gtatgaggcc tgacgaattt tgtcttggaa    6000
acgactatgt tcctccctct gggctcaaga agtggatgca agttcggatt tcgactggc    6060 ccatttactc cttcattctc ggactgggcc aaattatagc agcgaactct taccagatca    6120
```

-continued

```
ccttgttgac tggagaagtc ggccagcggc ctgagaagct ctatggtatt gcaacagtat    6180
acctcgtgag ctctatagtc tggtggtttc ttttccgctt ttgcaaatct gtcgtggtac    6240
tgtctctgcc ctggctgttc tacggtttcg cctttgttct tattggagtc gcacactatg    6300
agggcgatag cttcgctcgt gcttggatcc agaacgttgg agccggtgta tacgccgctg    6360
catcagccag tggctcattg ttttctcgccc ttaacttcgg agacgaaaac ggtgcaccag    6420
tcaagaattg ggtgtggcgt gcttgcatca tacaaggtac ccagcaagcc tacatcatcg    6480
gtctttggta ctgggggact tctatatcgc aagcagtcac cagaggcgtt ccggatgttc    6540
aagcccatat cacggagaca tggagaatga cgtacgtgcc tccatactct caacggtcc    6600
tttactaact ctatattgca gtactatctg tatgccgata gcagtctttc tctgggtact    6660
cggcatcctt gtcttctttg cctaccaaa ctattaccgc cagacgcctg aaaagtccc    6720
ttcgttctac caatctgtct gccgtcggaa gatcatcctc tggaacttcg tagtggtcat    6780
tctgcaaaat ttcttcctca cgccccccta cggacgaaac tggagctgta agtcccaaaa    6840
aaatcacttt attgttccga actaaacta aggaaacagt cctctggagc tccgtccacg    6900
cggaaccctg gcacatcggc cttctggtcg tcgccttctt cggagtcgcc tgggttctca    6960
tcctctgtat cttcgcccgg cttttccaaat cccacagttg gatcctcccc gttttttgcct    7020
gcggtcttgg tgccccgcga tgggcacaga tctggtgggg ggtctcggga atgggcttat    7080
tcctcccttg ggcaggaagc tacacgaccg gcgcactagt atctcgctct ctctggctat    7140
ggctgggtat tctcgactcc ctgcaaggct taggctttgg tatgattcta ttacaaacac    7200
tcacacggat gcatatctgc ttcacgcttt tggcgagtca agtcctaggc tctattgcga    7260
cgatctgcgc caggggcttttt gcgccgaata atatcgggcc agggcccatc tctcctgata    7320
ttacggatgg agcgggcgcc gttgcaaacg cgtggttctg gattgcgttg ttcttccagt    7380
tgttgattgt gtatgtcttc ctactatata attggagcct agtgggacgt aaactaatag    7440
ttcgatctag tgctgggttc ctcatgttct tccggaaaga gcagcttacg aaaccctaaa    7500
taccatcgca actcgacctc gccattgcca ttacctgggt tacttttgtca attcttgaca    7560
taatcactac agccggtaat ctaccgggtg gcgccccatt gcctgacaat cttgctctcg    7620
aatctctcca ttgtcccatc agcctattta ctctaccctt tattgatctt gctgtccatc    7680
gacagaccgt gcatatttgc aacttcttga cgatatttga cctcacctct gaacgaaaa    7740
gaatgactgc tatgagtcaa cctaatgatt ggatgttata tggtctctta ttcttctatg    7800
gaactgactt atcattgtgc ccgccatgac gtgatttgat gtgggtgaga tgtgggtgat    7860
atgtacctaa tgatactact ttgttgatta gttccttccc tattgatgtt atgtcataa    7919
```

<210> SEQ ID NO 3
<211> LENGTH: 2434
<212> TYPE: PRT
<213> ORGANISM: Aspergillus nidulans

<400> SEQUENCE: 3

Met Gly Arg Leu Gln Leu Ser Ser Gly Leu Lys Ala Ile Ala Leu Leu
1               5                   10                  15

Thr Phe Ala Ala Thr Ala Thr Cys Trp Pro Tyr Asp Glu Ser Leu Val
            20                  25                  30

Asp Tyr Asn Val Asn Thr Asn Lys Ser Ala Thr Asn Pro Ala Asp Tyr
        35                  40                  45

Trp Gly Glu Trp Ser Asp His Lys Tyr His Pro Ser Pro Glu Asn Trp

-continued

```
            50                  55                  60
Arg Phe Pro Phe Tyr Thr Leu Phe Met Asp Arg Phe Val Asn Gly Asp
 65                  70                  75                  80

Pro Thr Asn Asp Asn Ile Asn Gly Thr Thr Phe Glu His Asp Leu Asn
                     85                  90                  95

Ser Asn Gln Met Arg His Gly Gly Asp Val Ala Gly Leu Val Asp Thr
                100                 105                 110

Leu Asp Tyr Leu Gln Gly Met Gly Ile Lys Gly Leu Tyr Leu Ala Gly
                     115                 120                 125

Thr Pro Leu Met Asn Gln Pro Trp Gly Ser Asp Gly Tyr Ser Ala Leu
                130                 135                 140

Asp Thr Thr Leu Leu Asp Gln His Phe Gly Thr Ile Gln Val Trp Arg
145                 150                 155                 160

Asp Ala Ile Thr Glu Ile His Lys Arg Gly Ile Leu Gly Asp Leu Ile
                     165                 170                 175

Gly Phe Glu Gly His Leu Asn Asp Thr Thr Pro Phe Ser Glu Lys Glu
                180                 185                 190

His Lys Ala Leu Trp Lys Ser Asn Arg Arg Tyr Val Asp Phe Asp Ile
                     195                 200                 205

Gly Asn Thr Tyr Asn Ala Thr Cys Asp Tyr Pro Arg Phe Trp Tyr Glu
                210                 215                 220

Asp Gly Met Pro Val Asn Glu Ser Leu Thr Ala Gly Leu Val Gly Cys
225                 230                 235                 240

Tyr Asp Ser Asp Phe Asp Gln Tyr Gly Asp Ile Glu Ala Phe Gly Val
                     245                 250                 255

Trp Pro Asp Trp Lys Arg Gln Leu Ala Lys Phe Ala Ser Val Gln Asp
                260                 265                 270

Arg Leu Arg Glu Trp Tyr Pro Pro Val Arg Glu Arg Leu Ile Arg His
                     275                 280                 285

Thr Cys Met Ile Ile Ala Ser Phe Asp Ile Asp Gly Ile Arg Tyr Asp
                290                 295                 300

Lys Ala Thr Gln Ala Thr Val Asp Ala Leu Gly Asp Met Ser Lys Ala
305                 310                 315                 320

Tyr Arg Glu Cys Ala Arg Ala Val Gly Lys Glu Asn Phe Phe Ile Ala
                     325                 330                 335

Gly Glu Ile Thr Gly Gly Asn Thr Phe Gly Ser Ile Tyr Leu Gly Arg
                340                 345                 350

Gly Arg Gln Ser Asn Gln Val Asp Ser Val Gly Asn Ile Tyr Asp Ala
                     355                 360                 365

Met Lys Leu Thr Asn Glu Ser Asp Pro Gln Leu Phe Leu Arg Glu Val
                370                 375                 380

Gly His Glu Ala Ile Asp Ala Gly Ala Phe His Tyr Ser Thr Tyr Arg
385                 390                 395                 400

Ala Leu Thr Arg Phe Leu Gly Met Asp Gly Gln Leu Glu Ala Gly Tyr
                     405                 410                 415

Asp Val Pro Leu Asp Trp Val Gln Ala Trp Gly Asn Met Thr Val Thr
                420                 425                 430

Asn Asp Leu Ile Asn Ala Asn Thr Gly Lys Phe Asp Pro Arg His Met
                     435                 440                 445

Tyr Gly Val Thr Asn Gln Asp Val Phe Arg Trp Pro Ala Ile Glu Trp
                450                 455                 460

Gly Val Glu Arg Gln Met Leu Gly Ser Phe Ile Thr Thr Leu Met Leu
465                 470                 475                 480
```

```
Pro Gly Ile Pro Leu Leu Trp Gly Glu Glu Ala Phe Tyr Val
            485             490             495

Leu Asp Ala Thr Ala Ser Asn Tyr Ile Tyr Gly Arg Gln Ala Met Ser
            500             505             510

Ser Ala Thr Ala Trp Lys Thr His Gly Cys Phe Ser Leu Glu Ser Ser
            515             520             525

Gln Tyr Tyr Gln Trp Pro Leu Val Ala Ala Leu Asp Gly Cys Asn Asp
    530             535             540

Glu Thr Val Thr Tyr Asp His Arg Asp Pro Ser His Pro Val Arg Asn
545             550             555             560

Ile Ile Lys His Met Tyr Gln Met Arg Glu Gln Tyr Pro Met Leu Asn
                565             570             575

Asp Gly Phe Ile Ile Glu Thr Leu Ser Asn Gln Thr Glu Pro Val Tyr
                580             585             590

Tyr Pro Gly Ser Asn Gly Thr Glu Thr Glu Thr Gly Met Trp Ser Val
            595             600             605

Arg Arg Asp Arg Asn Glu Glu Thr Gln Asp Phe Gly Ser Ser Asp Asp
            610             615             620

Asn Glu Pro Ile Trp Leu Val Tyr Ser Asn Met Asn Arg Thr His Asp
625             630             635             640

Tyr Thr Phe Asp Cys Ser Asp Asn Glu Thr Ala Leu Ile Ala Ala Phe
                645             650             655

Pro Ser Gly Thr Lys Val Arg Asn Leu Phe His Pro Tyr Asp Thr Leu
            660             665             670

Thr Leu Gly Asp Gly Pro Lys Glu Met Val Tyr Gly Asn Ser Thr Glu
            675             680             685

Leu Val Gly Cys Leu Pro Asn Leu Thr Leu Ser Arg Tyr Glu Phe Arg
    690             695             700

Ala Tyr Val Lys Asn Glu Leu Trp Lys Lys Pro Arg Pro Met Ile Thr
705             710             715             720

Lys Phe Gln Pro Gly Asp Asp Glu Ala Asn Gly His Asp Ser Pro Leu
                725             730             735

Arg Ser Thr Val Ala Pro Asp Ala Ser Glu Thr Val Arg Leu Thr Leu
            740             745             750

Gln Phe Ser Glu Ala Met Gly Cys Asp Ser Val Thr Asp Ser Ile Ser
            755             760             765

Phe Asn Ser Ser Thr Glu Thr Gly Lys Ile Pro Ser Ile Asp Ala Ser
    770             775             780

Thr Val Gln Cys Gly Asn Ile Thr Glu Val Ala Asn Ser Asn Ala Thr
785             790             795             800

Gly His Ile Pro Gly Lys Trp Gln Trp Ala Ala Asp Leu Arg Gly Val
                805             810             815

Tyr Asn Gly Ile His Arg Val Thr Val Asn Asn Ala Ser Asn Ala Asp
                820             825             830

Gly Asp Asp Ser Thr His Ala Val Asp His Phe Leu Phe Arg Ile Gly
            835             840             845

Gln Ile Asp Asn Pro Met Val Phe Thr Ser Ala Asn Tyr Ser Ser Ser
    850             855             860

Leu Leu His Glu Lys Glu Asp Gly Thr Phe Tyr Ile Gln His His Ala
865             870             875             880

Ala Gly Ala Asp Lys Tyr Arg Tyr Ser Thr Asn Trp Gly Thr Thr Phe
                885             890             895
```

```
Ser Asp Trp Lys Thr Tyr Lys Gly Gly Asn Asp Thr Ile Thr Met Leu
            900                 905                 910

Pro Trp Asn Gly Thr Lys Ala Gln Glu Trp Glu Gly His His Ile Arg
        915                 920                 925

Val Glu Tyr Trp Ser Arg Trp Thr Gly Ser Ser Ser His Val Gln Glu
    930                 935                 940

Gly Asp Ser Gly Trp Lys Tyr Lys Thr Pro Arg Arg Phe Pro His Ala
945                 950                 955                 960

Phe Phe Asn Gly Pro Tyr Asn Gln Tyr Gly Tyr Asp Gly Gly Leu Asp
                965                 970                 975

Asn Gln Ile Lys Leu Asp Ala Gly Ala Gly Gly Asp Gly Tyr Trp Lys
            980                 985                 990

Tyr His Phe Thr Ser Glu Trp Pro Ala Val Gly Gln Val Asn Val Trp
        995                 1000                1005

Gly Ile Asn Pro Asp Gly Glu Pro Asp Gln Ser Trp Val Met Gly
    1010                1015                1020

Asp Val Asp Gly Asp Lys Val Leu Asp Arg Met Pro Pro Ser Ala
    1025                1030                1035

Leu Ser Ala Thr Leu Ile Asn Ile Thr Asp His Pro Thr His Pro
    1040                1045                1050

Tyr Ile Ser Trp Lys Leu Tyr Ile Asn Asp Ala Thr Met Arg Tyr
    1055                1060                1065

Tyr Leu Ile Pro Ala Gly His Gln Ser Gly Gln Ile Ala Met Phe
    1070                1075                1080

Val Leu Phe Trp Ile Ile Pro Leu Leu Ser Gly Ser Ala Cys Val
    1085                1090                1095

Tyr Ile Phe Met Lys Ser Phe Tyr Lys Val Lys Phe Asn Glu Ile
    1100                1105                1110

Gly Ala Ala Gly Ala Ser Thr Glu Met Lys Ser Leu Val Pro Leu
    1115                1120                1125

Ala Leu Arg Arg Arg Met Lys Gln Leu Ala Ser Gly Asn Gly Lys
    1130                1135                1140

Asn Gly Pro Ser Phe Asn Pro Leu Met Arg Leu Ala Glu Lys Ser
    1145                1150                1155

Gly Phe Met Gln Ser Thr Thr Ala Leu Ala Gly Ala Ala Ser Gly
    1160                1165                1170

Lys Arg Arg Met Val Leu Ile Ala Thr Met Glu Tyr Asp Ile Glu
    1175                1180                1185

Asp Trp Gly Ile Lys Ile Lys Ile Gly Gly Leu Gly Val Met Ala
    1190                1195                1200

Gln Leu Met Gly Lys Thr Leu Gly His Gln Asp Leu Ile Trp Val
    1205                1210                1215

Val Pro Cys Val Gly Gly Val Asp Tyr Pro Val Asp Thr Pro Ala
    1220                1225                1230

Glu Pro Met Thr Val Thr Ile Leu Gly Gln Ala Tyr Gln Val Asn
    1235                1240                1245

Val Gln Tyr His Val Leu Lys Asn Ile Thr Tyr Val Leu Leu Asp
    1250                1255                1260

Ala Pro Val Phe Arg Gln Gln Thr Lys Ser Glu Pro Tyr Pro Ala
    1265                1270                1275

Arg Met Asp Asp Leu Asp Ser Ala Val Tyr Tyr Ser Ala Trp Asn
    1280                1285                1290

Gln Cys Ile Ala Glu Ala Ile Lys Arg Phe Pro Val Asp Leu Tyr
```

-continued

```
            1295                1300                1305

His Ile Asn Asp Tyr His Gly Ser Val Ala Pro Leu Tyr Leu Leu
            1310                1315            1320

Pro Gly Thr Ile Pro Ala Cys Leu Ser Leu His Asn Ala Glu Phe
            1325                1330            1335

Gln Gly Leu Trp Pro Met Arg Thr Gln Lys Glu Lys Glu Glu Val
            1340                1345            1350

Cys Ser Val Phe Asn Leu Asp Val Glu Val Arg Asn Tyr Val
            1355                1360            1365

Gln Phe Gly Glu Val Phe Asn Leu Leu His Ala Gly Ala Ser Tyr
            1370                1375            1380

Leu Arg Val His Gln Gln Gly Phe Gly Ala Val Gly Val Ser Lys
            1385                1390            1395

Lys Tyr Gly Lys Arg Ser Tyr Ala Arg Tyr Pro Ile Phe Trp Gly
            1400                1405            1410

Leu Arg Lys Ile Gly Asn Leu Pro Asn Pro Asp Pro Ser Asp Val
            1415                1420            1425

Gly Glu Trp Thr Lys Glu Asp Ser Leu Ile Lys Asp Glu Asp Ile
            1430                1435            1440

Lys Val Asp Pro Glu Phe Glu Ala Gly Arg Ala Glu Leu Lys Arg
            1445                1450            1455

Gln Ala Gln Glu Trp Ala Gly Leu Asp Gln Asn Pro Asp Ala Asp
            1460                1465            1470

Leu Leu Val Phe Val Gly Arg Trp Ser Met Gln Lys Gly Val Asp
            1475                1480            1485

Leu Ile Ala Asp Val Met Pro Ala Val Leu Glu Ala Arg Pro Asn
            1490                1495            1500

Val Gln Leu Ile Cys Val Gly Pro Val Ile Asp Leu Tyr Gly Arg
            1505                1510            1515

Phe Ala Ala Leu Lys Leu Asp Arg Met Met Lys Val Tyr Pro Gly
            1520                1525            1530

Arg Val Phe Ser Arg Pro Glu Phe Thr Ala Leu Pro Pro Tyr Ile
            1535                1540            1545

Phe Ser Gly Ala Glu Phe Ala Leu Ile Pro Ser Arg Asp Glu Pro
            1550                1555            1560

Phe Gly Leu Val Ala Val Glu Phe Gly Arg Lys Gly Ala Leu Gly
            1565                1570            1575

Ile Gly Ala Arg Val Gly Gly Leu Gly Gln Met Pro Gly Trp Trp
            1580                1585            1590

Tyr Asn Val Glu Ser Val Ser Thr Ser His Leu Leu Met Gln Phe
            1595                1600            1605

Lys Leu Ala Ile Glu Ala Ala Leu Ser Ser Lys Thr Glu Thr Arg
            1610                1615            1620

Ala Met Met Arg Ala Arg Ser Ala Lys Gln Arg Phe Pro Val Ala
            1625                1630            1635

Gln Trp Val Glu Asp Leu Glu Ile Leu Gln Ser Thr Ala Ile Gln
            1640                1645            1650

Val His Glu Lys Glu Val Ser Arg Gly His Ala Gly Gly Arg Pro
            1655                1660            1665

Met Thr Pro Met Thr Pro Ser Gly Ala Thr Thr Pro Ser Gly Met
            1670                1675            1680

Met Thr Pro Thr Thr Gly Ser Arg Gly Leu Lys Pro Leu Ser Gln
            1685                1690            1695
```

Gly Val Gly Met Gly Leu Ser Val Pro His Ser Arg Glu Ser Ser
1700                1705                    1710

Tyr Ser Asn Leu Asn Arg Leu Ser Glu Tyr Val Ala Gln Lys Thr
1715                1720                    1725

Pro Gly Glu Ser Gln Pro Arg Glu Ser Ser Gly Leu Gln Arg Ser
1730                1735                    1740

Leu Ser Leu Gly Val Arg Ser Gly Pro Gly His Arg Gly Arg Ala
1745                1750                    1755

Arg Lys Gln Lys Pro Gly Ala Asp Asn Ile Pro Glu Gly Asn Glu
1760                1765                    1770

Asp Gly Ser Ser Ser Asp Thr Glu Ser Ile Pro Asp Tyr Tyr Asp
1775                1780                    1785

Asp Glu Tyr Thr Leu Thr Pro Ala Gln Ile Glu Glu Ser Arg Arg
1790                1795                    1800

Ala Gln Ala Thr Arg Ser Ile Ser Phe Ser Pro Glu Thr Leu Gln
1805                1810                    1815

Pro Pro Arg Ser Pro Leu Pro Ala Pro Pro Met Ser Pro Gly Thr
1820                1825                    1830

Pro Pro Ser Val Glu Gln Thr Leu Leu Pro Pro Pro Lys Pro Phe
1835                1840                    1845

Ala Ala Ala Asp Ala Gly Asn Arg Leu Ser Ser Ala Ser Val Leu
1850                1855                    1860

Ser Leu Asp Ser Val Val Gly Gly Lys Lys Asp Phe Lys Leu Gln
1865                1870                    1875

Lys Val Asp Pro Phe Phe Thr Asp Ser Asn Gly Glu Tyr Ala Arg
1880                1885                    1890

Asn Phe Glu Gln Gln Leu Glu Asn Leu Asn Gly Ser Asn Ser Glu
1895                1900                    1905

Ser Gln Leu Cys Ile Glu Glu Phe Leu Val Lys Ser Glu Arg Arg
1910                1915                    1920

Trp Phe Asn Lys Phe Arg Asp Ala Arg Leu Gly Arg Leu Arg Ser
1925                1930                    1935

Pro Thr Pro Ser Val Phe Arg Asp Asn His Ser His Gly Arg Gly
1940                1945                    1950

Ser Pro Asp Gly Ser Met Tyr Val Asp Glu Ala Gly His Arg Asn
1955                1960                    1965

Ser Gly Asp Ala Val His Asp Asn Gly Ser Asp Thr Asp Asp
1970                1975                    1980

Glu Phe Leu Leu Gly Lys Asp Tyr Val Pro Pro Thr Gly Leu Lys
1985                1990                    1995

Lys Trp Met Gln Ile Lys Ile Gly Asp Trp Pro Val Tyr Thr Leu
2000                2005                    2010

Phe Leu Ala Leu Gly Gln Ile Ile Ala Ala Asn Ser Tyr Gln Ile
2015                2020                    2025

Thr Leu Leu Thr Gly Glu Val Gly Gln Thr Ala Glu Lys Leu Tyr
2030                2035                    2040

Gly Ile Ala Thr Thr Tyr Ala Ile Thr Ser Ala Leu Trp Trp Leu
2045                2050                    2055

Val Phe Arg Tyr Phe Lys Ser Ile Val Cys Leu Ser Thr Pro Trp
2060                2065                    2070

Phe Leu Tyr Gly Ile Ala Phe Leu Phe Ile Gly Ser Ala His Phe
2075                2080                    2085

-continued

| | | | | | | | | | | | |
|---|---|---|---|---|---|---|---|---|---|---|---|
| Glu | Ser | Asp | Ser | Phe | Thr | Arg | Gly | Trp | Ile | Gln | Asn | Val | Gly | Ser |
| 2090 | | | | | 2095 | | | | | 2100 | | | | |

Glu Ser Asp Ser Phe Thr Arg Gly Trp Ile Gln Asn Val Gly Ser
    2090                2095                2100

Gly Phe Tyr Ala Ala Ala Ser Ser Ser Gly Ser Ile Phe Phe Ala
    2105                2110                2115

Leu Asn Phe Gly Asp Glu Gly Gly Ala Pro Val Ser Lys Trp Ile
    2120                2125                2130

Phe Arg Ala Cys Val Ile Gln Gly Ile Gln Gln Val Tyr Val Ile
    2135                2140                2145

Val Leu Trp Tyr Trp Gly Ser Thr Met Ala His Gln Ser Ser Gln
    2150                2155                2160

Gly Leu Leu Thr Ala Asp Asn Thr Ile Ser Asn Thr Trp Lys Met
    2165                2170                2175

Thr Ala Ile Cys Tyr Pro Ile Ala Met Leu Leu Trp Ala Ile Gly
    2180                2185                2190

Leu Leu Leu Ile Phe Gly Leu Pro Asn Tyr Tyr Arg Gln Lys Pro
    2195                2200                2205

Gly Lys Val Pro Ser Phe Tyr Lys Ser Leu Phe Arg Arg Lys Ile
    2210                2215                2220

Val Leu Trp Asn Phe Val Ala Val Ile Leu Gln Asn Phe Phe Leu
    2225                2230                2235

Ser Ala Pro Tyr Gly Arg Asn Trp Ser Phe Leu Trp Thr Ser Ser
    2240                2245                2250

His Thr Lys Pro Trp Gln Ile Val Ile Leu Cys Val Ile Phe Phe
    2255                2260                2265

Gly Leu Leu Trp Cys Ala Phe Leu Tyr Ile Val Ala Val Leu Ser
    2270                2275                2280

Lys Gln His Ser Trp Phe Leu Pro Val Phe Ala Cys Gly Leu Gly
    2285                2290                2295

Ala Pro Arg Phe Leu Gln Ile Trp Trp Gly Val Ser Gly Ile Gly
    2300                2305                2310

His Tyr Leu Pro Trp Val Ala Gly Gly Tyr Thr Gly Gly Ala Leu
    2315                2320                2325

Val Ser Arg Ser Ile Trp Leu Trp Leu Gly Val Leu Asp Ser Ile
    2330                2335                2340

Gln Gly Leu Gly Phe Gly Ile Ile Leu Leu Gln Thr Leu Thr Arg
    2345                2350                2355

Met His Met Cys Phe Thr Leu Ile Val Ser Gln Val Leu Gly Ser
    2360                2365                2370

Ile Ala Thr Ile Val Ala Arg Ala Cys Ala Pro Asn Asn Val Gly
    2375                2380                2385

Pro Gly Pro Val Ser Pro Asp Ile Thr Lys Gly Ala Gly Glu Leu
    2390                2395                2400

Ala Asn Ala Trp Phe Trp Val Ala Leu Phe Cys Gln Leu Leu Val
    2405                2410                2415

Cys Ala Gly Phe Leu Leu Phe Phe Arg Lys Glu Gln Leu Ala Lys
    2420                2425                2430

Pro

<210> SEQ ID NO 4
<211> LENGTH: 7537
<212> TYPE: DNA
<213> ORGANISM: Aspergillus nidulans

<400> SEQUENCE: 4

-continued

| | |
|---|---|
| atggggaggc tccagctctc aagcgggctg aaggccatag ccctgctcac attcgcagcg | 60 |
| acagcaacat gctggccata cgacgagtcc ctcgttgact acaacgtcaa cacgaataag | 120 |
| tcggccacta accccgccga ctactgggga gaatggtcgg atcacaagta ccatccgtcg | 180 |
| ccagagaact ggcggtttcc gttttacaca ctcttcatgg acagattcgt gaatggggat | 240 |
| ccaacaaatg ataacatcaa cgggaccacg tttgagcacg atctcaattc aaatcagatg | 300 |
| cgtcatggcg gtgatgttgc tgggctggtt gatacgctgg attacttgca agggatgggg | 360 |
| atcaaggtgc gttgccgcta ttattcgtca atttctggta agatatagt tgatgctaac | 420 |
| gatgcgatag ggactgtacc ttgctggaac tccgctcatg aaccagccct ggggctcgga | 480 |
| tgggtattcg gcgctcgaca ccacccttct cgaccagcac tttggcacga tccaggtctg | 540 |
| gcgcgacgcc atcaccgaaa tccacaaacg ggggatgtac gttctgttcg acaatacaat | 600 |
| cgctacgtga gtacctcgcc tccctgcgtt ttgccatcgg tttgtaaaaa acttgggcct | 660 |
| gacactagat tactgcagcc tcggtgatct cattggtttt gaaggtcatc tcaacgacac | 720 |
| cacgcccttc tccgagaaag aacacaaggc cctttggaag tccaacagac ggtacgtcga | 780 |
| tttcgatatt ggcaacacct acaacgccac ctgtgattat ccgcgcttct ggtacgagga | 840 |
| cgggatgcca gtcaatgagt ccctgaccgc gggcctggtc gggtgttatg atagtgactt | 900 |
| tgaccagtac ggtgacatcg aagcgttcgg tgtctggcca gactggaagc gtcaactggc | 960 |
| gaagtttgcg tccgtccagg atcggttgag agaatggtac ccacctgtac gggaacggct | 1020 |
| gatccgacac acatgcatga tcattgcctc ctttgatatc gacggtattc ggtacgacaa | 1080 |
| ggcgacccag cgcactgtcg atgcgttggg ggacatgtcc aaagcgtatc gggaatgcgc | 1140 |
| gcgggctgtc ggcaaggaga acttttttcat tgcgggtgag atcacaggag caatacttt | 1200 |
| tgggtctatc tatctcggac gaggacggca gtcgaaccag gtcgattcgg tgggaatat | 1260 |
| ctacgacgcc atgaaactga caaacgagtc ggatccgcag cttttcctgc gcgaggtcgg | 1320 |
| ccacgaggct atcgacgccg gtgccttcca ttactcgact taccgtgccc tgacccgctt | 1380 |
| cctgggaatg gacgggcagc tggaggccgg ttatgacgtc cctcttgact gggtgcaggc | 1440 |
| atggggaaac atgaccgtga ccaacgacct gattaacgcc aacacgggca agttcgatcc | 1500 |
| ccggcacatg tacggcgtga caaaccagga tgttttccgt tggccggcaa tcgagtgggg | 1560 |
| tgttgagagg cagatgctgg gctcgtttat caccacgctg atgctgccgg catcccgct | 1620 |
| gctgctttgg ggagaggagc aagcgttcta cgtgctcgat gcgacggcgt caaactacat | 1680 |
| atatggacga caggccatgt cgtctgcgac cgcgtggaag acgacggct gcttctcact | 1740 |
| cgaatcgagc cagtactacc agtggcccct ggtggccgca ctcgacggtt gcaacgacga | 1800 |
| gacggtcacc tacgaccacc gggacccgag ccacccggtg cgcaacatca tcaagcacat | 1860 |
| gtaccagatg cgcgagcagt acccaatgct caacgatggg ttcatcatcg agaccctttc | 1920 |
| taaccagacg gaacctgtct actaccccgg ttccaacggg accgagaccg agacaggcat | 1980 |
| gtggtcggtc cgccgtgacc ggaacgaaga gacccaggac tttggctcga gtgacgacaa | 2040 |
| cgaacccatc tggctagtct atagcaacat gaaccgcacg cacgactaca catttgattg | 2100 |
| ctctgacaat gagacggcac tcattgccgc cttcccctca ggcaccaagg tcaggaacct | 2160 |
| cttttcacccg tacgacacgc tgaccctagg cgacgggcca aaggaaatgg tctatggcaa | 2220 |
| ctcgactgag ctggtaggct gcttaccgaa cctgacgctt agccggtacg agttccgtgc | 2280 |
| ctatgtcaag aacgagctct ggaaaaagcc cggccgatg atcaccaagt ccagcccgg | 2340 |
| cgacgatgag gccaacggcc acgacagccc gctgcgttcg accgtcgcac cagatgcgtc | 2400 |

```
cgagacggtg cgactgacgc tgcagttttc tgaggcgatg ggatgcgatt ctgtcacaga    2460
ctccatctca tttaactctt ccacggaaac cggcaagatt ccatccatcg acgcctccac    2520
cgtccagtgt gggaacatca ctgaagtcgc aacagcaac gctaccgggc acatccccgg     2580
taagtggcag tgggctgcag atctgagagg ggtgtacaac ggcatccacc gggtcactgt    2640
caacaacgcc agcaacgccg acggggacga ctccacccac gcagtcgacc acttcctctt    2700
ccggattggg cagattgaca accccatggt ctttacctct gccaactact ccagcagttt    2760
gctgcatgag aaggaggacg gcacgttcta tatccaacac cacgctgccg gtgctgacaa    2820
gtaccgctat tcgacgaatt ggggcaccac gttctctgac tggaaaacgt acaagggagg    2880
taacgacacg attaccatgc ttccatggaa tggcactaag gcgcaggaat gggagggaca    2940
tcacatccgc gtcgagtact ggtcccgctg gactggcagc agtagccacg tccaggaagg    3000
cgattccggc tggaagtaca agacgccacg tcgcttccca catgcctttt tcaatgggcc    3060
ctacaaccag tacgggtacg acggcggtct ggacaaccag atcaagctgg acgcgggcgc    3120
cggcggcgac ggatactgga agtaccattt cacctcggag tggcctgccg tcgggcaggt    3180
gaatgtctgg ggcatcaatc cggatggcga gcccgatcag agctgggtga tgggcgacgt    3240
ggacggggac aaggtcctcg accgcatgcc accaagcgcg ctctctgcaa cgctgattaa    3300
catcactgat cacccaacgc acccttatat ctcgtggaag ctgtacataa acgacgcgac    3360
gatgcggtac tatctcatcc ccgctggcca ccagagcggg cagatcgcca tgttcgtcct    3420
cttctggatc atccctctcc tgtccggctc cgcctgcgtc tatatcttca tgaagtcctt    3480
ctacaaggtc aaattcaacg aaatcggcgc tgccggcgca agcacggaaa tgaagtcact    3540
tgtcccgctt gctctccgtc gacgcatgaa gcagctcgcc tctgggaatg gcaagaacgg    3600
tccgtcattc aacccgctca tgcgccttgc tgaaaagtcc ggctttatgc agagcacgac    3660
tgcgttggcc ggtgcggcct cgggcaagag acgcatggtc ctgatcgcga ccatggaata    3720
cgatattgaa gactggggga tcaagatcaa gatcggtggt ctgggagtga tggcccagct    3780
gatgggtaag acactcggcc accaggacct tatctgggtg gtgccttgtg tcggggggcgt    3840 ggactatcct gttgataccc ctgcggaacc catgacggtc actatcctgg gtcaggcata    3900
ccaggtgaac gtgcagtacc acgttctgaa gaacatcacg tacgtcttgc ttgacgcgcc    3960
cgtcttccgc cagcagacca gtcggagcc gtacccagcg cgcatggatg acttggactc    4020
tgcagtgtat tactccgcat ggaatcagtg tatcgcagag gcgatcaaac ggttccctgt    4080
tgatttgtac catattaacg attaccacgg ctctgtcgcg ccgctgtacc tcctgccagg    4140
taccatcccc gcctgtctgt cacttcacaa tgccgagttt cagggtctat ggccgatgcg    4200
aacacagaag gagaaagagg aggtctgttc cgtgttcaac ctggatgttg aggttgtccg    4260
caactacgtc cagtttggtg aggtgttcaa cctcctccac gcaggagcga gctatctccg    4320
cgttcaccaa cagggctttg gtgccgtcgg tgtctcgaag aagtacggca agcgttcata    4380
tgctcggtac ccgatcttct ggggcctgcg caagatcgga aacctgccga ccccgatcc    4440 gtctgatgtg ggcgagtgga cgaaggagga cagcctgatc aaggacgagg atatcaaggt    4500
ggatccagag tttgaagcag gccgcgctga gctcaagaga caggcgcagg agtgggctgg    4560
gctggaccag aaccctgatg ctgacctcct ggttttcgtc ggtcgttggt ccatgcagaa    4620
gggtgttgac cttatcgcag acgttatgcc cgcagtcctt gaagcacgac caaacgtaca    4680
gctcatctgt gttggacctg ttatcgatct ctatggccgc tttgcggcgc tcaagctcga    4740
```

-continued

```
ccgcatgatg aaggtgtatc ccggccgcgt cttctcacgc cctgaattca ctgccctgcc    4800
gccgtatatc ttctccggcg cggaattcgc gcttattccc tcccgtgacg aacccttttgg   4860
tcttgtcgcc gtcgagtttg gccgcaaagg tgcgctcggc attggagccc gtgttggtgg    4920
actgggacag atgcctggat ggtggtacaa tgtcgaatcg gtctcgacat cccatctcct    4980
catgcagttc aagctcgcta ttgaggctgc cctttcgtca aagactgaga cacgtgctat    5040
gatgcgtgct cgctctgcta acaacgctt ccccgttgcg cagtgggtgg aagatctgga     5100
gatcctacag tcgactgcta ccaggttca tgagaaggag gtttcccgtg tcatgcagg      5160
tggccgcccc atgacaccga tgacgccctc tggagctacg acgcccagcg gaatgatgac    5220
gcctactaca ggatcccgtg gtcttaagcc tctgtcccag ggcgtcggca tgggcctctc    5280
ggtgccacac tcccgggaga gcagctattc gaacctcaac cgattgagcg agtacgttgc    5340
gcaaaagact ccgggcgagt ctcaaccgcg agaatcgtcc ggtctgcagc gctcgctctc    5400
gctcggtgtc cggtccggtc ctggccaccg tggtcgtgcg cgcaagcaga aacccggcgc    5460
ggacaacatc ccggagggca acgaggacgg cagcagcagt gatactgagt ctatccctga    5520
ctactacgac gacgagtaca ccctcacccc agctcagatt gaagaaagca gacgggctca    5580
ggccacccgt tccatatcct tcagcccga gacactccag ccacctcgat ctcccctgcc     5640
cgcacctccc atgagtcccg ggacgccacc gtcggttgag cagactctgc tgcctccacc    5700
aaagcccttc gctgccgctg acgctggaaa cagacttagt agtgcatcag tgttatccct    5760
agactctgtc gtgggtggga agaaagactt caagctccaa aaggtcgacc ccttctttac    5820
tgacagcaac ggcgagtatg ctcggaactt cgaacagcag ctcgagaacc tcaacggctc    5880
caactccgag tcacagctgt gtatcgagga gttccttgtc aaatcggaac gccgctggtt    5940
caacaagttc cgcgatgcaa ggctgggtcg tctgcgctcg cccacaccgt ctgtcttccg    6000
cgacaaccac agccacggcc ggggctcgcc cgatggatct atgtatgtgg atgaggcagg    6060
ccaccgtaat agtggcgatg ccgtgcacga caacggctca gatgacacag acgatgagtt    6120
cctcctaggc aaagactacg tgcctcccac gggcctgaag aaatggatgc agatcaagat    6180
cggcgactgg ccggtgtaca cgctcttcct cgcactgggc cagatcatcg ctgcaaactc    6240
ctaccagatc acgctgctga caggcgaagt cggccaaaca gccgagaaac tgtacggaat    6300
tgccacaacc tatgccataa cctcagccct ctggtggctc gtcttccggt acttcaaatc    6360
catcgtctgc ctctccaccc cctggttctt gtatggaatt gcgttcctct tcattggctc    6420
cgcgcacttt gagtccgact cattcaccg cggctggatc cagaatgtcg gcagcggctt     6480
ctatgctgcg gcttcctcca gcggatccat cttctttgcg ctgaacttcg gtgatgaggg    6540
cggtgcacca gtgagcaagt ggattttccg tgcatgtgtg attcagggca tccagcaggt    6600
ctatgtcatt gtgctctggt attggggttc cacgatggca caccagtcca gccagggtct    6660
gctcacggcg gataatacga tctcaaatac gtggaagatg acgtacgtcc aaaacgaccc    6720
taaattaccc ccaattaata tacagaactc actaacaaac tgatacagcg ccatttgcta    6780
tccgatcgcc atgttactgt gggccatcgg cctcctgctg atcttcggcc taccaaacta    6840
ctaccgccag aaacccggca agtaccctc cttctacaaa tcccttttca gacgcaagat     6900
cgtgctctgg aactttgtcg ccgtcatcct acagaacttc ttcctgtcgg ctccctatgg    6960
ccgcaactgg agtttcctct ggacatcctc cacacaaag ccctggcaga ttgtcatcct     7020
gtgtgtcata ttctttggtc ttctgtggtg cgcgttcctt tacattgtcg ctgttctttc    7080
gaagcagcac tcctggtttt tgccagtctt cgcatgcggg ctcggcgccc ccgcttcct     7140
```

| | | |
|---|---|---|
| gcaaatctgg tggggtgttt ctggcatcgg acactacctt ccctggggttg ccggcgggta | 7200 | |
| tactggcggc gcactagtta gtcggagtat ctggctgtgg ctaggtgtgc tagattcaat | 7260 | |
| ccagggggtta gggttcggaa tcattctcct ccaaaccctg acccggatgc atatgtgctt | 7320 | |
| tacgttgatc gtcagccaag tcctgggatc tatagcaacc atcgttgcga gggcatgtgc | 7380 | |
| tccaaataat gttggtccgg gacctgtgag tccagatatc acgaagggag cgggcgaact | 7440 | |
| ggcgaacgcc tggttctggg ttgcattgtt ctgtcagttg cttgtctgtg ctgggttctt | 7500 | |
| actgttttc cgcaaggagc aacttgcgaa gccttaa | 7537 | |

```
<210> SEQ ID NO 5
<211> LENGTH: 22
<212> TYPE: DNA
<213> ORGANISM: Artificial
<220> FEATURE:
<223> OTHER INFORMATION: primer

<400> SEQUENCE: 5
agtggaggag ttagggagtg at                                             22

<210> SEQ ID NO 6
<211> LENGTH: 41
<212> TYPE: DNA
<213> ORGANISM: Artificial
<220> FEATURE:
<223> OTHER INFORMATION: primer

<400> SEQUENCE: 6
cacagggtac gtctgttgtg aaagagtaag gtagaagccc c                        41

<210> SEQ ID NO 7
<211> LENGTH: 40
<212> TYPE: DNA
<213> ORGANISM: Artificial
<220> FEATURE:
<223> OTHER INFORMATION: primer

<400> SEQUENCE: 7
ttcttctgag gtgcagttca gcagattatt acgcaccgga                          40

<210> SEQ ID NO 8
<211> LENGTH: 22
<212> TYPE: DNA
<213> ORGANISM: Artificial
<220> FEATURE:
<223> OTHER INFORMATION: primer

<400> SEQUENCE: 8
aaccgtggtt ttggtggcaa ag                                             22

<210> SEQ ID NO 9
<211> LENGTH: 39
<212> TYPE: DNA
<213> ORGANISM: Artificial
<220> FEATURE:
<223> OTHER INFORMATION: primer

<400> SEQUENCE: 9
taccttactc tttcacaaca gacgtaccct gtgatgttc                           39

<210> SEQ ID NO 10
<211> LENGTH: 39
<212> TYPE: DNA
```

```
<213> ORGANISM: Artificial
<220> FEATURE:
<223> OTHER INFORMATION: primer

<400> SEQUENCE: 10
gtaataatct gctgaactgc acctcagaag aaaaggatg                              39

<210> SEQ ID NO 11
<211> LENGTH: 22
<212> TYPE: DNA
<213> ORGANISM: Artificial
<220> FEATURE:
<223> OTHER INFORMATION: primer

<400> SEQUENCE: 11
gcaatgagag ctggaatcag tg                                                22

<210> SEQ ID NO 12
<211> LENGTH: 48
<212> TYPE: DNA
<213> ORGANISM: Artificial
<220> FEATURE:
<223> OTHER INFORMATION: primer

<400> SEQUENCE: 12
tgagtcggcc acagcggatg gaattcgtcg tctggctgtg agtgtaac                    48

<210> SEQ ID NO 13
<211> LENGTH: 47
<212> TYPE: DNA
<213> ORGANISM: Artificial
<220> FEATURE:
<223> OTHER INFORMATION: primer

<400> SEQUENCE: 13
tcttccagtt actccgtcgg tacccagcaa catgctggcc atacgac                     47

<210> SEQ ID NO 14
<211> LENGTH: 22
<212> TYPE: DNA
<213> ORGANISM: Artificial
<220> FEATURE:
<223> OTHER INFORMATION: primer

<400> SEQUENCE: 14
aaagtcctgg gtctcttcgt tc                                                22

<210> SEQ ID NO 15
<211> LENGTH: 26
<212> TYPE: DNA
<213> ORGANISM: Artificial
<220> FEATURE:
<223> OTHER INFORMATION: primer

<400> SEQUENCE: 15
gaattccatc cgctgtggcc gactca                                            26

<210> SEQ ID NO 16
<211> LENGTH: 30
<212> TYPE: DNA
<213> ORGANISM: Artificial
<220> FEATURE:
<223> OTHER INFORMATION: primer

<400> SEQUENCE: 16
ggtaccgacg gagtaactgg aaagatacga                                        30
```

<210> SEQ ID NO 17
<211> LENGTH: 25
<212> TYPE: DNA
<213> ORGANISM: Artificial
<220> FEATURE:
<223> OTHER INFORMATION: primer

<400> SEQUENCE: 17
gtacggtgta agctgctcgc tggac                                      25

<210> SEQ ID NO 18
<211> LENGTH: 25
<212> TYPE: DNA
<213> ORGANISM: Artificial
<220> FEATURE:
<223> OTHER INFORMATION: primer

<400> SEQUENCE: 18
tcctggatct tgtaaactga gtctc                                      25

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
aggaaagact gttggatgag                                            20

<210> SEQ ID NO 20
<211> LENGTH: 23
<212> TYPE: DNA
<213> ORGANISM: Artificial
<220> FEATURE:
<223> OTHER INFORMATION: primer

<400> SEQUENCE: 20
gacttattcg tgttgacgtt gta                                        23

<210> SEQ ID NO 21
<211> LENGTH: 37
<212> TYPE: DNA
<213> ORGANISM: Artificial
<220> FEATURE:
<223> OTHER INFORMATION: primer

<400> SEQUENCE: 21
tgaattcgcg gccgctattt atgatggtcg cgtggtg                         37

<210> SEQ ID NO 22
<211> LENGTH: 34
<212> TYPE: DNA
<213> ORGANISM: Artificial
<220> FEATURE:
<223> OTHER INFORMATION: primer

<400> SEQUENCE: 22
cttcttgagt gagctcacga gctactacag atct                            34

<210> SEQ ID NO 23
<211> LENGTH: 45
<212> TYPE: DNA
<213> ORGANISM: Artificial
<220> FEATURE:

<223> OTHER INFORMATION: primer

<400> SEQUENCE: 23
tgtagtagct cgtgagctca ctcaagaagc gtaacaggat agcct    45

<210> SEQ ID NO 24
<211> LENGTH: 25
<212> TYPE: DNA
<213> ORGANISM: Artificial
<220> FEATURE:
<223> OTHER INFORMATION: primer

<400> SEQUENCE: 24
gctatctaga ggcctgcagg agatc    25

<210> SEQ ID NO 25
<211> LENGTH: 22
<212> TYPE: DNA
<213> ORGANISM: Artificial
<220> FEATURE:
<223> OTHER INFORMATION: primer

<400> SEQUENCE: 25
tggtaagagt cgtcatatcg ag    22

<210> SEQ ID NO 26
<211> LENGTH: 36
<212> TYPE: DNA
<213> ORGANISM: Artificial
<220> FEATURE:
<223> OTHER INFORMATION: primer

<400> SEQUENCE: 26
tagcggccgc gaattcgatg aactagaagg atagag    36

<210> SEQ ID NO 27
<211> LENGTH: 2396
<212> TYPE: PRT
<213> ORGANISM: Aspergillus oryzae

<400> SEQUENCE: 27

Met Lys Trp Gly Phe Thr Gly Pro Leu Leu Ala Leu Leu Ala Ala Thr
1               5                   10                  15

Ala Ala Gly Trp Pro Tyr Asp Glu Ser Leu Val Asp Tyr Asn Leu Asn
            20                  25                  30

Val Asn Lys Asp Thr Thr Asn Pro Ala Glu Tyr Thr His Ala Glu Trp
        35                  40                  45

Lys Gly His Glu Tyr Asn Pro Ser Pro Lys Ser Trp Arg Phe Pro Phe
    50                  55                  60

Tyr Thr Leu Phe Ile Asp Arg Phe Val Asn Gly Asp Pro Thr Asn Asp
65                  70                  75                  80

Asn Ile Asn Gly Ser Leu Phe Glu His Asp Leu Asn Ser Asn Gln Met
                85                  90                  95

Arg His Gly Gly Asp Ala Ala Gly Leu Val Asp Thr Leu Asp Tyr Leu
            100                 105                 110

Gln Gly Met Gly Ile Lys Gly Ile Tyr Leu Ala Gly Thr Ile Leu Met
        115                 120                 125

Asn Gln Pro Trp Gly Ser Asp Gly Tyr Ser Ile Leu Asp Thr Thr Leu
    130                 135                 140

Leu Asp Gln His Tyr Gly Thr Ile Gln Thr Trp Arg Asp Ala Ile Thr
145                 150                 155                 160

```
Glu Ile His Lys Arg Gly Met Tyr Val Leu Phe Asp Asn Thr Ile Ala
            165                 170                 175

Thr Met Gly Asp Leu Ile Gly Phe Glu Gly Tyr Leu Asn Thr Thr Thr
            180                 185                 190

Pro Phe Ser Val Lys Glu His Lys Ala Leu Trp Lys Ser Asp Arg Gln
            195                 200                 205

Tyr Val Asp Phe Arg Phe Asp Asn Glu Tyr Asn Asn Thr Cys Glu Tyr
            210                 215                 220

Pro Arg Phe Trp Asn Glu Thr Gly Tyr Pro Val Asp Lys Asp Val Thr
225                 230                 235                 240

Asp Glu Leu Val Gly Cys Tyr Asn Ser Asp Phe Asp Gln Tyr Gly Asp
            245                 250                 255

Arg Glu Ala Phe Gly Val Tyr Pro Asp Trp Glu Arg Gln Leu Ala Lys
            260                 265                 270

Phe Ala Ser Val Gln Asp Arg Leu Arg Glu Trp His Pro Ser Val Lys
            275                 280                 285

Glu Arg Leu Ile Arg His Ser Cys Met Ile Ile Lys Ala Leu Asp Ile
            290                 295                 300

Asp Gly Phe Arg Tyr Asp Lys Ala Thr Gln Ala Thr Val Asp Ala Leu
305                 310                 315                 320

Gly Asp Met Ser His Ala Tyr Arg Glu Cys Ala Arg Ser Val Gly Lys
            325                 330                 335

Asp Asn Phe Phe Leu Pro Gly Glu Ile Thr Gly Gly Asn Asn Phe Gly
            340                 345                 350

Ser Ile Tyr Leu Gly Arg Gly Arg Gln Pro Asn Gln Tyr Pro Asp Ser
            355                 360                 365

Ser Leu Ala Ser Met Asn Leu Thr Asn Thr Ser Asp His Gln Tyr Phe
            370                 375                 380

Leu Arg Asp Asp Gly Leu Gln Ala Leu Asp Ser Ala Ala Phe His Tyr
385                 390                 395                 400

Ser Val Tyr Arg Thr Leu Thr Arg Phe Leu Gly Met Asp Gly Asn Leu
            405                 410                 415

Ala Ala Gly Tyr Asp Thr Pro Leu Asp Trp Thr Asp Ser Trp Asn Ile
            420                 425                 430

Met Val Leu Ser Asn Asp Met Ile Asn Ala Asn Thr Gly Lys Phe Asp
            435                 440                 445

Pro Arg His Met Tyr Gly Thr Thr Asn Gln Asp Val Phe Arg Trp Pro
450                 455                 460

Ala Ile Glu Leu Gly Val Glu Arg Gln Leu Leu Gly His Phe Ile Thr
465                 470                 475                 480

Thr Leu His Leu Pro Gly Ile Pro Ile Leu Leu Trp Gly Glu Glu Gln
            485                 490                 495

Ala Phe Tyr Ile Leu Asp Ser Thr Ala Asp Asn Tyr Ile Tyr Gly Arg
            500                 505                 510

Gln Ala Met Ser Pro Ser Thr Ala Trp Lys Thr His Gly Cys Tyr Ser
            515                 520                 525

Leu Gly Ser Ser Gln Tyr Tyr Asn Trp Pro Val Ser Ala Gly Arg Glu
            530                 535                 540

Gly Cys His Asp Glu Ala Val Ala Tyr Asp His Arg Asp Pro Ser His
545                 550                 555                 560

Pro Val His Asn Ile Ile Lys His Met Phe Gln Met Arg Gln Asp Phe
            565                 570                 575
```

```
Pro Val Leu Asn Asp Gly Tyr Ser Val Val Lys Leu Ser Lys Gln Thr
            580                 585                 590

Arg Glu Ile Gln Tyr Pro Gly Ser Asn Gly Thr Ala Thr Glu Val Gly
        595                 600                 605

Val Trp Ser Val Leu Arg Asp Leu Val Ser Asn Ile Gln Asp Phe Gly
    610                 615                 620

Asp Ser Gly Asn Asn Glu Pro Val Trp Leu Val Tyr Gln Asn Asp Asn
625                 630                 635                 640

Lys Thr Val Glu Tyr Ser Phe Asp Cys Gly Ser Asn Asp Ser Ala Leu
                645                 650                 655

Ile Ser Pro Phe Thr Gly Thr Thr Val Val Asn Leu Phe Tyr Pro
            660                 665                 670

His Asp Glu His Glu Leu Lys Asp Gly Pro Lys Ser Leu His Leu Asn
            675                 680                 685

Gly Thr Asn Ala Thr Asn Gly Cys Leu Asp Thr Leu Lys Leu Lys Pro
        690                 695                 700

Phe Glu Phe Arg Ala Tyr Val Pro Lys Ala Asn Phe Val Lys Pro Arg
705                 710                 715                 720

Pro Met Ile Thr Gln Phe Glu Pro Gly His Asp Val Pro Gln Leu Ser
                725                 730                 735

Lys Val Gly Pro Asp Glu Ser Glu Asp Ile Asp Val Ser Ile Tyr Phe
            740                 745                 750

Ser Thr Lys Met Asp Cys Asp Gln Val Thr Lys Ser Ile Ser Phe Glu
            755                 760                 765

Ser Ser Thr Glu Ala Gly Lys Thr Pro Ser Ile Ser Asn Asn Ser Val
        770                 775                 780

Ser Cys Lys Asp Ala Lys Gly Asp Asp Pro Lys Trp Thr Gly Gln Ile
785                 790                 795                 800

Pro Asn Ala Trp Val Trp Thr Ala Lys Leu Thr Gly Val Tyr Asn Gly
                805                 810                 815

Ile His Arg Leu Thr Val Lys Asn Ala Thr Ser Ser Asp Gly His Ser
            820                 825                 830

Ser Thr Gln Ala Thr Asp His Phe Leu Ile Arg Val Gly Gln Arg Asp
        835                 840                 845

Asn Pro Leu Val Phe Thr Ser Ala Asn Tyr Ser Thr Ser Leu Leu Asn
850                 855                 860

Gln Tyr Asp Asn Gly Thr Leu Tyr Ile Gln His Arg Ala Ala Gly Ala
865                 870                 875                 880

Asn Lys Tyr Arg Tyr Ser Thr Asn Phe Gly Ser Ser Phe Ser Asp Trp
                885                 890                 895

Lys Asp Tyr His Gly Asn Asp Thr Ile Glu Glu Leu Pro Trp Ser
            900                 905                 910

Gly Thr Asp Lys Gln Lys Trp Gln Gly Lys His Val Arg Val Glu Tyr
        915                 920                 925

Trp Asn Lys Leu Thr Gly Ser Ser Asp Tyr Ala Gln Glu Gly Asp Ser
        930                 935                 940

Gly Tyr Asp His Pro Arg Arg Phe Pro His Leu Phe Phe Asn Gly Pro
945                 950                 955                 960

Phe Asn Gln Tyr Gly Tyr Asp Ala Gly Leu Asp Asn Val Val Arg Gln
                965                 970                 975

Asp Ser Asp Gly Leu Trp Lys Phe Arg Phe Met Ala Glu Phe Pro Ala
            980                 985                 990

Gln Gly Gln Phe Asn Val Trp Gly  Met Asn Pro Asp Gly  Gln Pro Asp
```

-continued

```
           995                 1000                1005
Gln  Ser  Tyr  Val  Phe  Gly  Asp  Val  Asp  Asp  Gly  Val  Leu  Asp
     1010                1015                1020

Arg  Met  Pro  Pro  Ser  Ser  Leu  Ser  Ser  Thr  Ile  Ile  Asn  Ile  Thr
     1025                1030                1035

Asp  Ile  Pro  Pro  Ser  Pro  Tyr  Leu  Ala  Trp  Asn  Leu  Gly  Val  Asp
     1040                1045                1050

Asp  Gly  Thr  Leu  Arg  Val  His  Leu  Leu  Pro  Thr  Gly  Ser  Arg  Thr
     1055                1060                1065

Ile  Gln  Met  Val  Val  Tyr  Phe  Leu  Leu  Trp  Phe  Val  Pro  Leu  Val
     1070                1075                1080

Thr  Ala  Ile  Ala  Cys  Val  Tyr  Ala  Phe  Val  Lys  Ser  Phe  Tyr  Gln
     1085                1090                1095

Val  Lys  Phe  Asn  Gln  Val  Gly  Val  Ser  Glu  Lys  Lys  Ser  Ile  Leu
     1100                1105                1110

Pro  Leu  Ala  Phe  Arg  Arg  Lys  Leu  Ser  Arg  Asp  Gly  Ser  Gly  Gly
     1115                1120                1125

Ser  Ile  Asn  Pro  Phe  Met  Arg  Leu  Ala  Asn  Lys  Ser  Gly  Phe  Leu
     1130                1135                1140

Gln  Ser  Thr  Pro  Ala  Phe  Gly  Ala  Val  Ala  Ser  Arg  Arg  Arg  Thr
     1145                1150                1155

Thr  Leu  Ile  Ala  Thr  Met  Glu  Tyr  Asp  Ile  Glu  Asp  Trp  Ala  Ile
     1160                1165                1170

Lys  Ile  Lys  Ile  Gly  Gly  Leu  Gly  Val  Met  Ala  Gln  Leu  Met  Gly
     1175                1180                1185

Lys  His  Leu  Gly  Gln  Gln  Asp  Leu  Ile  Trp  Val  Pro  Cys  Val
     1190                1195                1200

Gly  Gly  Val  Asp  Tyr  Pro  Val  Asp  Gln  Pro  Ala  Glu  Pro  Met  Phe
     1205                1210                1215

Val  Thr  Val  Leu  Gly  Asn  Ser  Tyr  Glu  Val  Lys  Val  Gln  Tyr  His
     1220                1225                1230

Val  Leu  Asn  Asn  Ile  Lys  Tyr  Val  Leu  Leu  Asp  Ala  Pro  Val  Phe
     1235                1240                1245

Arg  Gln  Gln  Thr  Lys  Ser  Glu  Pro  Tyr  Pro  Ala  Arg  Met  Asp  Asp
     1250                1255                1260

Leu  Asp  Ser  Ala  Ile  Tyr  Tyr  Ser  Ala  Trp  Asn  Gln  Cys  Ile  Ala
     1265                1270                1275

Gln  Ala  Ile  Arg  Arg  Phe  Pro  Ile  Asp  Leu  Tyr  His  Ile  Asn  Asp
     1280                1285                1290

Tyr  His  Gly  Ser  Ile  Ala  Pro  Leu  Tyr  Leu  Leu  Pro  Gln  Thr  Ile
     1295                1300                1305

Pro  Val  Cys  Leu  Ser  Leu  His  Asn  Ala  Glu  Phe  Gln  Gly  Leu  Trp
     1310                1315                1320

Pro  Met  Arg  Thr  Gln  Lys  Glu  Arg  Asp  Glu  Val  Cys  Ser  Val  Phe
     1325                1330                1335

Asn  Leu  Asp  Leu  Asp  Thr  Ala  Lys  Arg  Tyr  Val  Gln  Phe  Gly  Glu
     1340                1345                1350

Val  Phe  Asn  Met  Leu  His  Ala  Gly  Ala  Ser  Tyr  Leu  Arg  Val  His
     1355                1360                1365

Gln  Gln  Gly  Phe  Gly  Ala  Val  Gly  Val  Ser  Arg  Lys  Tyr  Gly  Lys
     1370                1375                1380

Arg  Ser  Tyr  Ala  Arg  Tyr  Pro  Ile  Phe  Trp  Gly  Leu  Lys  Lys  Val
     1385                1390                1395
```

```
Gly Asn Leu Pro Asn Pro Asp Pro Ser Asp Thr Gly Glu Trp Asn
              1400             1405             1410

Lys Glu Leu Pro Lys Asp Ser Glu Ile Arg Val Asp Pro Asn Tyr
              1415             1420             1425

Glu Ala Ser Arg Gly Glu Leu Lys Arg Gln Ala Gln Glu Trp Ala
              1430             1435             1440

Gly Leu Asp Gln Asn Pro Asp Ala Asp Leu Leu Val Phe Val Gly
              1445             1450             1455

Arg Trp Ser Met Gln Lys Gly Val Asp Leu Ile Ala Asp Val Met
              1460             1465             1470

Pro Ala Val Leu Glu Ala Arg Pro Asn Val Gln Leu Ile Cys Val
              1475             1480             1485

Gly Pro Val Ile Asp Leu Tyr Gly Lys Phe Ala Ala Leu Lys Leu
              1490             1495             1500

Asp His Met Met Arg Leu Tyr Pro Gly Arg Val Phe Ser Lys Pro
              1505             1510             1515

Glu Phe Thr Ala Leu Pro Ala Tyr Ile Phe Ser Gly Ala Glu Phe
              1520             1525             1530

Ala Leu Ile Pro Ser Arg Asp Glu Pro Phe Gly Leu Val Ala Val
              1535             1540             1545

Glu Phe Gly Arg Lys Gly Ala Leu Gly Ile Gly Ala Arg Val Gly
              1550             1555             1560

Gly Leu Gly Gln Met Pro Gly Trp Trp Tyr Asn Ile Glu Ser Thr
              1565             1570             1575

Thr Thr Ser His Leu Leu His Gln Phe Lys Leu Ala Ile Gly Ser
              1580             1585             1590

Ala Leu Asn Ser Lys Pro Gln Val Arg Ala Lys Met Arg Ala Arg
              1595             1600             1605

Ser Ala Lys Gln Arg Phe Pro Val Ala Gln Trp Val Glu Asp Leu
              1610             1615             1620

Glu Ile Leu Gln Thr Thr Ala Met Arg Ile His Ser Lys Gly Gln
              1625             1630             1635

Ala Lys Ser Asn Gly Gly Pro Leu Ser Pro Ser Gly Tyr Asn Thr
              1640             1645             1650

Pro Ser Glu Val Ile Thr Pro Ser Gly Met Met Thr Pro Thr Ile
              1655             1660             1665

Ala Ser Thr Gly Thr Thr Thr Pro Thr Gly Met Gln Thr Pro Pro
              1670             1675             1680

Ile Ala His Ser Arg Glu Gly Ser Tyr Thr Asn Leu Ser Val Asn
              1685             1690             1695

Arg Asp Ser Ala Tyr Gly Pro Gln Gln Arg Asn Thr Ile Val Tyr
              1700             1705             1710

Ser Arg Asp Pro Ser Pro Gly Gly Asn Asp Glu Pro Arg Leu Ser
              1715             1720             1725

Leu Gly Arg Gln Leu Ser Leu Gly Phe Arg Ala Gly Pro Gly His
              1730             1735             1740

Ile Asn Leu Arg Gly Arg Leu Lys Arg Arg Ser Gln Met Thr
              1745             1750             1755

Asn Glu Glu Ser Gly Thr Ala Thr Glu Glu Ser Ser Asp Asp Asp
              1760             1765             1770

Tyr Phe Arg Gly Glu Glu Glu Val Thr Ile Thr Arg Glu Gln Ala
              1775             1780             1785
```

-continued

Asp Glu Gly Arg His Gln Arg Asn Ala Pro Arg Ser Leu Ala Ser
1790                1795                1800

Pro Pro Asn Ser Tyr Phe Glu Glu Gly Ile Thr Ser Gly Arg Pro
1805                1810                1815

Pro Trp Ala Gln Pro Gly Asn Arg Leu Ser Ser Ala Ser Val Leu
1820                1825                1830

Ser Val Asp Ser Val Val Gly Glu Lys Lys Asp Tyr Lys Leu Gln
1835                1840                1845

Lys Val Asp Pro Phe Phe Thr Asp Gly Thr Gly Glu Tyr Tyr Arg
1850                1855                1860

Met Phe Asp Gln Arg Leu Glu Lys Leu Asn Gly Ser Asn Ser Glu
1865                1870                1875

Ser Gln Leu Cys Ile Glu Glu Tyr Leu Met Lys Ser Glu Lys Lys
1880                1885                1890

Trp Phe Asp Lys Phe Arg Asp Ala Arg Leu Gly Arg Asn Gln Ser
1895                1900                1905

Pro Ala Ser Ser Ile Phe Gln Thr Lys Gly Glu Asn Asn Thr Pro
1910                1915                1920

Met Ser Ser Ile Ser His Glu Asp Leu Gly Ser Asn Glu Ser Gly
1925                1930                1935

Ser Asp Pro Arg Ala Glu Lys Asp Glu Phe Leu Leu Gly Arg Asp
1940                1945                1950

Tyr Val Pro Pro Ser Gly Leu Arg Lys Trp Met Gln Ile Arg Ile
1955                1960                1965

Phe Gly Trp Pro Val Tyr Ser Phe Phe Leu Gly Leu Gly Gln Ile
1970                1975                1980

Ile Ala Ala Asn Ser Tyr Gln Ile Thr Leu Leu Ala Gly Glu Asn
1985                1990                1995

Gly Gln Thr Ala Glu Lys Leu Tyr Gly Ile Ala Thr Val Tyr Leu
2000                2005                2010

Val Thr Ser Ile Ile Trp Trp Phe Phe Phe Arg Phe Phe Lys Ser
2015                2020                2025

Val Phe Val Leu Ser Ile Pro Trp Phe Leu Tyr Gly Ala Ser Phe
2030                2035                2040

Val Ile Ile Gly Leu Ala His Phe Glu Ser Asn Gly Ser Ala Arg
2045                2050                2055

Gly Trp Ile Gln Asn Val Gly Ser Gly Val Tyr Ala Ala Ala Ser
2060                2065                2070

Ser Ser Gly Ser Leu Phe Phe Ala Leu Asn Phe Gly Asp Glu Ser
2075                2080                2085

Gly Val Gln Val Lys Asp Trp Val Phe Arg Ala Cys Leu Ile Gln
2090                2095                2100

Gly Thr Gln Gln Ala Tyr Val Ile Gly Leu Trp Tyr Trp Gly Thr
2105                2110                2115

Thr Ile Ser Ser Ala Val Ala Asn Gly Val Thr Asn Val Asn Gly
2120                2125                2130

Gly Ile Val Asn Ser Trp Lys Met Thr Ala Ile Cys Met Pro Ile
2135                2140                2145

Ala Ala Phe Leu Trp Ala Ile Gly Leu Ile Ile Phe Phe Gly Leu
2150                2155                2160

Pro Asn Tyr Tyr Arg Gln Ser Pro Gly Lys Val Pro Ser Phe Tyr
2165                2170                2175

Lys Ser Val Phe Arg Arg Lys Ile Val Leu Trp Asn Phe Val Val

```
                       2180                2185                2190

Val Ile Leu Gln Asn Phe Phe Leu Ser Ala Pro Tyr Gly Arg Asn
               2195                2200                2205

Trp Ala Phe Leu Trp Ser Ser Asn His Ala Glu Ala Trp Gln Val
               2210                2215                2220

Gly Ile Leu Val Val Val Phe Phe Gly Val Ile Trp Val Ala Val
               2225                2230                2235

Leu Thr Leu Phe Gly Tyr Leu Ser Lys Arg His Ser Trp Ile Leu
               2240                2245                2250

Pro Val Phe Ala Cys Gly Leu Gly Ala Pro Arg Trp Ala Gln Ile
               2255                2260                2265

Trp Trp Gly Val Ser Gly Met Gly Leu Phe Leu Pro Trp Ala Gly
               2270                2275                2280

Ser Ser Val Ser Gly Ala Leu Ala Ser Arg Ser Leu Trp Leu Trp
               2285                2290                2295

Leu Gly Ile Leu Asp Ala Leu Gln Gly Leu Gly Phe Gly Met Ile
               2300                2305                2310

Leu Leu Gln Thr Leu Thr Arg Val His Ile Ala Phe Thr Leu Leu
               2315                2320                2325

Ala Ser Gln Val Leu Gly Ser Ile Ala Thr Ile Val Ala Arg Ala
               2330                2335                2340

Cys Ala Pro Asn Asn Ile Gly Pro Gly Pro Ile Ser Pro Asp Val
               2345                2350                2355

Thr Ala Gly Gly Ser Ser Val Ala Asn Ala Trp Phe Trp Ile Ala
               2360                2365                2370

Leu Phe Phe Gln Leu Leu Ile Cys Ala Gly Phe Leu Leu Phe Phe
               2375                2380                2385

Arg Lys Glu Gln Leu Thr Lys Pro
               2390                2395

<210> SEQ ID NO 28
<211> LENGTH: 7488
<212> TYPE: DNA
<213> ORGANISM: Aspergillus oryzae

<400> SEQUENCE: 28
atgaagtggg gattcactgg cccgttgctt gcgttgctcg cagcaacagc agcaggctgg      60
ccctatgatg agtccctagt cgattataac ttgaatgtga acaaggatac taccaatccg     120
gctgaatata ctcacgcaga atggaagggc catgagtata tccctctcc aaaaagctgg      180 cgattcccct tctataccct gttcattgac cggtttgtca atggcgatcc tactaacgat     240
aacatcaacg ggtcactctt tgaacatgat cttaattcaa accaaatgcg tcacggtggt     300
gatgcagctg gcttggtcga tacactagac tacctacaag gtatgggcat aaaggttggt     360
agcaatgatc tccgtgttgt ttcttgctat tggtgtttac cgcatatggc tgactgacct     420
ctacagggga tctatttggc tggtactatc ttgatgaatc aaccatgggg ctcagacggt     480
tactcgattt tggatactac cctgcttgat cagcattatg gtacaattca aacctggaga     540
gacgcgatca ccgagattca taagcggggc atgtatgtcc tctttgacaa tactatcgca     600
acgtaagatg ctgcccctca cctaagtcgt tatatcccag agctgacatg aaaccagcat     660
gggcgatttg attggatttg aaggttattt gaatactacc acgcctttct cagtcaagga     720
gcacaaagca ttgtggaaat ctgaccgtca gtatgtcgac ttccgttttg acaatgagta     780
caacaacact tgcgaatacc ctcgattctg gaacgagact ggctatccgg tcgataagga     840
```

```
tgtcacagat gagctggttg gatgctataa cagtgatttc gaccagtacg gtgacagaga    900
agctttcggt gtctacccag actgggagcg ccagttggcc aaattcgctt cagttcagga    960
tcgtctacgt gaatggcacc ctagcgttaa agagagactt attcggcact cgtgtatgat   1020
tataaaggca cttgacattg atggcttccg ctacgataaa gcgacgcagg ccacagtgga   1080
tgctcttgga gacatgtccc atgcttatag agagtgtgct cgcagtgttg caaggataa    1140
cttcttcctt cctggagaaa ttactggtgg aaataacttt ggttctattt acctcggacg   1200
tggaagacag cccaaccaat acccagactc ctccttggct tcgatgaacc tgacgaacac   1260
ctccgatcat cagtatttct tacgtgatga cggtctacaa gcgctagatt cagcagcttt   1320
ccattattcg gtgtaccgta ccctcactcg attcctaggt atggatggca atctggctgc   1380
gggctatgac acaccgttgg actggacgga ctcctggaat attatggtat tgagcaacga   1440
tatgatcaat gctaacactg gcaaatttga cccccggcat atgtatggta ctacaaacca   1500
ggatgttttc cgttggcctg ccatcgagct cggagtcgag agacagcttt tgggtcactt   1560
catcacaacc ttgcatctcc cgggcatccc aattttgctg tggggagaag aacaagcctt   1620
ctacattcta gactctactg cggataacta tatctatggc cgccaagcaa tgtctccctc   1680
cactgcgtgg aaaacacacg gatgttattc ccttggttcg tcccaatact acaactggcc   1740
tgtcagtgca ggtagggaag gatgtcatga tgaagctgtc gcttatgatc atcgagatcc   1800
ctctcatcca gtccacaata tcatcaaaca tatgttccag atgcgacagg acttccctgt   1860
actaaatgat ggatactcag ttgtcaagtt gtcaaaacag actcgtgaga ttcagtatcc   1920
tggttcgaat ggcacggcaa cggaagtcgg cgtctggtca gtcctgcgtg atcttgtctc   1980
caacattcaa gactttggtg acagcggcaa caacgaacct gtctggctgg tctatcaaaa   2040
tgacaacaag accgtggaat atagctttga ttgtgggagt aacgattcgg ccttgatttc   2100
cccatttact acgggaacta ctgttgttaa tctcttctac ccacacgatg aacacgagct   2160
taaagatggc cccaaatcac ttcatctgaa cggcaccaat gcaacaaacg gttgtctgga   2220
tactttgaag ttgaagccct tcgagttcag ggcttacgtt ccaaaggcta actttgttaa   2280
gcctcgtccc atgatcaccc agttcgagcc tggtcacgat gtgccgcagc tgtctaaagt   2340
cggacctgac gaatcagaag atattgacgt gagcatttac ttttccacca agatggattg   2400
tgatcaggtt acgaaatcca tttcattcga atccagtacc gaagctggca agactccctc   2460
tatcagtaat aacagtgtca gctgcaaaga tgccaagggt gatgatccga agtggactgg   2520
tcaaattccc aacgcctggg tctggacagc gaagttgact ggcgtttaca acggtatcca   2580
tcgcttgacc gtcaaaaatg ccactagctc ggatgggcat agttctaccc aggcaactga   2640
tcacttcttg atccgagtgg gccaaaggga taatccgttg gtgttcacat ctgcgaacta   2700
ctcgacctcc ttgttaaacc agtatgacaa tggcacgctc tacatccaac atcgtgcagc   2760
aggtgcaaac aaataccgct attcaacaaa ctttggttcc tcattctctg actgaaagaa   2820
ctaccacgga gggaacgata ctattgaaga actgccctgg agtggaacgg acaagcaaaa   2880
gtggcaaggg aagcacgtgc gagtcgaata ctggaataag ttaaccggca gcagtgacta   2940
cgctcaggaa ggcgactctg gatatgacca tccaagacgc tttccccatc ttttcttcaa   3000
cgggccattc aaccaatatg gatatgatgc gggcttggac aacgttgtga ggcaagacag   3060
tgatggtctt tggaagttca gattcatggc tgagtttcca gcacaaggac agttcaatgt   3120
ttggggaatg aatccagatg gtcaaccaga ccagagctac gtgttcggtg atgttgatga   3180
```

```
tgacggagtt ttggatcgca tgcctccttc ttcgcttagt tccacgataa taaacatcac    3240
ggatatccct ccatctccat acttggcgtg aatcttggt gttgacgatg aactctgcg      3300 tgttcatctt ctgccaacgg gttcaaggac catccaaatg gttgtgtact tcctcctctg    3360
gtttgttccc cttgtcacag ccatcgcttg tgtctatgcc ttcgtgaaat ccttctacca    3420
agtcaagttc aaccaagtgg gggtcagcga aaagaaatca attcttccat ggcattccg     3480 aaggaaactg agccgtgatg gaagcggggg atcaatcaat cctttcatgc gccttgccaa    3540
taagtcggga ttcttgcaaa gcacacctgc ttttggagca gtcgcttcac gaagacggac    3600
gaccttgatt gccaccatgg aatatgatat tgaggactgg gccatcaaga ttaaaatcgg    3660
tggtctaggt gttatggctc agttgatggg caaacacctt gggcagcagg atctaatttg    3720
ggttgttcca tgcgtgggtg gagttgacta cccggtagat cagccagctg agcctatgtt    3780
tgtgacagtg ctcggaaatt cctacgaagt caaggtgcag tatcacgtcc tgaataatat    3840
taaatatgtc cttttagatg ctcctgtttt tcgtcaacag accaaatctg agccttatcc    3900
cgcccgaatg gacgatttgg acagcgcaat ctactattcc gcttggaacc agtgcattgc    3960
acaagcaatc agacgtttcc caattgatct ttatcatatt aacgactacc atggatccat    4020
tgcccctctt tatcttctac ctcaaaccat ccctgtatgt ctgtcgctcc acaatgccga    4080
gttccaagga ctgtggccta tgcgcaccca gaaggagagg gatgaagtct gttctgtttt    4140
caaccttgat cttgacactg caaagcgcta cgtccaattt ggcgaagttt ttaacatgct    4200
tcatgctgga gcaagctacc tacgcgtgca tcaacaaggg tttggtgcag tgggcgtttc    4260
tcgaaagtac ggtaaacgtt cttatgcccg gtacccaatc ttttgggtc tgaagaaggt    4320 tggaaatcta ccgaacccgg acccttcaga cactggcgaa tggaacaagg agttaccaaa    4380
ggacagcgag attcggggttg acccgaacta cgaggctagc agaggagagc ttaagcggca    4440
ggcgcaggaa tgggcaggct tggatcaaaa ccctgatgcc gacctgttgg tgtttgttgg    4500
aagatggtct atgcagaagg gcgtggacct tattgctgat gtgatgcctg ccgttctgga    4560
agcacgtccc aatgttcaac tcatctgtgt tggtccagtc attgatcttt atggtaaatt    4620
tgctgctctt aagctggatc atatgatgag gttatatcct gggcgtgtct tctcaaagcc    4680
tgagtttact gcactcccag catatatctt ctctggcgcc gaattcgccc tgattccatc    4740
tcgtgatgaa cctttggtc ttgttgctgt cgaatttggt cgaaagggcg ctcttggtat    4800
tggtgctcgt gttggtggtc tcggccagat gcctggttgg tggtataata ttgagtctac    4860
aacaacttcc catctcttgc atcaattcaa gcttgcgatt ggaagcgcgc ttaactcgaa    4920
gccccaagtt cgtgcaaaga tgcgtgcacg ctccgcaaag caacgctttc ctgttgctca    4980
gtgggtggaa gatttggaaa ttctgcagac cactgctatg cggattcaca gcaagggaca    5040
ggcaaaatcg aacggtggac ctctctcgcc ttctggttac aatacaccaa gtgaagtaat    5100
aacaccaagt ggaatgatga cacctacgat tgcatcgact ggtaccacga ccccaacggg    5160
aatgcagacg cctccaatcg cacactcacg ggaaggcagt tacacgaatc tcagcgtcaa    5220
tcgcgacagt gcatacgggc cccaacagcg caacacaatt gtgtacagcc gtgacccaag    5280
ccctggaggt aatgacgaac ctaggttaag ccttggtcgg caactgtcac ttggattcag    5340
ggctggacca ggacatatta atctccgtgg tcgtcggctt aaaagaagaa gccagatgac    5400
caacgaggag agtggtacag cgaccgaaga aagcagtgat gacgattatt ccgcggaga    5460 ggaagaagtt acgattacga gggagcaagc agatgaagga cgtcatcaac gcaatgctcc    5520
gaggtcgctt gcatctcctc ccaactctta ctttgaagaa ggcataacat ccggaaggcc    5580
```

```
accttgggct caacctggga atcgactcag tagtgcatcc gttctttctg ttgattctgt    5640
cgtcggcgaa aagaaagact ataagctgca gaaagttgat ccattcttca cagacggtac    5700
tggcgaatac tatcgaatgt ttgatcagag actcgaaaag ctcaacggat ctaactctga    5760
atcccagctt tgtatagagg agtatctgat gaagagcgaa aagaagtggt ttgacaagtt    5820
cagagacgca agattggggc gcaaccaatc tcccgcttct tcgattttcc aaaccaaggg    5880
cgaaaacaac acacctatga gctcaatctc ccacgaggat ctgggttcaa cgaaagtgg    5940 cagcgatcca cgcgcagaaa aggatgagtt ccttctggga cgagactatg ttccccctc    6000 gggcttaagg aaatggatgc aaattcgaat cttttggctgg cctgtgtatt cgttttcct    6060 aggtctcggt cagatcattg cggccaactc ataccaaatt accttgcttg ccggtgaaaa    6120
cggccagaca gctgagaagc tctatggtat tgcgacagta taccttgtca cttcaatcat    6180
ctggtggttt ttcttccgct tcttcaaatc ggtgtttgtc cttccatac cttggttctt     6240 atacggcgca tcgtttgtca tcattggatt agcacacttt gagtcaaatg gctccgctcg    6300
tggatggatc cagaatgtgg gaagcggtgt ttacgctgct gcttcttcaa gcggatcact    6360
gttcttcgct ctcaattttg gcgatgaaag cggtgttcag gttaaagact gggttttccg    6420
ggcatgcctc atccaaggaa cccagcaagc atatgttatt ggactgtggt actggggaac    6480
gacaatctct agcgctgtcg ccaatggagt taccaacgtc aacggcggca ttgtcaactc    6540
ctggaaaatg acgtatgttt cacctttatc actatgatta caattgctaa cggcctcttc    6600
tagcgcaatc tgcatgccaa tcgctgcatt cctctgggcc attggtctga taatcttctt    6660
cggcctgccc aattactacc gccagtcacc tggaaaagtt ccatcattct acaagtctgt    6720
cttccggcgc aagatcgtcc tgtggaactt cgtggtagtc attttgcaaa atttcttcct    6780
cagcgcacct tatggacgaa actgggcctg taagtacatc agacctatac tctccaagaa    6840
gccactaact tatcgtgcct catacagtcc tttggagctc aaaccatgcc gaagcctggc    6900
aagtcggcat cctcgtcgtc gtcttcttcg gtgtcatctg ggtagcagtg ttaaccctat    6960
ttggatatct ctcgaagcgc catagctgga ttctacctgt atttgcatgc ggtttgggag    7020
ctccacgttg ggcccagata tggtggggtg tctccggaat gggtctcttc cttccctggg    7080
ctggcagttc tgttagcgga gcactcgcat cacgaagtct atggctctgg ctcggtatcc    7140
ttgatgcctt acagggtctc ggcttcggca tgattcttct ccagaccctc acacgagtac    7200
atatagcctt caccctgctt gcatctcaag tgctgggatc catcgcgaca atcgtcgcca    7260
gagcatgtgc tccaaataac atcggtcctg gaccaatctc gccggatgtg actgccggtg    7320
gcagttccgt tgcaaacgct tggttctgga tcgccttatt cttccagctc ttgatctggt    7380
aagtcatcga tccccctaca atccatttca caggcagcaa aatgctaaca aagccccagc    7440
gccggattcc ttctgttctt ccggaaagaa caactcacca agccctaa              7488
```

<210> SEQ ID NO 29
<211> LENGTH: 2430
<212> TYPE: PRT
<213> ORGANISM: Aspergillus oryzae

<400> SEQUENCE: 29

Met Lys Trp Ala Phe Ser Ser Ala Val Leu Ala Leu Phe Ala Thr Thr
1               5                   10                  15

Val Lys Ala Trp Pro Tyr Glu Glu Ser Leu Ser Ala Tyr Asn Leu Asn
            20                  25                  30

```
Glu Asn Lys Ser Ala Thr Asn Pro Ala Gln Tyr Trp Gly Glu Trp Pro
             35                  40                  45

Asp His Lys Gly Lys Tyr Phe Pro Ser Pro Asp Asn Trp Arg Phe Pro
 50                  55                  60

Val Tyr Thr Leu Phe Met Asp Arg Phe Val Asn Gly Asp Pro Thr Asn
 65                  70                  75                  80

Asp Asn Ile Asn Gly Thr Leu Phe Glu His Asp Ile Ser Ser Thr Gln
                 85                  90                  95

Met Arg His Gly Gly Asp Val Ala Gly Leu Val Asp Thr Leu Asp Tyr
                100                 105                 110

Leu Gln Gly Met Gly Ile Lys Ala Ile Tyr Leu Ala Gly Thr Ile Leu
            115                 120                 125

Met Asn Gln Pro Trp Gly Ser Asp Gly Tyr Ser Ala Leu Asp Thr Thr
130                 135                 140

Leu Leu Asp Gln His Phe Gly Asp Ile Ala Thr Trp Arg Asn Ala Ile
145                 150                 155                 160

Asp Glu Ile His Lys Arg Gly Met Tyr Val Ile Phe Asp Asn Thr Ile
                165                 170                 175

Ala Thr Met Gly Asp Leu Ile Gly Phe Glu Gly His Leu Asn Asp Thr
            180                 185                 190

Thr Pro Phe Ser Val Lys Glu His Lys Ala Leu Trp Lys Ser Asn Arg
        195                 200                 205

Arg Tyr Val Asp Phe Asp Ile Gly Asn Asp Tyr Asn Gln Thr Cys Asp
    210                 215                 220

Tyr Pro Arg Phe Trp Tyr Glu Asp Gly Tyr Pro Val Gln Gln Ser Met
225                 230                 235                 240

Thr Glu Gly Leu Val Gly Cys Tyr Asp Ser Asp Phe Asp Gln Tyr Gly
                245                 250                 255

Asp Ile Glu Ala Phe Gly Val Phe Pro Asp Trp Gln Arg Gln Leu Ala
            260                 265                 270

Lys Phe Ala Ser Val Gln Asp Arg Leu Arg Glu Trp His Pro Ser Val
        275                 280                 285

Arg Glu Arg Leu Ile Arg His Ser Cys Met Ile Ile Tyr Gln Leu Asp
    290                 295                 300

Ile Asp Gly Phe Arg Tyr Asp Lys Ala Thr Gln Ser Thr Val Asp Ala
305                 310                 315                 320

Leu Gly Asp Met Ser Met Ala Tyr Arg Glu Cys Ala Arg Ala Val Gly
                325                 330                 335

Lys Glu Asn Phe Phe Ile Ser Gly Glu Ile Thr Gly Gly Asn Thr Phe
            340                 345                 350

Gly Ser Ile Tyr Leu Gly Arg Gly Arg Gln Pro Asn Gln Tyr Pro Glu
        355                 360                 365

Thr Ala Glu Lys Ala Met Lys Met Thr Asn Glu Ser Glu Ser Gln Tyr
    370                 375                 380

Phe Leu Arg Glu Ala Gly His Glu Ala Ile Asp Gly Ala Ala Phe His
385                 390                 395                 400

Tyr Ser Thr Tyr Arg Ala Leu Thr Arg Phe Leu Gly Met Asp Gly Asn
                405                 410                 415

Leu Ala Ala Gly Tyr Asp Val Pro Val Asp Trp Val Asp Ala Trp Asn
            420                 425                 430

Leu Met Leu Gln Ser Asn Asp Phe Ile Asn Pro Asn Thr Gly Lys Phe
        435                 440                 445

Asp Pro Arg His Met Phe Gly Ala Thr Asn Gln Asp Val Phe Arg Trp
```

```
              450                 455                 460
Pro Thr Val Glu Lys Gly Val Glu Arg Gln Leu Leu Gly Leu Tyr Ile
465                 470                 475                 480

Thr Thr Leu Leu Leu Pro Gly Ile Pro Leu Leu Trp Gly Glu Glu
                485                 490                 495

Gln Ala Phe Tyr Ile Leu Asp Ala Thr Ala Ser Asn Tyr Ile Tyr Gly
                500                 505                 510

Arg Gln Ala Met Ser Pro Ala Thr Ala Trp Arg Asp His Gly Cys Phe
                515                 520                 525

Ser Leu Asp Ser Ser Gln Tyr Tyr Gln Trp Pro Ile Gln Ala Gly Arg
            530                 535                 540

Glu Gly Cys His Asp Pro Thr Ala Ala Tyr Asp His Arg Asp Pro Ala
545                 550                 555                 560

His Pro Val Arg Asn Ile Ile Lys His Met Tyr Gln Leu Arg Glu Asp
                565                 570                 575

Phe Pro Val Leu Asn Asp Gly Tyr Ser Val Gln Lys Leu Ser Asn Leu
                580                 585                 590

Thr Glu Glu Val Phe Tyr Pro Gly Ser Asn Gly Thr Ala Thr Glu Thr
            595                 600                 605

Gly Leu Trp Ser Ile Leu Arg Asp Val Asn Ala Asp Val Gln Asp Leu
            610                 615                 620

Gly Ser Asp Ala Lys Asn Gln Pro Val Trp Leu Val Tyr His Asn Thr
625                 630                 635                 640

Asn Arg Thr Ile Asp Phe Lys Phe Asn Cys Lys Asp Asn Glu Thr Ala
                645                 650                 655

Leu Ile Ser Pro Phe Ala Thr Gly Thr Lys Val Arg Asn Leu Phe Tyr
                660                 665                 670

Pro Tyr Asp Glu His Thr Leu Ile Asp Gly Pro Val Lys Leu Gly Leu
            675                 680                 685

Asn Gly Ser Thr Glu Leu Asn Gly Cys Leu Ala Asn Met Thr Leu Asp
            690                 695                 700

Ala Tyr Glu Phe Arg Ala Tyr Val Pro Ser Ala Arg Phe Thr Lys Pro
705                 710                 715                 720

Arg Pro Met Ile Thr Gln Phe Thr Pro Gly His Asp Val Pro Val Arg
                725                 730                 735

Ser Thr Val Ala Pro Asn Leu Asp Glu Ser Val Lys Ile Glu Leu Tyr
                740                 745                 750

Phe Ser Glu Glu Met Asp Cys Asp Ser Val Thr Lys Ala Ile Ser Ile
            755                 760                 765

Ser Ser Ser Thr Glu Ser Lys Lys Val Pro Thr Leu Asp Glu Lys Thr
            770                 775                 780

Val Asp Cys Lys Gly Ile Pro Ala Ser Asn Thr Ser Trp Thr Gly Gln
785                 790                 795                 800

Leu Pro Ser Val Phe Met Trp Ala Ala Asn Leu Thr Gly Val Tyr Asn
                805                 810                 815

Gly Ile His Arg Val Thr Val Lys Asn Ala Ser Ser Thr Asn Gly Asn
                820                 825                 830

Ala Thr Thr Asn Ala Val Asp His Phe Leu Phe Arg Ile Gly Gln Ile
            835                 840                 845

Asp Asn Pro Met Val Phe Thr Ser Ala Asn Tyr Ser Thr Ser Leu Leu
            850                 855                 860

His Glu Glu Ser Asn Gly Thr Leu Phe Ile Gln His His Ala Ala Gly
865                 870                 875                 880
```

-continued

```
Ala Asp Lys Trp Arg Tyr Ser Thr Asn Trp Gly Thr Thr Phe Ser Glu
            885                 890                 895

Trp Lys Asp Tyr Thr Gly Gly Asn Asp Thr Ile Thr Glu Leu Glu Trp
            900                 905                 910

Ser Gly Thr Lys Lys Gln Arg Trp Lys Gly His His Val Arg Val Glu
            915                 920                 925

Tyr Trp Ser Lys Trp Thr Gly Ser Ser Asp Tyr Val Gln Glu Gly Asp
            930                 935                 940

Ala Gly Val His Ser Asn Val Pro Arg Arg Phe Pro His Ile Phe Phe
945                 950                 955                 960

Asn Gly Pro Tyr Asn Gln Tyr Gly Tyr Asp Gly Gly Leu Asp Asn Val
            965                 970                 975

Val Arg Gln Asp Ser Lys Asp Gly Leu Trp Lys Tyr His Phe Thr Ala
            980                 985                 990

Glu Trp Pro Ala Gln Ala Gln Leu Asn Ile Trp Gly Met Asn Pro Asp
            995                 1000                1005

Gly Lys Pro Asp Gln Ser Trp Val Leu Gly Asp Ala Asp Asn Asp
        1010                1015                1020

Ser Val Leu Asp Arg Met Pro Pro Ser Ser Leu Ser Ala Thr Leu
        1025                1030                1035

Ile Asn Ile Thr Glu His Pro Pro Lys Pro Tyr Leu Ala Trp Asn
        1040                1045                1050

Ile Tyr Ile Asn Asp Ala Thr Met Lys Phe Gln Leu Phe Pro Val
        1055                1060                1065

Gly His Gln Asn Thr Gln Ile Ala Met Phe Val Leu Phe Trp Ile
        1070                1075                1080

Ile Pro Val Ile Thr Gly Ala Ala Cys Val Tyr Ile Phe Met Lys
        1085                1090                1095

Ser Phe Tyr Lys Val Lys Phe Asn Gln Ile Gly Val Ser Glu Lys
        1100                1105                1110

Ala Thr Leu Ile Pro Leu Ala Leu Arg Arg Lys Phe Lys Arg Asn
        1115                1120                1125

Arg Gly Gly Asp Glu Glu Arg Met Asn Pro Leu Met Arg Leu Ala
        1130                1135                1140

Asn Lys Ser Gly Phe Leu Gln Thr Asn Thr Ala Ile Gly Gly Ala
        1145                1150                1155

Ala Ser Gly Lys Arg Arg Met Val Leu Ile Ala Thr Met Glu Tyr
        1160                1165                1170

Asp Ile Glu Asp Trp Gln Ile Lys Ile Lys Ile Gly Gly Leu Gly
        1175                1180                1185

Val Met Ala Gln Leu Met Gly Lys Thr Leu Gly His Gln Asp Leu
        1190                1195                1200

Ile Trp Val Val Pro Cys Val Gly Gly Val Glu Tyr Pro Val Asp
        1205                1210                1215

Lys Pro Ala Glu Pro Met Asn Val Thr Ile Leu Gly Asn Ser Tyr
        1220                1225                1230

Glu Val Gln Val Gln Tyr His Val Leu Asn Asn Ile Thr Tyr Val
        1235                1240                1245

Leu Leu Asp Ala Pro Val Phe Arg Gln Gln Ser Lys Ser Glu Pro
        1250                1255                1260

Tyr Pro Ala Arg Met Asp Asp Leu Asn Ser Ala Ile Tyr Tyr Ser
        1265                1270                1275
```

```
Ala Trp Asn Gln Cys Ile Ala Glu Ala Cys Lys Arg Phe Pro Ile
    1280              1285              1290

Asp Leu Tyr His Ile Asn Asp Tyr His Gly Ser Leu Ala Pro Leu
    1295              1300              1305

Tyr Leu Leu Pro Asp Thr Val Pro Ala Cys Leu Ser Leu His Asn
    1310              1315              1320

Ala Glu Phe Gln Gly Leu Trp Pro Met Arg Thr Gln Lys Glu Lys
    1325              1330              1335

Glu Glu Val Cys Ser Val Phe Asn Leu Asp Ile Asp Ile Val Arg
    1340              1345              1350

Arg Tyr Val Gln Phe Gly Glu Val Phe Asn Leu Leu His Ser Gly
    1355              1360              1365

Ala Ser Tyr Leu Arg Val His Gln Gln Gly Phe Gly Ala Val Gly
    1370              1375              1380

Val Ser Lys Lys Tyr Gly Lys Arg Ser Tyr Ala Arg Tyr Pro Ile
    1385              1390              1395

Phe Trp Gly Leu Arg Lys Val Gly Asn Leu Pro Asn Pro Asp Pro
    1400              1405              1410

Ser Asp Val Gly Glu Trp Ser Lys Glu Lys Ala Ile Gly Asn Ala
    1415              1420              1425

Asp Glu Val His Val Asp Pro Asp Tyr Glu Ala Gly Arg Ala Asp
    1430              1435              1440

Leu Lys Arg Gln Ala Gln Glu Trp Ala Gly Leu Asp Val Asn Pro
    1445              1450              1455

Asp Ala Asp Leu Met Val Phe Val Gly Arg Trp Ser Met Gln Lys
    1460              1465              1470

Gly Val Asp Leu Ile Ala Asp Val Met Pro Ala Val Leu Glu Ala
    1475              1480              1485

Arg Pro Asn Val Gln Val Ile Cys Val Gly Pro Val Ile Asp Leu
    1490              1495              1500

Tyr Gly Lys Phe Ala Ala Leu Lys Leu Asp His Met Met Lys Val
    1505              1510              1515

Tyr Pro Gly Arg Val Phe Ser Arg Pro Glu Phe Thr Ala Leu Pro
    1520              1525              1530

Pro Tyr Ile Phe Ser Gly Ala Glu Phe Ala Leu Ile Pro Ser Arg
    1535              1540              1545

Asp Glu Pro Phe Gly Leu Val Ala Val Glu Phe Gly Arg Lys Gly
    1550              1555              1560

Ala Leu Gly Ile Gly Ala Arg Val Gly Gly Leu Gly Gln Met Pro
    1565              1570              1575

Gly Trp Trp Tyr Asn Val Glu Ser Thr Ala Thr Ser His Leu Leu
    1580              1585              1590

Tyr Gln Phe Lys Leu Ala Ile Asp Ala Ala Leu Asn Ser Lys Gln
    1595              1600              1605

Glu Thr Arg Ala Met Met Arg Ala Arg Ser Ala Lys Gln Arg Phe
    1610              1615              1620

Pro Val Ala Gln Trp Val Glu Asp Leu Glu Ile Leu Gln Thr Thr
    1625              1630              1635

Ala Ile Gln Val His Asn Lys Glu Leu Val Lys His Asn Gly Arg
    1640              1645              1650

Pro Phe Thr Pro Thr Gly Thr Thr Pro Ser Gly Leu Met Thr
    1655              1660              1665

Gln Pro Ala Ser Pro Leu Gly Thr Pro Gly Met Gln Thr Pro Leu
```

```
            1670                1675                1680

Ala His Ser Arg Glu Ser Ser Tyr Ser Asn Leu Asn Arg Leu Ser
        1685                1690                1695

Glu Tyr Val Thr Gln Pro Lys Thr Ser Tyr Ser Arg Asp Pro Ser
    1700                1705                1710

Pro Ser Gly Thr Glu Lys Pro Lys Ser Gly Leu Gln Arg Gln Leu
1715                1720                1725

Ser Leu Gly Val Arg Ser Gly Pro Gly His Gln Ser Arg Arg Gly
    1730                1735                1740

Arg Ala Arg Gln Arg Asp Ser Ile Pro Glu His Glu Asp Thr Gln
1745                1750                1755

Glu Ala His Gly Gly Ala Ile Thr Asp Val Glu Glu Glu Ser Ser
    1760                1765                1770

Asp Asp Asp Ile Val Asn His Tyr Ala Asp Glu Tyr Thr Leu
1775                1780                1785

Thr Pro Ala Gln Val Glu Glu Gly Arg Arg Leu Gln Ala Ala Gln
    1790                1795                1800

Gln Gln Ala Gly Val Arg Met Pro Leu Ser Pro Gly Gly Arg Arg
1805                1810                1815

Tyr Ser Gln Asp Ser Leu His Pro Arg Asn Val Gln Pro Pro Ser
    1820                1825                1830

Ser Pro Gly Thr Pro Pro Ala Ala Ser Gln Ser Leu Leu Pro Pro
1835                1840                1845

Pro Arg Leu Leu Asp Pro Gly Ser Arg Leu Ser Ser Ala Ser Val
1850                1855                1860

Leu Ser Leu Asp Ser Val Val Gly Gly Lys Lys Asp Phe Lys Leu
1865                1870                1875

Gln Lys Val Asp Pro Phe Phe Thr Asp Ser Thr Gly Glu Tyr Tyr
1880                1885                1890

Lys Ile Phe Asp Lys Lys Leu Asp Glu Leu Asn Gly Ser Asn Ser
1895                1900                1905

Glu Ser Gln Leu Cys Ile Glu Glu Tyr Leu Ile Lys Ser Glu Lys
1910                1915                1920

Glu Trp Phe Asp Lys Phe Arg Asp Ala Arg Leu Gly Arg Thr Lys
1925                1930                1935

Ser Pro Thr Pro Ser Val Tyr Arg Asp Lys His Gly Ala Ser Pro
1940                1945                1950

Ile Gly Ser Phe Tyr Asp Asp Asn Gly Ser Arg Met Ser Gly Ser
1955                1960                1965

Asp Gly Pro His Ser Asn Asp Ser Glu Asp Asp Glu Phe Leu Leu
1970                1975                1980

Gly Lys Asp Tyr Val Pro Pro Thr Gly Leu Lys Lys Trp Met Gln
1985                1990                1995

Ile Arg Ile Gly Asp Trp Pro Ile Tyr Ser Leu Phe Leu Ala Leu
2000                2005                2010

Gly Gln Ile Ile Ala Ala Asn Ser Tyr Gln Ile Thr Leu Leu Thr
2015                2020                2025

Gly Glu Val Gly Gln Thr Ala Glu Lys Leu Tyr Gly Ile Ala Thr
2030                2035                2040

Thr Tyr Leu Ile Thr Ser Ile Leu Trp Trp Leu Val Phe Arg Tyr
2045                2050                2055

Phe Lys Ser Val Val Cys Leu Ser Ala Pro Trp Phe Leu Tyr Gly
2060                2065                2070
```

Ile Ala Phe Ile Phe Ile Gly Ser Ala His Phe Glu Ser Asn Ser
2075                2080                    2085

Phe Thr Arg Gly Trp Ile Gln Asn Val Gly Ser Gly Phe Tyr Ala
2090                2095                    2100

Ala Ala Ser Ser Ser Gly Ser Phe Phe Phe Ala Leu Asn Phe Gly
2105                2110                    2115

Asp Glu Gly Gly Ala Pro Val Glu Thr Trp Ile Phe Arg Ala Cys
2120                2125                    2130

Leu Ile Gln Gly Ile Gln Ser Ala Tyr Val Ile Ala Leu Trp Tyr
2135                2140                    2145

Trp Gly Ser Thr Leu Ser Gln Ala Gln Ser Glu Gly Leu Leu Thr
2150                2155                    2160

Pro Thr Asn Asn Ile Ser Asn Ser Trp Lys Ile Ser Ala Ile Cys
2165                2170                    2175

Tyr Pro Ile Ala Ala Ala Leu Phe Gly Ile Gly Leu Leu Leu Thr
2180                2185                    2190

Phe Gly Leu Pro Asn Tyr Tyr Arg Gln Thr Pro Gly Lys Val Ala
2195                2200                    2205

Ser Phe Tyr Lys Ser Val Phe Arg Arg Lys Ile Val Leu Trp Asn
2210                2215                    2220

Phe Val Ala Val Ile Leu Gln Asn Phe Phe Leu Ser Ala Pro Tyr
2225                2230                    2235

Gly Arg Asn Trp Gln Phe Leu Trp Thr Ser His His Ala His His
2240                2245                    2250

Trp Gln Ile Val Ile Leu Cys Val Val Phe Tyr Gly Phe Val Trp
2255                2260                    2265

Ala Gly Phe Leu Phe Val Val Ser Arg Tyr Phe Lys Ser His Ser
2270                2275                    2280

Trp Phe Leu Pro Val Phe Ala Cys Gly Leu Gly Ala Pro Arg Trp
2285                2290                    2295

Ala Gln Ile Trp Trp Gly Val Ser Gly Ile Gly Tyr Tyr Leu Pro
2300                2305                    2310

Trp Val Thr Gly Gly Tyr Thr Gly Gly Ala Leu Val Ser Arg Ser
2315                2320                    2325

Val Trp Leu Trp Leu Gly Val Leu Asp Ser Ile Gln Gly Leu Gly
2330                2335                    2340

Phe Gly Ile Ile Leu Leu Gln Thr Leu Thr Arg Met His Met Leu
2345                2350                    2355

Phe Cys Leu Val Cys Ser Gln Val Leu Gly Ser Ile Ala Thr Ile
2360                2365                    2370

Cys Ala Arg Ala Phe Ala Pro Asn Asn Val Gly Pro Gly Pro Val
2375                2380                    2385

Ser Pro Asp Pro Thr Phe Gly Gly Ser Ala Val Ala Asn Ala Trp
2390                2395                    2400

Phe Trp Val Ala Leu Phe Cys Gln Leu Leu Val Cys Ala Gly Tyr
2405                2410                    2415

Ile Leu Phe Phe Arg Lys Glu Gln Leu Ser Lys Pro
2420                2425                    2430

<210> SEQ ID NO 30
<211> LENGTH: 7585
<212> TYPE: DNA
<213> ORGANISM: Aspergillus oryzae

<400> SEQUENCE: 30

```
atgaagtggg ctttctccag tgcggtgctg gcgcttttcg caacaacagt aaaagcctgg      60
ccttacgaag aatctctctc cgcatacaac cttaacgaaa acaaatccgc gaccaacccg     120
gctcaatatt ggggagaatg gccggaccac aagggggaaat acttcccttc tcccgacaat    180
tggcgatttc ccgtctatac tctgttcatg gaccgctttg tcaacggaga ccctacgaac    240
gacaacatca atggaaccct cttcgagcac gatatctcct cgacacaaat gcgccatggt    300
ggagatgtgg ctggtctagt ggatactttg gattatcttc agggaatggg tatcaaggtt    360
cgtcattcgt tcaggttaat tacgtggcat gccatactga gaattcttag gccatctatc    420
tcgcaggaac catcttgatg aaccagccat ggggctctga tggttattcc gctctcgata    480
cgacactgct cgatcaacat tcggtgaca ttgcgacatg gcgtaatgct atcgacgaga      540
ttcataagcg cgggatgtat gtcatcttcg ataacacgat tgctacgtaa gtctcgccgc    600
atccacggta catatgagat gattgttaac gcttgtattc aggatgggtg atctcatcgg    660
cttcgagggc catctgaatg ataccacccc gttttcggtt aaggagcata aagcactttg    720
gaagagcaat cgtcgctatg tggatttcga tataggaaac gactataacc agacatgcga    780 ctaccccgt ttctggtacg aggacggtta tccagttcaa cagtctatga ctgaaggcct     840
tgttggttgt tatgacagcg actttgatca atatggtgat attgaggctt cggcgtgtt    900 ccctgattgg caacgtcagc tagcaaaatt cgcctccgtc caagatcgtc tgcgagaatg    960
gcacccctcg gtccgggagc ggttgattcg tcattcctgt atgattattt accagttgga   1020
tatcgacggt ttccgttatg ataaggctac tcagtcgacc gtggatgcgc taggagatat   1080
gtcgatggct tatcgcgaat gcgcccgtgc cgttggcaag gagaatttct tcatctccgg   1140
tgaaattact ggtggtaaca cttttggttc catctatttg ggccgaggta gacagccgaa   1200
ccagtatcct gagacggcgg agaaggccat gaaaatgacc aacgagtccg agtcgcaata   1260
cttcctgcgt gaagctggac atgaggcgat cgacggtgcg gccttccact attcgacata   1320
tcgtgccctg actcggttct tgggtatgga cggtaacttg gccgccggtt acgatgtacc   1380
tgtggattgg gtcgatgcgt ggaatctgat gttgcagtcg aacgacttca tcaaccctaa   1440
cacaggcaag tttgatcccc gccatatgtt cggcgcgacc aaccaggatg ttttccgctg   1500
gccgacagtc gaaaagggtg tggaaagaca gttgcttggg ctgtatatca ctaccttact   1560
tcttccgggt attcccctcc tcctttgggg cgaggaacag gcattctata tcttggatgc   1620
gacggcatct aactatatct atggccgtca agcaatgtcc cccgcgactg cgtggagaga   1680
ccacggttgc ttttccttgg attcctcaca gtattaccag tggcctattc aggccggtcg   1740
tgagggttgc catgacccaa ctgctgcgta cgatcatcgt gatccggccc acccggtgcg   1800
caacattatc aagcacatgt accagctgcg cgaagacttc cctgttctga atgatggcta   1860
ctccgtccag aaactctcga acctgaccga ggaggtcttc tatccgggtt ccaacgtac    1920 cgctacagaa acgggtttgt ggtctatcct acgtgatgtc aatgccgatg tgcaggacct   1980
aggctccgac gcgaagaatc aaccggtgtg gctcgtctac cacaacacca accgtacaat   2040
tgacttcaag ttcaactgca aggacaacga gactgcacta atctcgccct cgccaccgg    2100 caccaaagtt cgaaatctgt tctatcccta tgacgagcac accttgattg atggccccgt   2160
caagcttgga ctgaacggat ctaccgagct caatggctgc ctggccaaca tgacattgga   2220
cgcctatgag ttccgcgcct acgtcccag tgcacgtttc actaagcctc gtccaatgat    2280
cacccaattc actcccggcc atgacgtccc tgttcgctcc acggtggctc ccaatctgga   2340
```

```
tgaaagcgtg aagattgagc tctatttctc cgaagagatg gactgcgatt ctgtgaccaa    2400
agcgatttcc atcagctcat ctacggaatc taaaaaggtc ccgacgctgg atgagaagac    2460
tgtagactgc aagggaattc cagcaagcaa cacctcctgg actgggcagc ttcctagcgt    2520
cttcatgtgg gctgccaacc tgacgggagt gtataacggc atccaccgag tcacggttaa    2580
gaacgctagc agtactaatg gaaacgcgac aacaaacgcg gtcgaccact tcctcttccg    2640
tatcggacaa atcgataacc ccatggtctt tacatcggcc aactattcga ctagtttgct    2700
ccacgaggaa tcgaatggca ccctattcat ccagcaccac gcagctggtg ctgataagtg    2760
gcgttattcc accaattggg gcaccacttt ctccgagtgg aaggattaca caggtggtaa    2820
tgacactatc acggagttag aatggtctgg aaccaagaaa cagagatgga agggacacca    2880
tgtgcgggtc gagtactgga gcaaatggac cggtagcagc gattacgttc aggagggcga    2940
tgctggagtg cattcgaatg tgccacgccg cttcccccat atcttcttca acggccctta    3000
caatcagtac ggatatgacg gtggtcttga taacgtggtg aggcaggact ccaaagacgg    3060
actctggaaa tatcacttca cggcggagtg gccggctcaa gcccagctga acatctgggg    3120
catgaatccg gatggaaagc ctgatcaaag ctgggtgctg ggtgatgccg ataatgattc    3180
cgttctggat cgaatgccac cctcctctct ctctgcaacc ttgattaaca tcaccgagca    3240
tccgcctaag ccatatctgg cttggaatat ctacatcaac gatgcgacca tgaagttcca    3300
gctcttccct gttgggcacc agaacacgca gatcgccatg ttcgtgctct tctggatcat    3360
ccctgtcatc accggtgcag catgcgtcta cattttcatg aagtcttcct ataaggtcaa    3420
gttcaaccaa atcggtgtga gtgaaaaagc cacattgatc ccgttggcct tgcggagaaa    3480
gttcaagagg aatcgtggtg gtgatgagga aaggatgaac cccttgatgc gtctggccaa    3540
caagtccggt ttcctgcaga ccaacaccgc tattggcggc gctgcttctg gcaagcgacg    3600
catggttctt atcgcgacaa tggagtatga tatcgaggat tggcagatta agatcaagat    3660
tggtggtctt ggtgtcatgg cccagcttat ggggaaaact ctcggacatc aggacctgat    3720
ctgggttgtt ccctgtgtcg ggggagtcga atacccagtg gataaacccg ctgagcccat    3780
gaatgtcacg attcttggca actcttatga ggttcaggtc cagtaccatg tcttgaacaa    3840
tatcacctac gttctactag acgcccctgt gttccgccag caatcgaagt ccgaacccta    3900
tccagcccgt atggatgacc tcaacagtgc tatctactac tctgcctgga atcagtgtat    3960
cgctgaggcc tgcaagcggt tcccgattga cctgtaccat atcaacgatt atcacggttc    4020
tctagctccg ctctaccttc ttcccgatac agtaccggct tgtctttccc ttcacaacgc    4080
tgaattccag ggtctctggc caatgcgtac acagaaagaa aaggaggagg tgtgctccgt    4140
ctttaaccta gatattgata ttgtcagacg ttatgtgcag ttcggtgagg ttttcaactt    4200
gctgcactca ggtgctagtt atcttcgtgt tcaccagcag ggtttcggtg ccgtcggtgt    4260
gtccaagaag tacggaaagc ggtcctacgc ccgttatccc atcttctggg gtttgaggaa    4320
ggtcggcaac ttgcctaacc ctgatccttc ggatgtggga gaatggagta aggaaaaggc    4380
tattggtaac gctgacgagg tccatgtgga tcccgactat gaggccggca gggcagacct    4440
caaacgccag gctcaggaat gggctggtct tgatgtcaac cctgacgctg atctaatggt    4500
gttcgttggt cgttggtcca tgcagaaagg tgtcgattta atcgccgatg tgatgccagc    4560
tgttcttgaa gctcgcccta acgtgcaggt aatctgtgtt ggacctgtta tcgatcttta    4620
tggtaaattc gctgccctga agttggacca catgatgaag gtttaccctg gacgtgtgtt    4680
```

```
ctcgagacct gaattcaccg ctcttccgcc ttatatcttc tctggtgctg aattcgcgct    4740
tattccttct cgtgacgagc cctttggtct agtcgcagtc gagttcggcc gtaagggagc    4800
cttgggtatc ggtgcccgtg tcggtggtct cggtcagatg cctggatggt ggtataacgt    4860
cgaatctact gcgacatctc atcttctgta ccagttcaag cttgccatcg acgccgcact    4920
taactcgaaa caagagacca gagccatgat gcgtgcccgt tctgctaaac agcgattccc    4980
cgtcgcccaa tgggtcgagg acttggaaat cctgcaaacc accgcaatcc aagtacacaa    5040
caaggaattg gtcaagcaca acggtcgtcc gttcactccg actggaacga ctactcctag    5100
tggccttatg actcaacctg cgagccctct cgggacccca ggaatgcaaa ctcctcttgc    5160
tcattctagg gaaagcagct actcgaacct caaccgtcta agtgaatacg ttacccagcc    5220
aaagaccagc tacagcagag atcccagccc tagcggcacg gagaagccga atcaggact     5280
tcagcgacag cttctccttg gtgttcgctc tggacctggt catcagagcc gtcgtggtcg    5340
cgctcgccag cgtgacagca tcccagaaca cgaagacacc caggaagctc acggtggcgc    5400
cattactgat gttgaggaag aaagcagtga cgacgacatt gtcaaccatt acgcggatga    5460
cgagtatact cttacacctg cccaagtcga agaaggccgt aggttacagg ccgcccagca    5520
acaggctggt gtgcgcatgc cgttgagtcc aggtggtaga cgctacagcc aagactcgtt    5580
gcatccgaga aatgtccagc ctccttcgag tcccggaaca cccccagccg cttcccagag    5640
tctccttcct ccccctaggc tcctcgatcc cggcagtcgt ctcagtagcg catccgttct    5700
ctcacttgac tccgttgtcg gtggcaagaa ggacttcaag ctgcaaaagg ttgatccgtt    5760
cttcactgat agcaccggcg agtattacaa gatctttgat aagaagcttg atgaactcaa    5820
tggatcgaac tcggagtcgc aactgtgtat cgaagaatac ttgatcaaga gtgaaaagga    5880
atggttcgac aagttccgtg acgctagact tggtcgcact aaatcgccaa ctccctcagt    5940
ctatcgtgat aagcacggcg cttcccctat cggctcgttc tacgatgata acggctcccg    6000
tatgagtggt agcgatggcc ctcactccaa tgacagtgaa gacgacgagt tcctcctcgg    6060
aaaggactat gtccctccca ccggtctcaa gaagtggatg cagattcgca tcggtgactg    6120
gcctatctac tccttgttcc tcgctttagg ccaaatcatt gctgccaact cgtaccagat    6180
cacattgctc acgggcgaag tcggtcaaac tgccgagaaa ctgtacggaa ttgcaaccac    6240
gtatttgatc acgtctattc tctggtggct tgtgttccgc tacttcaaat ccgtcgtctg    6300
tctgtctgcg ccatggttct tgtacggtat cgccttcatc ttcattggat ccgcccattt    6360
tgagagcaac tctttcactc ggggatggat tcaaaatgtc ggtagtgggt tctacgccgc    6420
ggcctcgtct agtggttctt tcttcttcgc gctaaacttc ggtgatgaag gtggtgcacc    6480
tgtgaaaaca tggatcttcc gtgcatgtct cattcagggt atccagtccg cctatgttat    6540
tgctctctgg tactggggtt caaccctgtc acaggcacaa agtgagggtc tcttgactcc    6600
tacaaacaat atctccaatt cttggaagat taggtaggtt atattgatct ctttggttaa    6660
tttcactagc taactaatac tttcacagtg ccatctgtta ccccattgcc gcggcccttt    6720
tcggaattgg tttgctcttg acattcggcc tgcccaacta ttaccgtcaa acccctggca    6780
aggtcgcttc cttctacaaa tccgtgttcc gtcgtaagat cgtcctctgg aactttgtcg    6840
cggtcatcct tcagaacttc ttcctcagcg ccccctacgg ccgcaactgg cagtgtaagt    6900
tgaccccctgt ataacggttt ccatcatatc agaccaaact aactgtgtct ctttgcagtc    6960
ctctggacat cccaccacgc acatcactgg caaatcgtca tcctctgtgt tgttttctac    7020
ggcttcgtat gggcaggctt cctattcgtc gtcagtcgct acttcaaatc acacagctgg    7080
```

-continued

```
ttcctccccg tgttcgcctg tggcctcgga gctccccgct gggcacaaat ctggtggggt    7140
gtgtctggca ttggctacta cctcccttgg gtgacaggag gatataccgg cggcgcgctc    7200
gtctcccgaa gtgtctggct ctggctcggc gtgctggact cgatccaggg tctcggcttc    7260
ggtatcatcc tcttgcaaac cctgactcgc atgcacatgc ttttctgtct tgtttgttct    7320
caagtccttg gttctatcgc tacgatctgc gcgagagcct tcgcccctaa taatgtgggc    7380
ccagggccgg tttcgcctga tcctaccttt ggtgggagtg cggttgcgaa tgcctggttc    7440
tgggttgctc tgttttgtca gttgttggtc tggtaagtta ttcacatctt atgaactttg    7500
ttatatacaa cgatcgctaa cgtgtgatga ttacagtgcc ggttacatcc tcttcttccg    7560
gaaagaacag ctgtcaaagc cttaa                                         7585
```

<210> SEQ ID NO 31
<211> LENGTH: 2404
<212> TYPE: PRT
<213> ORGANISM: Aspergillus oryzae

<400> SEQUENCE: 31

```
Met Phe Leu Thr Val Met Gln Arg Ser Ala Ile Leu Ile Leu Ser Leu
1               5                   10                  15

Leu Ser Ala Thr Ala Leu Ser Trp Pro Tyr Thr Glu Ser Leu Val Asp
            20                  25                  30

Tyr Asn Leu Asn Glu Asn Lys Thr Ala Glu Ala Pro Ile Asp Tyr Trp
        35                  40                  45

Gly Glu Trp Pro Asp His Glu Tyr His Pro Ser Pro Asp Asn Trp Arg
    50                  55                  60

Phe Pro Ile Tyr Thr Ile Phe Leu Asp Arg Ile Ala Asn Gly Asp Pro
65                  70                  75                  80

Lys Asn Asp Asp Ile Asn Gly Thr Ala Phe Glu His Val Val Gly Ser
                85                  90                  95

Asn Gln Met Arg His Gly Gly Asp Leu Val Gly Leu Ile Asp Thr Leu
            100                 105                 110

Asp Tyr Ile Arg Gly Met Gly Phe Lys Gly Ile Tyr Phe Ala Gly Thr
        115                 120                 125

Tyr Leu Met Asn Leu Pro Trp Ala Tyr Asp Gly Tyr Ser Pro Val Asp
    130                 135                 140

Thr Thr Leu Leu Asp Met His His Gly Thr Leu Glu Asp Trp Arg Arg
145                 150                 155                 160

Thr Ile Thr Glu Ile His Lys Arg Asp Met Tyr Val Ile Val Asp Asn
                165                 170                 175

Thr Leu Ala Thr Met Ser Asn Leu Ile Gly Phe Lys Gly His Leu Asn
            180                 185                 190

Asp Ser Ala Asp Phe Arg Ala Asp Glu Tyr Glu Val Gln Trp Ile Ser
        195                 200                 205

Asp Arg Gln Tyr Ala Asp Phe Lys Phe Gly Asn Glu Tyr Asn Glu Thr
    210                 215                 220

Cys Asn Phe Pro Lys Phe Trp Asn Glu Thr Gly Tyr Pro Leu Thr Ser
225                 230                 235                 240

Gly Gly Val Glu Glu Leu Lys Gly Cys Tyr Asn Ser Asp Phe Asp Gln
                245                 250                 255

Phe Gly Glu Leu Glu Ala Phe Gly Asn Phe Pro Asp Trp Lys Arg Gln
            260                 265                 270

Leu Thr Lys Phe Ala Ser Val Gln Asp Arg Leu Arg Glu Trp His Lys
```

-continued

```
            275                 280                 285
    Pro Ile Arg Asp Val Ile Thr Lys His Ser Cys Ile Gln Ile Ala Ser
    290                 295                 300

Leu Asp Ile Asp Gly Phe Arg Phe Asp Lys Ala Val Gln Thr Thr Leu
    305                 310                 315                 320

Glu Pro Leu Ser Glu Ile Thr Ala Val Tyr Arg Glu Cys Ala Lys Lys
                        325                 330                 335

Tyr Gly Lys His Asn Phe Phe Leu Pro Gly Glu Ile Thr Ser Gly Asn
                        340                 345                 350

Thr Phe Gly Ser Leu Tyr Leu Gly Arg Gly Arg Gln Pro Asp Gln Gln
                        355                 360                 365

Pro Glu Ser Ala Asp Ala Gly Val Lys Leu Lys Asn Ser Ser Asp Gly
    370                 375                 380

Tyr Phe Leu Arg Asp Asp Gly Tyr Gln Ala Leu Asp Ser Ala Ala Phe
    385                 390                 395                 400

His Tyr Thr Ile Tyr Arg Ser Met Thr Arg Phe Leu Gly Met Asp Gly
                        405                 410                 415

Asn Leu Val Ala Gly Phe Asp Leu Pro Thr Asp Phe Ile Glu Ala Trp
                        420                 425                 430

Asn Gly Met Leu Val Ser Asn Asp Phe Leu Asn Ala Tyr Thr Gly Glu
                        435                 440                 445

Val Asp Pro Arg His Met Phe Gly Val Ser Asn Gln Asp Asn Phe Arg
    450                 455                 460

Trp Pro Ala Ile Val Asn Gly Thr Glu Lys Tyr Leu Leu Gly Leu Tyr
    465                 470                 475                 480

Ile Val Thr Leu Glu Leu Pro Gly Ile Pro Leu Ile Leu Trp Gly Glu
                        485                 490                 495

Glu Gln Ala Met Tyr Val Phe Glu Ser Thr Ala Ser Asn Tyr Leu Phe
                        500                 505                 510

Gly Arg Gln Pro Met Thr Tyr Gln Thr Ala Trp Trp Thr His Gly Cys
                        515                 520                 525

Met Thr Leu Asn Thr Ser Lys Phe Tyr Asp Phe Pro Asn Glu Lys Gly
    530                 535                 540

Leu His Gly Cys Glu Asp Ile Thr Val Thr Tyr Asp Gln Arg Asn Pro
    545                 550                 555                 560

Ala His Pro Leu Arg Asn Ile Met Lys Arg Met Phe Glu Ile Arg Glu
                        565                 570                 575

Gln Tyr Pro Val Ala Asn Asp Gly Phe Tyr Leu Gln Thr Leu Ser Gln
                        580                 585                 590

Leu Thr Lys Asp Val Tyr Leu Pro Gly Ser Thr Asp Thr Pro Thr Val
                        595                 600                 605

Thr Gly Leu Trp Ser Val Leu Arg Ser Tyr Phe Pro Gly Val Gln Lys
    610                 615                 620

Glu Ala Ser Lys Asn Ser Gln Asn Leu Trp Leu Val Tyr His Asn Ala
    625                 630                 635                 640

Asn Lys Thr Glu Thr Tyr Gly Gly Asp Cys Lys Lys Asp Thr Ala
                        645                 650                 655

Leu Leu Ser Pro Phe Lys Ser Gly Thr Lys Leu Lys Asn Leu Phe Tyr
                        660                 665                 670

Pro Tyr Asp Glu Leu Thr Leu Glu Asp Gly Pro Gly Glu Ile Ala Val
                        675                 680                 685

His Asn Ser Thr Glu Ser Tyr Gly Cys Ile Arg Ser Met Lys Leu Leu
                        690                 695                 700
```

```
Pro Trp Glu Tyr Arg Ala Tyr Ile Glu Ala Glu Asn Phe Val Glu Pro
705                 710                 715                 720

Gly Pro Thr Val Thr Glu Phe Val Pro Gly His Asp Ala Arg Leu Leu
                725                 730                 735

Ser Thr Asp Asp Ser Gly Gln Thr Val Asp Ile Gln Leu Gly Tyr Ser
            740                 745                 750

Lys Glu Met Asp Cys Asp Lys Ile Ala Asp Ala Ile Ser Leu Asn Ser
        755                 760                 765

Thr Thr Val Lys Gly Val Thr Ala Ser Leu Asp Thr Ser Ser Val Ser
770                 775                 780

Cys Asn Lys Ile Ser Pro Arg Thr Ser Ser Asp Asn Phe Val Gly Glu
785                 790                 795                 800

Val Pro Thr Val Trp Thr Trp Ser Ala Lys Leu Lys Asn Val His His
                805                 810                 815

Gly Ile His Gln Leu Thr Val Lys Asn Val Ser Thr Thr Ser Gly Val
            820                 825                 830

His Thr Asp Ala Val Asp Gln Phe Leu Phe Arg Val Gly Ser Gln Asn
        835                 840                 845

Asn Pro Leu Leu Ser Pro Leu Ser Asn Tyr Ser Thr Ser Leu Val Gln
850                 855                 860

Lys Ser Asp Asn Gly Ser Phe Tyr Ile Gln His Asp Ala Ala Gly Ala
865                 870                 875                 880

Asp Lys Phe Arg Tyr Ser Thr Asp Phe Gly Leu Asn Trp Ser Asn Trp
                885                 890                 895

Thr Thr Tyr Thr Gly Asp Asn Thr Leu Val Asp Phe Pro Glu Trp Thr
            900                 905                 910

Gly Thr Asp Ala Gln Lys Trp Lys Gly Thr His Ile Arg Val Gln Tyr
        915                 920                 925

Phe Ser Arg Leu Thr Gly Ser Ser Asp Tyr Ile Gln Glu Gly Asp His
930                 935                 940

Gly Trp Glu Lys Gly Val Ala Arg Arg Phe Pro Asn Leu Phe Trp Asn
945                 950                 955                 960

Gly Pro Phe Asn Gln Tyr Gly Tyr Asp Ala Gly Leu Asp Asn Lys Met
                965                 970                 975

Arg Tyr Asp Thr Lys Asp His Arg Trp Lys Tyr Asp Phe Val Tyr Glu
            980                 985                 990

Trp Pro Ala Ile Gly Gln Met Ser Val Trp Gly Met Leu Lys Asp Gly
        995                 1000                1005

Arg Pro Asp Val Thr Glu Val Tyr Gly Asp Val Asp Asn Ser Ser
    1010                1015                1020

Val Val Gln Lys Leu Pro Pro Ser Tyr Leu Ser Ser Asn Val Ile
    1025                1030                1035

Asn Ile Thr Lys Leu Pro Pro Phe Pro His Leu Gly Trp Thr Ile
    1040                1045                1050

Thr Leu Asn Asp Ala Asn Leu Arg Tyr Glu Met Leu Pro Val Gly
    1055                1060                1065

Ser Gly Trp Ala Gln Leu Val Leu Tyr Ile Leu Leu Trp Val Leu
    1070                1075                1080

Pro Ile Leu Met Gly Phe Ala Gly Ile Phe Ile Phe Ile Arg Thr
    1085                1090                1095

Phe Tyr Arg Val Lys Leu Asn Thr Asp Gly Asp Val Ala Lys Glu
    1100                1105                1110
```

-continued

Asp Lys Leu Pro Leu Leu Phe Trp Arg Arg Val Arg Glu Lys Phe
1115                1120                1125

Ser Gly Asp Asp Glu Ser Asp Lys Ser Ile Ser Asp Lys Asp Ile
1130                1135                1140

Pro Thr Asp Ile Ala Ile Ala Gly Ala Pro Glu Gln Arg Arg Thr
1145                1150                1155

Val Leu Ile Ala Thr Met Glu Tyr Asn Ile Glu Asp Trp Lys Val
1160                1165                1170

Lys Val Lys Ile Gly Gly Leu Gly Val Met Ala Gln Leu Met Ser
1175                1180                1185

Gln His Leu Lys His Gln Asn Leu Ile Trp Val Pro Cys Val
1190                1195                1200

Gly Asp Ile Glu Tyr Pro Gln Asp Thr Pro Ser Glu Pro Phe Val
1205                1210                1215

Val Thr Ile Leu Asp Lys Pro Tyr Phe Ile Asn Val Gln Tyr His
1220                1225                1230

Ile Val Asp Asn Ile Thr Tyr Val Leu Leu Asp Ala Pro Val Phe
1235                1240                1245

Arg Gln Gln Thr Lys Ala Glu Pro Tyr Pro Pro Arg Met Asp Asp
1250                1255                1260

Leu Asp Ser Ala Ile Tyr Tyr Ser Ala Trp Asn Gln Cys Ile Ala
1265                1270                1275

Glu Thr Ile Lys Arg Phe Pro Ser Ile Asp Leu Tyr His Ile Asn
1280                1285                1290

Asp Phe His Gly Cys Leu Ala Pro Leu Tyr Leu Pro Thr Arg
1295                1300                1305

Thr Ile Pro Val Cys Leu Ser Leu His Asn Ala Glu Phe Gln Gly
1310                1315                1320

Leu Trp Pro Leu Arg Asn Pro Gln Glu Lys Lys Glu Val Cys Ser
1325                1330                1335

Val Phe Asn Leu Pro Ile Glu Thr Ala Thr Lys Tyr Ser Gln Phe
1340                1345                1350

Gly Asn Val Phe Asn Leu Leu His Thr Gly Ala Ser Tyr Val Arg
1355                1360                1365

Phe Tyr Gln Arg Gly Phe Gly Ala Val Gly Val Ser Lys Lys Tyr
1370                1375                1380

Gly Lys Arg Ser Trp Ala Arg Tyr Pro Ile Phe Trp Ser Leu Glu
1385                1390                1395

Lys Ile Gly Ser Leu Pro Asn Pro Asp Pro Ser Asp Thr Gly Asp
1400                1405                1410

Met Thr Asn Asn Ala Asp Ala Glu Val Pro Ile Gln Ser Tyr Glu
1415                1420                1425

Glu Arg Ile Asn Asp Lys Leu Gln Ala Gln Lys Trp Ala Gly Leu
1430                1435                1440

Asn Glu Asp Arg Asp Ala Asp Leu Leu Val Phe Val Gly Arg Trp
1445                1450                1455

Ser Lys Gln Lys Gly Val Asp Leu Ile Ala Asp Val Met Pro Ala
1460                1465                1470

Ile Leu Ser Ala Arg Pro His Val Gln Leu Ile Cys Val Gly Pro
1475                1480                1485

Ile Val Asp Leu Tyr Gly Arg Leu Ala Ala Thr Lys Leu Glu Arg
1490                1495                1500

Ile Met Glu Met Phe Pro Gly Arg Val Phe Ser Lys Pro Glu Phe

-continued

```
            1505                1510                1515
Thr Val Leu Pro Pro Tyr Val Phe Ser Gly Ala Asp Phe Ala Leu
        1520                1525                1530
Ile Pro Ser Arg Asp Glu Pro Phe Gly Leu Val Ala Val Glu Phe
        1535                1540                1545
Gly Arg Lys Gly Ala Leu Gly Ile Gly Ser Arg Ile Gly Gly Leu
        1550                1555                1560
Gly Gln Met Pro Gly Trp Trp Tyr Thr Val Glu Ser Asp Ala Thr
        1565                1570                1575
Arg His Leu Leu His Gln Leu Lys Thr Ala Ile Lys Gln Ala Leu
        1580                1585                1590
Asp Ser Ser Gln Asp Ala Arg Glu Glu Met Arg Ala Asn Ser Val
        1595                1600                1605
Arg Gln His Phe Pro Val Leu Glu Trp Ile Gln Lys Leu Glu Ala
        1610                1615                1620
Leu Gln Arg Thr Ala Ile Gln Ile His His Thr Lys Asn Lys Asn
        1625                1630                1635
Thr Val Thr Gly Pro Met Pro Glu Ser Gln Asn Tyr Trp Glu Thr
        1640                1645                1650
Gln Ser Val Arg Met Ser Thr Leu Gly Leu Pro Gly Pro Thr Gln
        1655                1660                1665
Ser Val Thr Glu Gly Leu Asp Thr Pro Pro Gly Arg Leu Leu Thr
        1670                1675                1680
Pro Gly Gln Ser Arg Phe Ala Glu Leu Gln Leu Glu Gly Ala Asp
        1685                1690                1695
Gly Asn Arg Asn Ser Ser Leu Gly Arg Lys Leu Ser Leu Gly Arg
        1700                1705                1710
Arg Ser Gly Pro Gly Gln Asp Arg Lys Arg Pro Gly Lys Ser Pro
        1715                1720                1725
Pro Arg Glu Ser Gln Ile Leu Gly Glu Asp Leu Glu Gly Glu Asn
        1730                1735                1740
Thr Asp Ala Glu Glu Glu Gly Thr Thr Thr Pro Gln Val Asn Tyr
        1745                1750                1755
Ile Ser Pro Glu Glu Ala Met Ala Ala Val Asn Asn Thr Leu Gly
        1760                1765                1770
Thr Gln Asp Ile Gly Met Ala His Thr Asn Asn Ser Thr His Ser
        1775                1780                1785
Leu Ala Gly Pro Gln Gly Ser Thr Tyr Met Ser Val Pro Gly Ser
        1790                1795                1800
Pro Asn Asn Met Ser Arg Ala Ser Ser Pro Met Pro Gly Thr Pro
        1805                1810                1815
Gly Leu Pro Gln Tyr Pro Phe Gln Phe Ala Leu Gly Ser Gly Gly
        1820                1825                1830
Asn Thr Pro Phe Thr His Ser Arg Asn Val Ser Met Leu Ser Leu
        1835                1840                1845
Pro Ser Val Val Ala Asp His Asn Gln Pro Val Phe Glu Leu Gln
        1850                1855                1860
Lys Val Asp Pro Thr Phe Thr Asp Ser Thr Arg His Phe Thr Arg
        1865                1870                1875
Arg Phe Glu Glu Ile Leu Asn Asn Leu Asn Lys Lys Asn Ser Met
        1880                1885                1890
Thr Asp Cys Cys Ile Glu Thr Tyr Leu Met Lys Ser Glu Arg Lys
        1895                1900                1905
```

-continued

```
Phe Tyr Asp Met Tyr Asn Asp Ala Gln Leu Lys Lys Gln Pro Asp
    1910            1915               1920

Asp Arg Ala Val Ser Asp Ser Asn Ser Asp Thr Gln Asp Asn Arg
    1925            1930               1935

Ala Ser Tyr Ala Thr Val Thr Gly Gly Ser Asp Ser Asn Asp Pro
    1940            1945               1950

Asp Glu Ile Asp Leu Trp Leu Ser Arg Leu Gly Tyr Lys Arg Pro
    1955            1960               1965

Ile Ala Ile Gln Arg Phe Met Arg Arg Arg Leu Gly Lys Trp Pro
    1970            1975               1980

Val Tyr Ala Leu Phe Leu Gly Leu Gly Gln Ile Ile Ala Thr Asn
    1985            1990               1995

Ser Ala Gln Met Thr Leu Leu Val Gly Gln Val Gly Glu Thr Ala
    2000            2005               2010

Thr Lys Leu Tyr Ile Ile Ala Thr Ile Tyr Cys Ile Ser Ser Ile
    2015            2020               2025

Cys Trp Trp Leu Leu Phe Tyr Arg Phe Pro Ser Val Ile Val Leu
    2030            2035               2040

Thr Leu Pro Trp Phe Ile Tyr Cys Met Ala Phe Ile Ile Ile Gly
    2045            2050               2055

Val Ser Pro Phe Ala Leu Thr Ser Leu Gly Arg Ala Trp Ala Gln
    2060            2065               2070

Asn Val Ala Ala Gly Val Tyr Ser Ala Ala Ser Ser Gly Ser
    2075            2080               2085

Leu Phe Phe Ala Leu Asn Phe Gly Asp Gln Gly Ala Val Pro Ile
    2090            2095               2100

Lys Asp Trp Met Phe Arg Ala Ser Leu Ile Gln Gly Ile Gln Gln
    2105            2110               2115

Leu Tyr Thr Val Ala Leu Trp Tyr Trp Ser Ser Lys Val Thr Glu
    2120            2125               2130

Ala Glu Val Gly Gly Val Ser Thr Ala Ala Leu Ser Ser Trp Arg
    2135            2140               2145

Leu Thr Ala Val Val Met Pro Ile Ala Ala Val Cys Phe Ile Val
    2150            2155               2160

Gly Val Leu Leu Ala Leu Gly Leu Pro Lys Tyr Tyr Arg Gln Ser
    2165            2170               2175

Pro Gly Arg Ile Leu Phe Phe Tyr Thr Ser Leu Phe Arg Arg Arg
    2180            2185               2190

Ile Val Leu Trp Phe Phe Phe Met Val Ile Val Gln Asn Trp Phe
    2195            2200               2205

Leu Ser Ala Ala Phe Gly Arg Asn Trp Ser Phe Leu Trp Ser Ser
    2210            2215               2220

Gln His Ala Lys Ala Trp Glu Val Val Ile Leu Val Ile Phe Phe
    2225            2230               2235

Phe Val Val Leu Trp Val Ile Ile Leu Ile Ile Phe Arg Ala Leu
    2240            2245               2250

Ser Lys Glu His Ser Trp Ile Leu Pro Val Phe Gly Leu Ser Leu
    2255            2260               2265

Gly Ala Pro Arg Trp Ala Gln Thr Trp Gly Thr Ser Asn Ile
    2270            2275               2280

Gly Tyr Tyr Leu Pro Trp Ala Gly Ser Leu Thr Ser Gly Ala Leu
    2285            2290               2295
```

| | | | | | | | | | | | |
|---|---|---|---|---|---|---|---|---|---|---|---|
| Val | Ser | Arg | Cys | Val | Trp | Leu | Trp | Leu | Gly | Val | Leu | Asp | Glu | Ile |
| | 2300 | | | | 2305 | | | | 2310 | | |

| Gln | Gln | Val | Gly | Leu | Gly | Met | Ile | Leu | Leu | Gln | Thr | Leu | Thr | Arg |
| | 2315 | | | | 2320 | | | | 2325 | | |

| Val | His | Val | Cys | Phe | Val | Leu | Leu | Ala | Ala | Gln | Ala | Leu | Gly | Ser |
| | 2330 | | | | 2335 | | | | 2340 | | |

| Ile | Ala | Thr | Ile | Cys | Ala | Arg | Gly | Phe | Ala | Pro | Asn | Lys | Leu | Gly |
| | 2345 | | | | 2350 | | | | 2355 | | |

| Pro | Ala | Gly | Ile | Ser | Pro | Asn | Val | Gly | Thr | Ser | Leu | Asp | Thr | Val |
| | 2360 | | | | 2365 | | | | 2370 | | |

| Gly | Asn | Ala | Trp | Phe | Trp | Ile | Ala | Leu | Phe | Phe | Gln | Leu | Leu | Ala |
| | 2375 | | | | 2380 | | | | 2385 | | |

| Ser | Trp | Gly | Phe | Leu | Leu | Phe | Tyr | Arg | Arg | Glu | Gln | Leu | Asn | Arg |
| | 2390 | | | | 2395 | | | | 2400 | | |

Pro

<210> SEQ ID NO 32
<211> LENGTH: 7369
<212> TYPE: DNA
<213> ORGANISM: Aspergillus oryzae

<400> SEQUENCE: 32

```
atgttcctca cggtgatgca gcgctcagcg atccttatcc tgtcgttact gagcgctacc      60
gccttaagct ggccatacac tgagtcgctc gttgactata acctgaatga aaataaaacc     120
gccgaagcgc cgattgatta ttggggagag tggccggatc atgaatatca cccgtcgccc     180
gataactggc gctttccgat ctataccatc tttttggacc gcatcgctaa cggtgacccg     240
aagaatgatg atatcaatgg caccgccttt gagcatgtgg ttggctcgaa tcaaatgcgc     300
cacggggcg atttggttgg tctaattgat acgctggatt atattagggg catgggtttc     360
aaggtgtgtt gagccgattg tgatccgatc ttggtgctta ctctggtagg gcatttactt     420
cgctggaacg tacttgatga accttccctg ggcctacgat ggctactcac cggttgatac     480
cactttgctc gacatgcacc atggcacact cgaggattgg agacggacca tcactgagat     540
ccacaaacga gatatgtatg tgatcgtgga taatacactg gcaacgtaag tacatatccc     600
aggtgtctca gatcaacact ggttgacgag tatatgcaga atgagcaacc ttattggttt     660
caaaggacat ctcaacgatt cagccgattt tcgagcagat gaatatgaag tgcagtggat     720
ctcagataga cagtacgcgg acttcaaatt cggaaatgag tacaacgaga cctgcaactt     780
cccgaagttt tggaatgaga ctgggtatcc gttgacatca ggtggtgttg aggagctgaa     840
agggtgctat aatagcgatt tcgatcaatt tggagagctg gaggcgttcg gtaactttcc     900
agactggaag cgccagctta ccaagttcgc ctcggtgcaa gatcgtctgc gtgaatggca     960
caagcctatt cgtgatgtca tcactaagca ttcttgcatt cagatcgcta gtctagatat    1020
cgatggtttc cgtttcgata aagccgttca gacaaccctc gagcccctaa gtgaaataac    1080
cgccgtctac cgtgagtgtg cgaagaaata tggcaagcat aacttttcc ttcccggtga    1140
gatcacatca ggaaatacct ttggcagtct ttaccttgga cgcggtcgtc agccagatca    1200
gcagcctgaa tctgcagatg ctggtgttaa gttgaagaat agttcggacg atatttttct    1260
cagagacgat ggataccagg cgttggactc agccgcgttt cactacacga tctaccgttc    1320
gatgactcgt ttcctgggaa tggatggtaa tctagtggct ggctttgact tgcctactga    1380
ttttatcgag gcctggaatg ggatgctcgt cagcaacgac ttcctcaatg catacacggg    1440
```

-continued

```
tgaagtagac ccgaggcaca tgtttggtgt ctcaaaccag acaactttc gctggccagc    1500 aatcgtaaat ggcaccgaga aatatcttct gggtctttat atcgtcacct tggagctccc    1560
tggaattcct ctgatcctat ggggcgaaga gcaggcgatg tatgttttg aatctactgc    1620 ttctaactac ctgttcggcc ggcagccaat gacgtatcag acggcatggt ggacacatgg    1680
atgcatgact ttgaatacat ccaaattcta cgatttccct aatgagaagg gactacacgg    1740
ctgcgaggat atcaccgtta cgtatgatca gcggaatccg gcacacctc tgcgcaatat    1800 catgaagcgc atgttcgaaa ttcgggagca gtatccggta gcaaatgatg ggttttatct    1860
tcaaacgctt tctcagctga caaaggatgt gtaccttcct ggttcaacgg acacgccgac    1920
tgtgactggt ctatggtcgg ttctgcggag ctacttccca ggcgtccaga aggaggcaag    1980
caagaacagt cagaaccttt ggcttgtgta tcataatgct aacaaaactg aaacctacgg    2040
tggtgactgc aaaaagaaag ataccgcctt gctgtcgcct ttcaagtcgg gaactaagct    2100
gaagaatctc ttctatccgt acgatgagct cactttagaa gatggtccgg gcgaaatcgc    2160
agtccacaat agcactgaga gctatggatg catccgcagt atgaaattgc ttccatggga    2220
ataccgtgcc tacatagagg ccgagaactt cgttgagccc ggccctactg ttactgagtt    2280
cgttcctggc cacgacgccc gattgttgtc tacggatgac agtggccaaa ctgtcgacat    2340
ccagctcgga tattcaaaag agatggactg tgacaagatc gccgatgcca tctctttgaa    2400
ctcaacgaca gtgaagggag ttacagcttc ccttgacaca tctagcgtgt cttgcaacaa    2460
aatctcccca aggacaagca gtgataactt tgttggggag gttccaaccg tttggacatg    2520
gtctgccaag ctgaaaaatg tccaccacg aatccatcag ctgacagtta agaacgtttc    2580
cacgacgtct ggagttcata ccgatgcggt tgaccagttc ttattccgtg tcggaagtca    2640
aaacaatccc cttttatccc cactgtccaa ttattccacc agtcttgtgc agaaatccga    2700
caacggcagc ttctatatcc agcatgacgc cgctggtgct gataaatttc gctactcgac    2760
tgattttggc cttaactggt ccaactggac aacgtatacc ggtgacaaca ccctagtcga    2820
cttcccagag tggaccggaa cagacgctca gaagtggaag ggaactcata ttcgcgtaca    2880
gtacttttca aggctcaccg gcagtagtga ttacattcag gaaggtgatc atggctggga    2940
aaaaggtgtt gctcgaagat ttcctaacct cttttggaac ggtccgttca atcaatatgg    3000
ttacgatgcg ggactggata caagatgag atacgatacc aaggatcatc gttggaagta    3060
cgattttgtc tacgagtggc cggccattgg acaaatgagt gtctggggaa tgttaaagga    3120
tgggcggccc gacgttacag aggtgtatgg tgatgtcgac aactcatctg tagttcagaa    3180
acttcctccg tcttacctat cgtccaacgt gatcaatatc acaaagctgc ctccattccc    3240
gcacctcggc tggaccatca cgctcaatga cgccaacttg agatatgaga tgcttccggt    3300
cggatctgga tgggcccagc tcgtgctata cattcttctc tgggtgcttc caattctcat    3360
gggatttgct ggtatcttca tcttcatcag gacattctac cgtgttaaac tcaataccga    3420
tggcgatgtg gccaaagaag ataagctacc gctcctgttt tggcggaggg tcagagaaaa    3480
gttctccggc gacgacgagt cggataagtc gatatcagat aaggatatac cgacagacat    3540
tgctatcgcg ggagcccctg agcaacgtcg tacagtattg atcgccacca tggaatacaa    3600
catcgaagac tggaaggtca aggtcaagat cggcggtcta ggcgtcatgg cacaactcat    3660
gtctcagcat ctgaagcatc aaaacttgat ctgggttgtt ccttgcgttg gtgacattga    3720
atatcctcag gacacgccat ccgagccttt cgtggtcact atcctggaca agccatattt    3780
tatcaatgtg caatatcata tagttgataa catcacctat gtcctgctcg acgctccagt    3840
```

| | |
|---|---|
| tttccgccaa cagaccaaag cagagccata tcctcctcgc atggatgatc ttgacagtgc | 3900 |
| aatctactat tcggcatgga accaatgtat cgcagagacg atcaaacgat tcccgtcaat | 3960 |
| cgatctctat catatcaacg atttccatgg ttgtttagca ccactgtatt tgcttcccac | 4020 |
| gcgtaccatc ccgtgtgcc tgtccttaca taatgctgaa ttccagggtc tttggcccct | 4080 |
| gagaaacccc caggaaaaga aggaagtctg ttcggtcttc aaccttccca tcgaaactgc | 4140 |
| aaccaagtac agtcaatttg gaaacgtctt caaccttctt cacactggtg cgagctatgt | 4200 |
| gcgattctac caacgcggtt tcggcgcagt aggtgtgtcc aaaaagtatg gaaagcgctc | 4260 |
| atgggctaga tacccgattt tctggagtct tgaaaagatt ggcagtcttc caaacccaga | 4320 |
| cccctccgac acaggggaca tgacaaataa cgcagacgcc gaggttccaa tccagtccta | 4380 |
| cgaagaacga atcaatgata agctacaggc ccagaagtgg gctggtttga atgaagatcg | 4440 |
| tgatgctgac ctacttgtgt cgtcgggcg atggtcgaag cagaagggag tggatttgat | 4500 |
| tgcagatgtc atgccagcga tattatccgc cagaccccac gtgcaattga tctgcgttgg | 4560 |
| acctatcgtt gatctctatg gtagactggc tgctacaaag ctagagcgca tcatggaaat | 4620 |
| gttccctggt cgcgtcttct ctaagccaga gttcaccgtt ttgcctccat acgtatttc | 4680 |
| tggtgccgac ttcgctctga ttccctccag agacgaacca tttgggttag tcgctgtaga | 4740 |
| gttcggccgt aagggtgcac tgggaatcgg ttctcgcatt ggaggtttag gccagatgcc | 4800 |
| aggttggtgg tacaccgtgg aatccgacgc aacccgccat cttctgcatc agttgaagac | 4860 |
| cgctatcaaa caagcgttgg actcatcaca ggacgctcgt gaggagatgc gcgccaattc | 4920 |
| cgtcaggcaa catttccccg ttcttgaatg gattcagaaa ctcgaagcct tgcaacgaac | 4980 |
| agcgatccaa atccatcaca ccaagaacaa gaacaccgtg acaggcccga tgccagagtc | 5040 |
| gcagaactat tgggagactc aaagcgtacg aatgtctacg ctgggccttc caggacctac | 5100 |
| ccagtcggtg acagagggtt tggatacacc gccaggaagg cttttgacgc ccggccagtc | 5160 |
| tcgatttgca gaattgcaat tggagggagc tgatggcaac aggaacagca gcctgggtcg | 5220 |
| caaactctcg ctcggtcggc gatctggacc tggtcaggac agaaaacgtc ccggcaagag | 5280 |
| cccgccgcgc gagagccaga tcctaggaga ggatttggaa ggtgagaaca cggatgccga | 5340 |
| agaagagggc accactacgc cgcaggtgaa ctatatttca cctgaagaag ctatggctgc | 5400 |
| agttaacaac actttgggaa ctcaagatat cggaatggca cacacgaaca atagtactca | 5460 |
| ctcgctcgct ggtcctcaag gatctactta catgtccgtg ccaggctcac caaacaacat | 5520 |
| gtcacgggcc tcctctccaa tgccaggaac cccggggctg ccccaatacc cattccagtt | 5580 |
| cgcattgggt tctggcggaa atactccttt cactcactcc cgcaatgtgt ccatgctttc | 5640 |
| cttgccttca gtcgtggcgg accacaacca gccggttttt gagctgcaaa aggttgatcc | 5700 |
| gacctttaca gacagcacac gccacttcac gcgacgcttc gaagagattc tcaacaacct | 5760 |
| gaacaagaag aactcgatga cagactgctg tatcgagacg tacctaatga gagcgagcg | 5820 |
| taaattctac gacatgtaca acgatgcaca attaaagaaa cagcccgatg atcgtgcagt | 5880 |
| gtctgattcg aattcagaca ctcaagataa ccgcgcctcg tacgccactg tcactggagg | 5940 |
| ttcggactcg aatgatccgg atgagattga tttatggctc tctcgactgg ggtataaacg | 6000 |
| accgattgct attcaaagat tcatgagaag gcgtcttggc aaatggcctg tctacgctct | 6060 |
| attcctgggt cttggacaaa tcatcgcgac caactccgct caaatgaccc tgttggtcgg | 6120 |
| tcaggtagga gaaacagcaa ccaagttgta cattatcgcc acgatctact gcatttcctc | 6180 |

-continued

```
tatctgttgg tggctcctct tctatcgatt cccgtcagta atcgtcctca ctctcccctg   6240
gttcatttac tgcatggcat ttatcatcat tggcgtctct ccattcgctc tcacatctct   6300
cggtcgagcc tgggcccaga acgtcgctgc aggtgtgtat tccgccgcat catctagcgg   6360
ctcgttattc ttcgccctca acttcggtga tcagggtgcc gttcctataa aggattggat   6420
gttccgcgca agtctcatcc agggaatcca gcagctctac accgtcgcct tatggtactg   6480
gagctcgaag gtgaccgaag cagaggtggg aggcgtgtcc accgcggctc taagctcatg   6540
gagactcaca gctgtggtga tgcccatcgc cgcagtatgt ttcatagtcg gcgtgcttct   6600
cgcgctcggc ctaccaaaat actaccgcca atccccggt aggatcctct tcttctacac   6660
atccctcttc cgccgccgta ttgtcctctg gttcttcttc atggtaatag tccagaactg   6720
gttcctctcc gcagcatttg gtcgcaattg gtcattcctc tggtcctccc aacacgctaa   6780
ggcatgggag gtcgtcatcc tagtcatctt tttcttcgtc gtcctctggg taatcatcct   6840
catcatattc cgcgccctat ccaaggaaca cagctggatt ctacccgtat ttggtctgag   6900
tctcggcgca ccgcgctggg cccaaacatg gtggggaacg tccaacatag gctactacct   6960
gccatgggcg ggaagtctga catccggtgc cctcgtgtcg agatgcgtct ggctctggct   7020
cggtgtgctt gacgaaatcc agcaagtcgg cctgggtatg atcctcctac agacactgac   7080
cagagtccac gtgtgcttcg ttctgttggc cgcacaggct ctcggatcca tcgctacgat   7140
ctgcgcccgt ggattcgcgc cgaataagct cgggcccgcg ggaatctcgc cgaacgtggg   7200
aacgtctcta gatacagttg gaaatgcgtg gttctggatc gcgctcttct tccagcttct   7260
ggctaggtaa ggcttctgta ttcccggctt caatggattc aatactaatg tggttcatag   7320
ttggggcttc cttttgttct atcgtcgtga gcagcttaat aggccttaa               7369
```

<210> SEQ ID NO 33
<211> LENGTH: 60
<212> TYPE: DNA
<213> ORGANISM: Artificial
<220> FEATURE:
<223> OTHER INFORMATION: primer

<400> SEQUENCE: 33

```
atgtaagcgt gacataacta attacatgat gcggccctct cgataagggc gttacggctc   60
```

<210> SEQ ID NO 34
<211> LENGTH: 40
<212> TYPE: DNA
<213> ORGANISM: Artificial
<220> FEATURE:
<223> OTHER INFORMATION: primer

<400> SEQUENCE: 34

```
ccgagactcc tcattggagt taacgagctc acgatgctcc                         40
```

<210> SEQ ID NO 35
<211> LENGTH: 40
<212> TYPE: DNA
<213> ORGANISM: Artificial
<220> FEATURE:
<223> OTHER INFORMATION: primer

<400> SEQUENCE: 35

```
gctggcgtaa tagcgaagag aagtcggcgt ctggtcagtc                         40
```

<210> SEQ ID NO 36
<211> LENGTH: 67

```
<212> TYPE: DNA
<213> ORGANISM: Artificial
<220> FEATURE:
<223> OTHER INFORMATION: primer

<400> SEQUENCE: 36
actactagca gcagctgtaa tacgactcac tcactatagg gaatattggt catatccaga      60
gtcgcct                                                                67

<210> SEQ ID NO 37
<211> LENGTH: 60
<212> TYPE: DNA
<213> ORGANISM: Artificial
<220> FEATURE:
<223> OTHER INFORMATION: primer

<400> SEQUENCE: 37
atgtaagcgt gacataacta attacatgat gcggccctct tccttcgcca ttcacacgtc      60

<210> SEQ ID NO 38
<211> LENGTH: 45
<212> TYPE: DNA
<213> ORGANISM: Artificial
<220> FEATURE:
<223> OTHER INFORMATION: primer

<400> SEQUENCE: 38
cctaaccgag actcctcatt ggagtaacag ggctcagatg tgagg                      45

<210> SEQ ID NO 39
<211> LENGTH: 45
<212> TYPE: DNA
<213> ORGANISM: Artificial
<220> FEATURE:
<223> OTHER INFORMATION: primer

<400> SEQUENCE: 39
cgccagctgg cgtaatagcg aagagacgcg aagaatcaac cggtg                      45

<210> SEQ ID NO 40
<211> LENGTH: 67
<212> TYPE: DNA
<213> ORGANISM: Artificial
<220> FEATURE:
<223> OTHER INFORMATION: primer

<400> SEQUENCE: 40
actactagca gcagctgtaa tacgactcac tcactatagg gaatattcca ccgtcatatc      60
cgtactg                                                                67

<210> SEQ ID NO 41
<211> LENGTH: 60
<212> TYPE: DNA
<213> ORGANISM: Artificial
<220> FEATURE:
<223> OTHER INFORMATION: primer

<400> SEQUENCE: 41
atgtaagcgt gacataacta attacatgat gcggccctct acgaggattg tttgaagagc      60

<210> SEQ ID NO 42
<211> LENGTH: 45
<212> TYPE: DNA
<213> ORGANISM: Artificial
<220> FEATURE:
```

<223> OTHER INFORMATION: primer

<400> SEQUENCE: 42
cctaaccgag actcctcatt ggagttccat gattgggaga gtcgc          45

<210> SEQ ID NO 43
<211> LENGTH: 45
<212> TYPE: DNA
<213> ORGANISM: Artificial
<220> FEATURE:
<223> OTHER INFORMATION: primer

<400> SEQUENCE: 43
cgccagctgg cgtaatagcg aagagaccac ggaatccatc agctg          45

<210> SEQ ID NO 44
<211> LENGTH: 67
<212> TYPE: DNA
<213> ORGANISM: Artificial
<220> FEATURE:
<223> OTHER INFORMATION: primer

<400> SEQUENCE: 44
actactagca gcagctgtaa tacgactcac tcactatagg gaatattatc tgatatcgac          60
ttatccg          67

<210> SEQ ID NO 45
<211> LENGTH: 60
<212> TYPE: DNA
<213> ORGANISM: Artificial
<220> FEATURE:
<223> OTHER INFORMATION: primer

<400> SEQUENCE: 45
atgtaagcgt gacataacta attacatgat gcggccctct cgataagggc gttacggctc          60

<210> SEQ ID NO 46
<211> LENGTH: 20
<212> TYPE: DNA
<213> ORGANISM: Artificial
<220> FEATURE:
<223> OTHER INFORMATION: primer

<400> SEQUENCE: 46
aggcatagac acaagcgatg          20

<210> SEQ ID NO 47
<211> LENGTH: 60
<212> TYPE: DNA
<213> ORGANISM: Artificial
<220> FEATURE:
<223> OTHER INFORMATION: primer

<400> SEQUENCE: 47
atgtaagcgt gacataacta attacatgat gcggccctct tccttcgcca ttcacacgtc          60

<210> SEQ ID NO 48
<211> LENGTH: 67
<212> TYPE: DNA
<213> ORGANISM: Artificial
<220> FEATURE:
<223> OTHER INFORMATION: primer

<400> SEQUENCE: 48
actactagca gcagctgtaa tacgactcac tcactatagg gaatattcca ccgtcatatc          60

-continued

```
cgtactg                                                              67

<210> SEQ ID NO 49
<211> LENGTH: 60
<212> TYPE: DNA
<213> ORGANISM: Artificial
<220> FEATURE:
<223> OTHER INFORMATION: primer

<400> SEQUENCE: 49
atgtaagcgt gacataacta attacatgat gcggccctct acgaggattg tttgaagagc    60

<210> SEQ ID NO 50
<211> LENGTH: 20
<212> TYPE: DNA
<213> ORGANISM: Artificial
<220> FEATURE:
<223> OTHER INFORMATION: primer

<400> SEQUENCE: 50
cgtacttcca acgatgatcc                                                20
```